United States Patent
Onozawa et al.

(10) Patent No.: US 12,030,833 B2
(45) Date of Patent: Jul. 9, 2024

(54) METHOD FOR PRODUCING HETERO-TYPE MONODISPERSE POLYETHYLENE GLYCOL DERIVATIVE

(71) Applicant: NOF CORPORATION, Tokyo (JP)

(72) Inventors: Akihide Onozawa, Kawasaki (JP); Takashi Ichikawa, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 534 days.

(21) Appl. No.: 17/599,172

(22) PCT Filed: Mar. 25, 2020

(86) PCT No.: PCT/JP2020/013434
§ 371 (c)(1),
(2) Date: Sep. 28, 2021

(87) PCT Pub. No.: WO2020/203580
PCT Pub. Date: Oct. 8, 2020

(65) Prior Publication Data
US 2022/0153683 A1      May 19, 2022

(30) Foreign Application Priority Data

Mar. 29, 2019   (JP) ................. 2019-065528

(51) Int. Cl.
| | | |
|---|---|---|
| C08G 65/08 | (2006.01) | |
| C07C 213/06 | (2006.01) | |
| C07C 213/10 | (2006.01) | |
| C08G 65/30 | (2006.01) | |
| C08G 65/332 | (2006.01) | |
| C08G 65/333 | (2006.01) | |

(52) U.S. Cl.
CPC .......... C07C 213/06 (2013.01); C07C 213/10 (2013.01); C08G 65/08 (2013.01); C08G 65/30 (2013.01); C08G 65/3322 (2013.01); C08G 65/33341 (2013.01)

(58) Field of Classification Search
CPC ...... C07C 229/22; C07C 229/06; C08G 65/08
See application file for complete search history.

(56) References Cited

U.S. PATENT DOCUMENTS

| | | |
|---|---|---|
| 5,672,622 A | 9/1997 | Hedgepeth et al. |
| 2005/0054816 A1* | 3/2005 | McManus ............ C08G 65/329 528/425 |
| 2007/0287762 A1 | 12/2007 | Casati et al. |
| 2016/0075624 A1 | 3/2016 | Yang et al. |
| 2018/0186931 A1* | 7/2018 | Kinbara ............... C08G 65/334 |
| 2020/0079905 A1 | 3/2020 | Hirai et al. |
| 2021/0009756 A1 | 1/2021 | Ogi et al. |
| 2021/0189063 A1 | 6/2021 | Kinbara et al. |

FOREIGN PATENT DOCUMENTS

| | | |
|---|---|---|
| CA | 3039311 A1 | 4/2018 |
| CN | 107189058 A | 9/2017 |
| CN | 107235848 A | 10/2017 |
| JP | 2007-538111 A | 12/2007 |
| JP | 2008-174755 A | 7/2008 |
| JP | 2013-533900 A | 8/2013 |
| JP | 2017-14371 A | 1/2017 |
| JP | 2018-62655 A | 4/2018 |
| JP | 2018-172645 A | 11/2018 |
| JP | 2019-172993 A | 10/2019 |
| WO | 92/01474 A1 | 2/1992 |
| WO | 2005/070973 A2 | 8/2005 |
| WO | 2011/148177 A2 | 12/2011 |
| WO | WO 2017/002853 * | 1/2017 |

OTHER PUBLICATIONS

Szekely, Chem. Eur. J. 2014, 20, 10038-10051 (Year: 2014).*
Office Action dated Feb. 15, 2023, issued by the China National Intellectual Property Administration in corresponding Chinese Patent Application No. 202080026541.5.
Communication issued Dec. 7, 2022 by the European Patent Office for corresponding European Patent Application No. 20784653.6.
Dosio et al., "Immunotoxins and Anticancer Drug Conjugate Assemblies: The Role of the Linkage between Components," Toxins 2011, 3, pp. 848-883; Mar. 2011, Total 32 pages.
Zhao et al., "Synthesis and Evaluation of Hydrophilic Linkers for Antibody-Maytansinoid Conjugates," Journal of Medicinal Chemistry, 2011, 54, pp. 3606-3623, Apr. 2011, Total 9 pages.
Szekely et al., "Iterative synthesis of monodisperse PEG homostars and linear heterobifunctional PEG," Polymer Chemistry, 2014, 5, pp. 694-697, 2014, Total 4 pages.
International Search Report (PCT/ISA/210) dated Jun. 23, 2020, issued by the International Searching Authority in counterpart International Application No. PCT/JP2020/013434.
Written Opinion (PCT/ISA/237) dated Jun. 23, 2020, issued by the International Searching Authority in counterpart International Application No. PCT/JP2020/013434.

* cited by examiner

Primary Examiner — Robert C Boyle
(74) Attorney, Agent, or Firm — Sughrue Mion, PLLC

(57) ABSTRACT

A method for producing a hetero-type monodisperse polyethylene glycol, which includes (A) carrying out a nucleophilic substitution reaction between a compound of formula (2) and a compound of formula (3) so as to satisfy expression (F1) to obtain a compound of formula (4), (B) of carrying out a Michaels addition reaction of a compound of formula (5) to the compound of formula (4) at a temperature condition of 10° C. or lower to obtain a compound of formula (6), (C) detritylating or debenzylating the compound of the formula (6) to obtain a reaction product containing a compound of formula (7), (D) purifying the compound of formula (7) from the reaction product, (E) reacting the compound of formula (7) with phthalimide and performing dephthalimidation to obtain a compound of formula (8), and (F) subjecting the compound of formula (8) to an acid hydrolysis treatment to obtain a compound represented by formula (1).

20 Claims, No Drawings

METHOD FOR PRODUCING HETERO-TYPE MONODISPERSE POLYETHYLENE GLYCOL DERIVATIVE

CROSS-REFERENCE TO RELATED APPLICATIONS

This application is a National Phase Entry of PCT International Application No. PCT/JP2020/013434 filed on Mar. 25, 2020, which claims priority to Japanese Patent Application No. 2019-065528 filed on Mar. 29, 2019.

TECHNICAL FIELD

The present invention relates to a method for producing a hetero-type monodisperse polyethylene glycol to be used for pharmaceutical uses.

BACKGROUND ART

In recent years, in the pharmaceutical field, antibody-drug conjugates (Antibody-Drug Conjugate: ADC), in which a drug and an antibody are bonded via a linker and which can actively carry the drug to antigen-presenting cells, have been put into practical use and have attracted high attention (Toxins, March 2011, p. 848-883 (Non-Patent Literature 1), J. Med. Chem., 2011, 54, p. 3606-3623 (Non-Patent Literature 2).

One material which has been utilized as a linker material for this ADC is a hetero-type monodisperse polyethylene glycol. The hetero-type monodisperse polyethylene glycol is a monodisperse polyethylene glycol containing a hetero-type polyethylene glycol having functional groups different from each other at both terminals as a main component and having a specified molecular weight.

In the above ADC, the hetero-type monodisperse polyethylene glycol is used as a linker, and the antibody and the drug are separately bonded to each terminal thereof. Therefore, when a compound having the same functional groups at both terminals (homo-type polyethylene glycol or the like) is present as an impurity in the hetero-type monodisperse polyethylene glycol, a compound in which two antibodies are bonded or a compound in which two drugs are bonded is formed. The compound in which two antibodies are bonded does not have an effect as an ADC because the drug is not bonded, and the compound in which two drugs are bonded is carried to a site other than the antigen-presenting cell because the antibody is not bonded and the compound causes a side effect. Further, also in the case where another hetero-type compound having functional groups in a combination different from the case of the hetero-type monodisperse polyethylene glycol having the objective functional groups is contained as an impurity, a compound lacking one of the objective antibody and drug is formed, so that the same problem as described above occurs. Therefore, from the viewpoint of the use and effect of the drug, it is important that the hetero-type monodisperse polyethylene glycol contains only one kind of hetero-type monodisperse polyethylene glycol having functional groups different from each other at both terminals in high purity.

Moreover, for the purpose of improving the effect of the above ADC, it has been attempted to use an ADC in which a plural number of drugs are bonded to an antibody. At the time when this ADC is produced, the number of the bonded drugs is confirmed using a mass spectrometer or HPLC. Therefore, when a compound different in ethylene glycol chain length is present in the hetero-type monodisperse polyethylene glycol used as a linker material, there arises a problem in production that confirmation thereof becomes difficult. In addition, when the compound different in ethylene glycol chain length is present as an impurity, there are a problem that it is necessary to excessively use an expensive antibody or drug because an equivalent amount of the antibody or drug to be added at the time of producing the ADC becomes unclear and a problem that, since the compound different in ethylene glycol chain length is treated as a compound different from the main drug at the time of application for a medicinal product, identification of the compound, execution of various tests, evaluation of the allowable amount, and the like are further needed. Therefore, as the hetero-type monodisperse polyethylene glycol, it is important that only one type of polyethylene glycol having the same ethylene glycol chain length is contained in high purity.

As above, as the hetero-type monodisperse polyethylene glycol to be used as a linker material of the ADC, it has been desired to contain a compound which is a hetero-type polyethylene glycol having functional groups different from each other at both terminals as a main component and in which the ethylene glycol chain length is the same between the hetero-type polyethylene glycols, in particularly high purity.

A hetero-type monodisperse polyethylene glycol having an amino group and a carboxyl group as functional groups at respective terminals can be used as it is as a linker of the ADC, and further, a hetero-type monodisperse polyethylene glycol obtained by functional group conversion using this compound as a raw material can also be used as a linker for the ADC.

At the time of producing the hetero-type monodisperse polyethylene glycol, it is necessary to efficiently perform terminal functionalization. As a terminal functionalization step, Patent Literatures 1 and 2 disclose methods of introducing a carboxyl group into the terminal of monomethoxypolyethylene glycol. In Patent Literature 1, monomethoxypolyethylene glycol and acrylonitrile are subjected to the Michael addition reaction, the nitrile is converted to an amide under concentrated hydrochloric acid conditions, and the amide is hydrolyzed under potassium hydroxide aqueous solution conditions, thereby achieving the conversion into a carboxyl group. However, under such strong acid or strong base conditions, a compound having a hydroxyl group instead of a carboxyl group forms through a reverse reaction of the Michael addition reaction and a compound having a short ethylene glycol chain length forms through cleavage of the ethylene glycol chain, so that the purity and yield decrease. In Patent Literature 2, monomethoxypolyethylene glycol and tert-butyl acrylate are subjected to the Michael addition reaction and conversion into a carboxyl group is achieved under trifluoroacetic acid conditions. However, in the method disclosed in the literature, the introduction rate of tert-butyl acrylate is as low as 70% or less, and there is a problem that a compound having a hydroxyl group at the terminal remains.

Further, as a method of introducing an amino group, in Patent Literature 3, in an octaethylene glycol derivative having a terminal vinyl group, the vinyl group is converted into an aldehyde group through ozone oxidation, and it is then converted into an amino group through a reductive amination reaction with sodium cyanoboride in an ammonium chloride solution. However, there is a problem in industrial production from the viewpoint of the formation of explosive peroxides through ozone oxidation and the toxicity of sodium cyanoboride. In Patent Literature 4, a hydroxyl group of an octaethylene glycol derivative is reacted with tosyl chloride to introduce a tosyl group, and the resultant is reacted with potassium phthalimide to convert the group into a phthalimide group, which is converted into an amino group through a deprotection reaction using hydrazine monohydrate. Such Gabriel amine synthesis is a general method for amino group conversion, but in order to introduce an amino group, a step of once introducing a leaving group such as a tosyl group into a hydroxyl group is required. In such a reaction step, the presence of residual unreacted raw materials and formation of reaction by-products are unavoidable, and generally, the more the reaction steps, the lower the yield of the target compound.

Furthermore, Non-Patent Literature 3 discloses a method of synthesizing a compound having an ethylene glycol chain length of 8 and having a 4,4'-dimethoxytrityl group at one terminal and a hydroxyl group at another terminal, in which both terminals are different from each other. A part of the synthetic route is represented by the following formula:

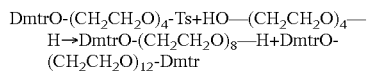

DmtrO-(CH$_2$CH$_2$O)$_4$-Ts+HO—(CH$_2$CH$_2$O)$_4$—H→DmtrO-(CH$_2$CH$_2$O)$_8$—H+DmtrO-(CH$_2$CH$_2$O)$_{12}$-Dmtr wherein Dmtr represents a 4,4'-dimethoxytrityl group, and it is described that, at the time of obtaining a one-terminal Dmtr body of octamer through a 1:1 reaction between a one-terminal tosyl body and tetraethylene glycol, both terminal Dmtr body of dodecamer is formed through a 2:1 reaction between the one-terminal tosyl body and tetraethylene glycol.

However, when a hetero-type polyethylene glycol having an amino group and a carboxyl group at respective both terminals is synthesized using such a mixture containing a compound having Dmtr groups at both terminals, a compound having amino groups at both terminals or a compound having carboxyl groups at both terminals is formed as an impurity. Therefore, when a hetero-type monodisperse polyethylene glycol containing such an impurity is used in the production of an ADC, a compound in which two drugs are bonded or two antibodies are bonded is formed, which causes a decrease in effectiveness as a drug.

As a method for producing the hetero-type polyethylene glycol having functional groups different from each other at both terminals, Patent Literature 3 describes that a triethylene glycol derivative having an amino protecting group at one terminal and an ethylene glycol derivative having a carboxyl protecting group at one terminal are coupled and deprotection is performed at each terminal to obtain a hetero-type monodisperse polyethylene glycol having an amino group and a carboxyl group at respective terminals. However, in the coupling between such polyethylene glycol derivatives into which respective protecting groups have been introduced, one of them is excessively used and hence the cost increases.

Further, in Patent Literature 4 describes a method of obtaining a hetero-type monodisperse polyethylene glycol having an amino group and a carboxyl group at respective terminals in high purity using a hetero-type monodisperse polyethylene glycol having a leaving group at one terminal and a hydroxyl group at the other terminal as an intermediate, which is prepared by sequential synthesis using easily commercially available tetraethylene glycol as a starting material.

However, in this production method, after repeating the sequential synthesis up to the objective ethylene glycol chain length, in order to remove monodisperse polyethylene glycol impurities having protecting groups at both terminals from a hetero-type monodisperse polyethylene glycol having a protecting group at one terminal and a hydroxyl group at the other terminal, the hydroxyl group is once converted into a tosyl group. As described above, the more such a reaction step is added, the lower the yield of the target compound is. Therefore, there is room for further improvement in industrial production.

PRIOR ART DOCUMENTS

Patent Literature

Patent Literature 1: U.S. Pat. No. 5,672,622
Patent Literature 2: JP-T-2007-538111
the term "JP-T" as used herein means a published Japanese translation of a PCT patent application
Patent Literature 3: WO 9201474
Patent Literature 4: JP-A-2017-14371

Non-Patent Literature

Non-Patent Literature 1: Toxins, 2011, March, p. 848-883
Non-Patent Literature 2: J. Med. Chem., 2011, 54, p. 3606-3623
Non-Patent Literature 3: Polym. Chem., 2014, 5, p. 694-697

SUMMARY OF INVENTION

Object to be Achieved by the Invention

An object of the present invention is to provide a production method capable of industrially producing a hetero-type monodisperse polyethylene glycol derivative to be used in pharmaceutical applications in high yield.

Means for Achieving the Object

As a result of intensive studies to achieve the above object, the present inventors have established a method for producing a hetero-type monodisperse polyethylene glycol derivative having the following configuration.

Thus, the present invention is as follows.

(1) A method for producing a hetero-type monodisperse polyethylene glycol represented by the formula (1), which comprises the following steps (A), (B), (C), (D), (E) and (F):

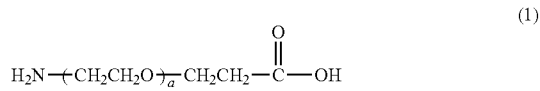

wherein, in the formula (1), a represents an integer of 6 to 12,

Step (A): a step of carrying out a nucleophilic substitution reaction between a compound of the formula (2) and a compound of the formula (3) so as to satisfy the requirement of the expression (F1) to obtain a compound of the formula (4):

wherein, in the formula (2), b represents an integer of 3 to 9,

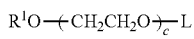 (3)

wherein, in the formula (3), L represents a mesyl group or a tosyl group, $R^1$ represents a trityl group or a benzyl group, and c represents an integer of 3 to 9, $6 \leq b+c \leq 12$ (F1)

 (4)

wherein, in the formula (4), $R^1$ represents a trityl group or a benzyl group and a represents an integer of 6 to 12;

Step (B): a step of carrying out Michael addition reaction of a compound of the formula (5) to the compound of the formula (4) obtained in the step (A) under a temperature condition of 10° C. or lower to obtain a compound of the formula (6),

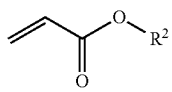 (5)

wherein, in the formula (5), $R^2$ represents a hydrocarbon group having 1 to 6 carbon atoms,

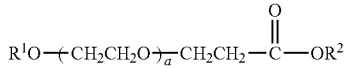 (6)

wherein, in the formula (6), $R^1$ represents a trityl group or a benzyl group, $R^2$ represents a hydrocarbon group having 1 to 6 carbon atoms, and a represents an integer of 6 to 12;

Step (C): a step of detritylating or debenzylating the compound of the formula (6) obtained in the step (B) to obtain a reaction product containing a compound of the formula (7),

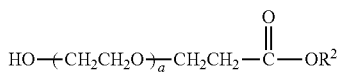 (7)

wherein, in the formula (7), $R^2$ represents a hydrocarbon group having 1 to 6 carbon atoms and a represents an integer of 6 to 12;

Step (D): a step of purifying the compound of the formula (7) from the reaction product obtained in the step (C);

Step (E): a step of reacting the compound of the formula (7) obtained in the step (D) with phthalimide and performing dephthalimidation to obtain a compound of the formula (8),

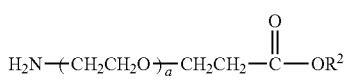 (8)

wherein, in the formula (8), $R^2$ represents a hydrocarbon group having 1 to 6 carbon atoms and a represents an integer of 6 to 12; and Step (F): a step of subjecting the compound of the formula (8) obtained in the step (E) to an acid hydrolysis treatment to obtain the compound represented by the formula (1).

(2) The method according to (1), wherein the compound of the formula (7) is purified using dichloromethane or chloroform in the step (D).

(3) The method according to (1) or (2), wherein the compound of the formula (7) is purified using water or an aqueous solution having a concentration of an inorganic salt of 10% by weight or less in the step (D).

(4) The method according to any one of (1) to (3), wherein the step (D) comprises a washing step at a temperature of 1 to 25° C.

(5) A method for producing a hetero-type monodisperse polyethylene glycol represented by the formula (1), which comprises the following steps (A), (B), (C), (E), (F) and (G):

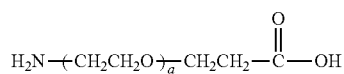 (1)

wherein, in the formula (1), a represents an integer of 13 to 40,

Step (A): a step of carrying out a nucleophilic substitution reaction between a compound of the formula (2) and a compound of the formula (3) so as to satisfy the requirement of the expression (F1) to obtain a compound of the formula (4):

 (2)

wherein, in the formula (2), b represents an integer of 3 to 37,

 (3)

wherein, in the formula (3), L represents a mesyl group or a tosyl group, $R^1$ represents a trityl group or a benzyl group, and c represents an integer of 3 to 37,

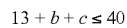 (F1)

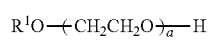 (4)

wherein, in the formula (4), $R^1$ represents a trityl group or a benzyl group and a represents an integer of 13 to 40;

Step (B): a step of carrying out Michael addition reaction of a compound of the formula (5) to the compound of the formula (4) obtained in the step (A) under a temperature condition of 10° C. or lower to obtain a compound of the formula (6),

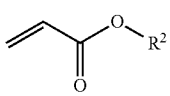

(5)

wherein, in the formula (5), R² represents a hydrocarbon group having 1 to 6 carbon atoms,

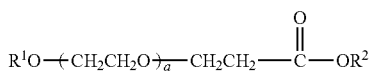

(6)

wherein, in the formula (6), R¹ represents a trityl group or a benzyl group, R² represents a hydrocarbon group having 1 to 6 carbon atoms, and a represents an integer of 13 to 40;
Step (C): a step of detritylating or debenzylating the compound obtained in the step (B) to obtain a compound of the formula (7),

(7)

wherein, in the formula (7), R² represents a hydrocarbon group having 1 to 6 carbon atoms and a represents an integer of 13 to 40;
Step (E): a step of reacting the compound of the formula (7) obtained in the step (C) with phthalimide and performing dephthalimidation to obtain a compound of the formula (8),

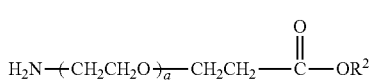

(8)

wherein, in the formula (8), R² represents a hydrocarbon group having 1 to 6 carbon atoms and a represents an integer of 13 to 40;
Step (F): a step of subjecting the compound of the formula (8) obtained in the step (E) to an acid hydrolysis treatment to obtain a reaction product containing the compound of the formula (1); and
Step (G): a step of purifying the compound of the formula (1) from the reaction product obtained in the step (F).

(6) The method according to (5), wherein an organic solvent to be used for the purifying is dichloromethane or chloroform in the step (G).

(7) The method according to (5) or (6), wherein an aqueous solution to be used for the purifying is a basic aqueous solution of pH 8 or higher in the step (G).

(8) The method according to any one of (1) to (7), wherein R² of the compound of the formula (5) is an isopropyl group or a tert-butyl group in the step (B).

(9) The method according to any one of (1) to (8), wherein flaky potassium hydroxide or powdery potassium hydroxide is used as a base in the step (B).

Effect of the Invention

The present invention is a novel method for producing a highly pure hetero-type monodisperse polyethylene glycol having an amino group and a carboxyl group at respective both terminals. In this production method, a highly pure hetero-type monodisperse polyethylene glycol can be produced by simple liquid-separation extraction without using a purification method such as column chromatography during steps. Further, in order to purify both-terminal protected impurities having a specific molecular weight and different in chain length, which are produced as by-products in the conventional chain length extension step, the impurities can be removed without a step of once converting a hydroxyl group into a tosyl group. In this way, since the number of steps is smaller than in the past, it is possible to suppress the presence of residual unreacted raw materials and the formation of reaction by-products, which cause a decrease in yield. Therefore, the method can be provided as an industrial method for producing a highly pure hetero-type monodisperse polyethylene glycol having an amino group and a carboxyl group at respective both terminals.

EMBODIMENTS FOR CARRYING OUT THE INVENTION

The hetero-type monodisperse polyethylene glycol derivative according to the present invention is represented by the following formula (1). The "monodisperse polyethylene glycol" is a compound containing 90% or more of a component having a specific ethylene glycol chain length.

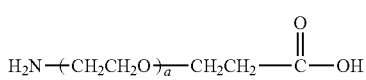

(1)

a in the formula (1) of the present invention is an integer of 6 to 12 or 13 to 40, which represents a repeating unit of ethylene glycol. From the viewpoint of the use as a linker for an ADC, a is preferably an integer of 6 to 12 or 13 to 24.

A highly pure hetero-type monodisperse polyethylene glycol (1) having an amino group and a carboxyl group at respective both terminals can be produced as follows.
(Step (A))
The step (A) according to the present invention is a step of carrying out a nucleophilic substitution reaction between a compound represented by the following formula (2):

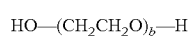
HO—(CH₂CH₂O)_b—H (2)

and a compound represented by the following formula (3):

R¹O—(CH₂CH₂O)_c-L (3)

so as to satisfy the requirement represented by the following expression (F1):

6≤b+c≤12 or 13≤b+c≤40 (F1)

to obtain a compound represented by the following formula (4):

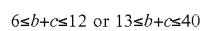
R¹O—(CH₂CH₂O)_a—H (4).

b in the formula (2) represents an integer of 3 to 9 or 3 to 37, and is preferably an integer of 3 to 9 or 10 to 21. R¹ in the formula (3) represents a trityl group or a benzyl group, L represents a mesyl group or a tosyl group, and c represents an integer of 3 to 9 or 3 to 37, and is preferably an integer of 3 to 9 or 10 to 21. Further, b in the formula (2) and c in the formula (3) satisfy b+c=6 to 12 or 13 to 40, thus satisfying the requirement represented by the expression (F1), and preferably b+c=6 to 12 or 13 to 24.

As the compound represented by the formula (2) and the compound represented by the formula (3), commercially available products can be utilized or the compounds can be obtained by known synthetic methods. Also, as the compound represented by the formula (3), it is possible to synthesize a compound having a long ethylene glycol chain length, i.e., a large value of a in the formula (4), utilizing a compound obtained by mesylating or tosylating the compound represented by the formula (4) to be obtained in the present step (A).

By carrying out a nucleophilic substitution reaction between the compound represented by the formula (2) and the compound represented by the formula (3) in the presence of a base, a reaction mixture containing the compound represented by the formula (4) can be obtained. In the formula (4), $R^1$ represents a trityl group or a benzyl group, a represents an integer of 6 to 12 or 13 to 40, and preferably represents an integer of 6 to 12 or 13 to 24. Further, $R^1$ in the formula (4) and $R^1$ in the formula (3) show the same substituent. The reaction mixture contains a compound represented by the following formula (9):

$$R^1O\text{—}(CH_2CH_2O)_d\text{—}R^1 \quad (9)$$

as an impurity.

In the formula (9), $R^1$ represents a trityl group or a benzyl group, and d represents an integer of 3 to 80. Further, $R^1$ in the formula (9) and $R^1$ in the formula (3) show the same substituent.

The nucleophilic substitution reaction can be carried out in a solvent. The solvent is not particularly limited as long as it is a solvent that does not react with the compound represented by the formula (2) and the compound represented by the formula (3). Specifically, aprotic polar solvents such as acetonitrile, dimethylformamide, tetrahydrofuran, dichloromethane, and chloroform and mixed solvents thereof can be used, and preferred are acetonitrile and dimethylformamide. The amount of the solvent to be used is usually 1 to 100 times, preferably 2 to 50 times, more preferably 3 to 30 times in the weight ratio to the compound represented by the formula (3). When the amount of the solvent to be used is less than the lower limit, the amount of the compound represented by the formula (9) in which the compound represented by the formula (3) is bonded to both terminals of the compound represented by the formula (2) tends to be increased, while when the amount exceeds the upper limit, the progress of the nucleophilic substitution reaction tends to be slowed down.

In the nucleophilic substitution reaction, the amount of the compound represented by the formula (2) to be used is usually 1.1 to 50 times, preferably 5.0 to 30 times, more preferably 5.0 to 20 times in the molar ratio to the compound represented by the formula (3). When the amount of the compound represented by the formula (2) to be used is less than the above, the amount of the compound represented by the formula (9) in which the compound represented by the formula (3) is bonded to both terminals of the compound represented by the formula (2) tends to be increased, while when the amount exceeds the upper limit, the progress of the nucleophilic substitution reaction tends to be slowed down.

The base to be used in the nucleophilic substitution reaction is not particularly limited as long as the reaction proceeds, but is specifically sodium hydride, metallic sodium, or potassium tert-butoxide, and is preferably sodium hydride or metallic sodium. The amount of the base to be used is usually 1.1 to 10 times, preferably 1.2 to 5 times in the molar ratio to the compound represented by the formula (3).

The reaction temperature varies depending on the solvent used and the like, but is usually 0 to 100° C., preferably 50 to 90° C. When the reaction temperature is lower than the lower limit, the reaction may be slowed down, while when the reaction temperature exceeds the upper limit, a side reaction may proceed due to the excessive temperature. The reaction time varies depending on the conditions such as the reaction temperature, but is usually 0.2 to 48 hours, preferably 2 to 24 hours. When the reaction time is short, the reaction will be insufficient.

In the step (A), the reaction mixture containing the compound represented by the formula (4) and the compound represented by the formula (9) through such a nucleophilic substitution reaction may be used as it is in the step (B) without purification, or may be used after purifying the compound represented by the above formula (4) by silica gel column chromatography, liquid-separation extraction treatment, adsorption treatment or the like. The compound represented by the formula (9) can be used without purification because it is not reactive in the reaction in the next step (B) and can be removed through purification in the step to be described later.

(Step (B))

The step (B) according to the present invention is a step of carrying out the Michael addition of a compound represented by the following formula (5):

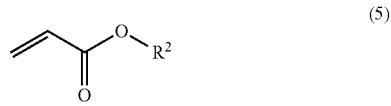

(5)

to the compound represented by the formula (4) under a temperature condition of 10° C. or lower to obtain a compound represented by the formula (6):

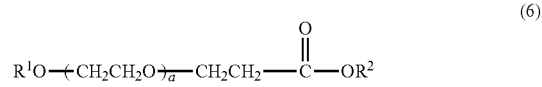

(6)

$R^2$ in the formula (5) represents a hydrocarbon group having 1 to 6 carbon atoms. Specifically, as the hydrocarbon group having 1 to 6 carbon atoms, there may be mentioned a methyl group, an ethyl group, a propyl group, an isopropyl group, a butyl group, a tert-butyl group, an isobutyl group and a sec-butyl group. From the viewpoint of stability under basic conditions, $R^2$ is preferably an isopropyl group or a tert-butyl group. Even more preferably, $R^2$ is a tert-butyl group from the viewpoint of increasing the efficiency of the purification step to be described later.

Further, in the formula (6), $R^1$ represents a trityl group or a benzyl group, $R^2$ represents a hydrocarbon group having 1 to 6 carbon atoms, and a represents an integer of 6 to 12 or 13 to 40, and preferably represents an integer of 6 to 12 or 13 to 24. $R^1$ in the formula (6) and $R^1$ in the formula (4) are the same substituents, and $R^2$ in the formula (6) and $R^2$ in the formula (5) are the same substituents.

The Michael addition reaction can be carried out in a solvent. The solvent is not particularly limited as long as it is a solvent that does not react with the compound represented by the formula (4) and the compound represented by the formula (5). Specifically, organic solvents such as tetrahydrofuran, acetonitrile, dichloromethane, chloroform, and toluene and mixed solvents thereof can be used, and preferred are dichloromethane and chloroform. The amount of the solvent to be used is usually 1 to 100 times, preferably 3 to 50 times, more preferably 5 to 30 times in the weight ratio to the compound represented by the formula (4). When the amount of the solvent used is less than the lower limit, there may occur such an excessive reaction that a compound resulting from the further Michael addition reaction of the compound represented by the formula (5) to the compound represented by the formula (6) is formed, while when the amount exceeds the upper limit, the progress of the Michael addition reaction tends to be slowed down.

In the Michael addition reaction, the amount of the compound represented by the formula (5) to be used is usually 1 to 50 times, preferably 1.5 to 25 times in the molar ratio to the compound represented by the formula (4). When the amount of the compound represented by the formula (5) is less than the lower limit, the Michael addition reaction may not be completed, while when the amount exceeds the upper limit, there is a risk of occurrence of side reactions such as the formation of a polymer of the compound represented by the formula (5).

The base to be used in the Michael addition reaction is not particularly limited as long as the reaction proceeds, but specifically, it is an inorganic catalyst such as sodium hydroxide or potassium hydroxide, and potassium hydroxide is preferable. From the viewpoint of reactivity, flaky potassium hydroxide or powdery potassium hydroxide is more preferable. The amount of the base catalyst to be used is usually 0.1 to 10 times, preferably 0.1 to 5 times in the molar ratio to the compound represented by the formula (4).

The reaction temperature is usually 10° C. or lower, preferably 5° C. or lower. When the reaction temperature exceeds the upper limit, there may occur such an excessive reaction that a compound resulting from the further Michael addition reaction of the compound represented by the formula (5) to the compound represented by the formula (6) is formed. The reaction time varies depending on the conditions such as the reaction temperature and the base catalyst, but is usually 0.2 to 12 hours, preferably 0.5 to 6 hours In the step (B), the reaction mixture containing the compound represented by the formula (6) obtained by such Michael addition reaction and the compound represented by the formula (9) formed in the step (A) may be used as it is in the next step (C) without purification, or it may be used after purifying the compound represented by the formula (6) by silica gel column chromatography, liquid-separation extraction treatment, adsorption treatment or the like. However, in the present invention, since purification is possible in the step to be described later, the reaction mixture can be used without purification.

(Step (C))

The step (C) according to the present invention is a step of detritylating or debenzylating the compound represented by the formula (6) to obtain a compound represented by the formula (7):

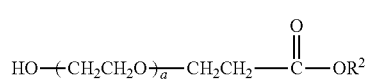

(7)

A reaction product containing the compound represented by the formula (7) can be obtained by detritylation when $R^1$ in the formula (6) is a trityl group or debenzylation when $R^1$ is a benzyl group. Incidentally, the reaction product contains a compound represented by the following formula (10):

(10)

as an impurity, which is formed by detritylating or debenzylating the compound represented by the formula (9) formed in the step (A). In the above formula (10), d represents an integer of 3 to 80.

As methods for the detritylation and debenzylation, known methods can be used, and for example, the methods described in Protective Groups in Organic Synthesis written by GREENE WUTS are effective. When $R^1$ in the formulas (6) and (9) is a trityl group, detritylation can be achieved by a conversion reaction under acidic conditions, catalytic hydrogenation, or the like. As the conversion reaction under acidic conditions, there is no problem as long as it is performed under acidic conditions that do not decompose the target compound (7). Specifically, there is a method of adding a catalytic amount of p-toluenesulfonic acid monohydrate in a methanol solvent to carry out a detritylation reaction.

Further, as the method by catalytic hydrogenation, there is a method of adding a catalytic amount of palladium/carbon to carry out a debenzylation reaction in a methanol solvent under a hydrogen atmosphere. On the other hand, when $R^2$ in the formulas (6) and (9) is a benzyl group, debenzylation can be achieved by catalytic hydrogenation. Specifically, the debenzylation can be performed in a methanol solvent under a hydrogen atmosphere with adding a catalytic amount of palladium/carbon.

In the step (C), a reaction mixture containing the compound represented by the formula (7) and the compound represented by the formula (10) can be obtained by such detritylation or debenzylation. This reaction mixture may be used as it is in the next step (D) without purification, or may be used after the compound represented by the formula (6) is purified by silica gel column chromatography, liquid-separation extraction treatment, adsorption treatment, or the like. However, in the present invention, since purification is possible in the step to be described later, the mixture can be used without purification.

(Step (D))

The step (D) according to the present invention is a step of purifying the reaction product containing the compound represented by the formula (7) obtained in the step (C), in which a is an integer of 6 to 12 in particular. This purification step is a step of removing the compound represented by the formula (10) formed as an impurity in the step (C), and from the viewpoint of determining an appropriate amount of reagents to be used for the reaction and suppressing complication of the purification step, it is preferable also as an industrial production method to remove the impurity compound represented by the formula (10) in this step (D).

Since both terminals of the compound represented by the formula (10) formed as an impurity in the step (C) are hydroxyl groups, as compared with the compound represented by the formula (7) in which a is an integer of 6 to 12, a difference in polarity occurs, so that the impurity of the formula (10) can be removed only by simple liquid-separation extraction without purification by silica gel chromatography. On the other hand, in the case of the compound represented by the formula (7) in which a is an integer of 13 to 40, the difference in polarity from the impurity compound represented by the formula (10) becomes small, so that the removal efficiency decreases.

In the step (D), it is a step in which the reaction product obtained in the step (C) is dissolved in an organic solvent and then subjected to liquid-separation washing with water or an aqueous solution at 25° C. or lower. The organic solvent includes dichloromethane, chloroform and toluene, and dichloromethane and chloroform are preferable from the viewpoint of solubility of the compound represented by the formula (7). The amount of the organic solvent to be used is usually 2 to 30 times, preferably 3 to 20 times in the weight ratio to the reaction mixture containing the compound represented by the formula (7) and the compound represented by the formula (10). When the amount of the organic solvent to be used is less than the lower limit, the compound represented by the formula (7) may dissolve in the aqueous layer, while when the amount exceeds the upper limit, the compound represented by the formula (10) may dissolve in the organic layer, and the liquid-separation washing efficiency decreases.

The water or aqueous solution to be used for washing is not particularly limited as long as the compound represented by the formula (10) can be dissolved, but specifically, there are included water such as ion-exchanged water or distilled water and aqueous solutions of inorganic salts such as sodium chloride and potassium chloride. The concentration of the inorganic salt is not particularly limited as long as the inorganic salt dissolves in the aqueous solution, but is preferably 10% by weight or less, more preferably 5% by weight or less. When the concentration of the inorganic salt in the aqueous solution exceeds the upper limit, the washing efficiency of the compound represented by the formula (10) decreases. The amount of the water or aqueous solution to be used is usually 2 to 30 times, preferably 3 to 20 times in the weight ratio to the reaction mixture containing the compound represented by the formula (7) and the compound represented by the formula (10). When the amount of the water or aqueous solution used is less than the lower limit, the washing efficiency of the compound represented by the formula (10) decreases, while when the amount exceeds the upper limit, the compound represented by the formula (7) may dissolve in the aqueous layer, and the yield of the target compound decreases.

In the step (D), the ratio of the organic solvent to the water or the aqueous solution is usually such that the value of organic solvent/water or aqueous solution is 0.2 to 3.5, preferably 1.0 to 3.5 in weight ratio.

In the step (D), the washing temperature is 1 to 25° C., preferably 5 to 20° C. When the temperature is lower than the lower limit, water or the aqueous solution is solidified and thus purification becomes difficult, while when the temperature exceeds the upper limit, the compound represented by the formula (10) dissolves in the organic layer, and the removal tends to be difficult. The number of times of performing the liquid-separation washing is not particularly limited, and it is preferable to perform the liquid-separation washing a plurality of times while confirming the compound represented by the formula (10) contained in the organic solvent by TLC, MS measurement, or the like.

In the step (D), since impurities formed in the steps (A) to (C) can be removed by such a simple liquid-separation extraction treatment, purification by silica gel chromatography or the like is not necessary in each step. The obtained compound represented by the formula (7) can be used as it is in the step (E), or may be further purified by a treatment such as crystallization, an adsorbent treatment, or silica gel chromatography before use.

(Step (E))

The step (E) according to the present invention is a step of bonding the hydroxyl group of the compound represented by the above formula (7) obtained in the step (C) or the step (D) and phthalimide by the Mitsunobu reaction and deprotecting the resultant with a polyvalent amine to obtain a compound represented by the following formula (8):

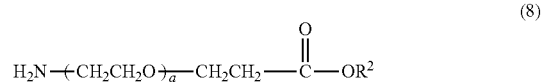

When the purification step of the step (D) has not been performed (the case where a in the formula (7) is 13 to 40), the reaction product contains a compound represented by the following formula (11):

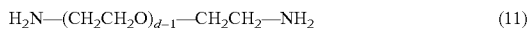

which is formed through bonding of the compound represented by the formula (10) formed in the step (C) to phthalimide and deprotection of the resultant, as an impurity. In the formula (11), d represents an integer of 3 to 80.

The reaction with phthalimide in the step (E) can be carried out in a solvent. The solvent is not particularly limited as long as it does not react with the compound represented by the formula (7) and phthalimide. Specifically, organic solvents such as dichloromethane, chloroform and toluene and mixed solvents thereof can be used, and preferred are dichloromethane and chloroform. The amount of the solvent to be used is usually 1 to 50 times, preferably 3 to 30 times, more preferably 5 to 20 times in the weight ratio to the compound represented by the formula (7).

In the reaction with phthalimide in the step (E), the amount of phthalimide to be used is usually 1.0 to 10 times, preferably 1.3 to 5 times in the molar ratio to the compound represented by the formula (7). When the amount of phthalimide used is less than the lower limit, the reaction may not be completed, while when the amount exceeds the upper limit, unreacted phthalimide remains and hence a step of removing it is necessary, so that the yield decreases.

As an azo-based reagent to be used in the reaction with phthalimide in the step (E), there may be mentioned 1,1'-azobis(N,N-dimethylformamide), 1,1'-(azodicarbonyl)dipiperidine, dibenzyl azodicarboxylate, diethyl azodicarboxylate, diisopropyl azodicarboxylate, dimethyl azodicarboxylate, 1,1'-azobis(N,N-diisopropylformamide), 1,6-dimethyl-1,5,7-hexahydro-1,4,6,7-tetrazocin-2,5-dione, and the like, and preferred are diethyl azodicarboxylate, diisopropyl azodicarboxylate and more preferred is diisopropyl azodicarboxylate. The amount of the azo-based reagent to be used is usually 1.0 to 10 times, preferably 1.1 to 5 times in the molar ratio to the compound represented by the formula (7). As a phosphine-based reagent to be used, there may be mentioned dicyclohexylphenylphosphine, diethylphenylphosphine, 4-(dimethylamino)phenyldiphenylphosphine, diphenyl-2-pyridylphosphine, isopropyldiphenylphosphine, triisobutylphosphine, tri-n-butylphosphine, tri-t-butylphosphine, tricyclohexylphosphine, tri-n-hexylphosphine, tri-n-octylphosphine, triphenylphosphine, and the like, and triphenylphosphine is preferable. The amount of the phosphine-based reagent to be used is usually 1.0 to 10 times, preferably 1.3 to 5 times in the molar ratio to the compound represented by the formula (7).

The reaction temperature is usually 0° C. to 100° C., preferably 10° C. to 50° C. The reaction time is usually 10 minutes to 12 hours, preferably 0.5 to 6 hours.

In the deprotection in the step (E), the method is not particularly limited as long as it is described in Protective Groups in Organic Synthesis written by GREENE WUTS, but it is preferable to use a polyvalent amine.

In the deprotection in the step (E), the solvent to be used include dichloromethane, chloroform, methanol, ethanol and the like, and methanol is preferable. The amount of the solvent to be used is usually 1 to 50 times, preferably 2 to 30 times, more preferably 3 to 20 times in the weight ratio to the compound represented by the formula (7).

In the deprotection in the step (E), the polyvalent amine to be used includes hydrazine monohydrate, ethylenediamine, and ethylenediamine monohydrate. The amount of the polyvalent amine to be used is usually 1 to 50 times, preferably 5 to 30 times in the molar ratio to the compound represented by the formula (7). When the amount of the polyvalent amine used is less than the lower limit, the deprotection reaction becomes insufficient. The reaction temperature is usually 10° C. to 80° C., preferably 20° C. to 60° C. The reaction time is usually 0.5 to 24 hours, preferably 1.0 to 12 hours.

In the step (E), the reaction mixture containing the compound represented by the formula (8) and the compound represented by the formula (11) obtained by the Mitsunobu reaction and deprotection may be used as it is in the next step (F) without purification, or may be used after purifying the compound represented by the formula (8) by silica gel column chromatography, liquid-separation extraction treatment, adsorption treatment, and the like. In the present invention, since purification is possible in the step to be described later, the reaction mixture can be used without purification.

(Step (F))

The step (F) according to the present invention is a step of subjecting the reaction product represented by the formula (8) obtained in the step (E) to an acid hydrolysis treatment to obtain the hetero monodisperse polyethylene glycol containing the compound represented by the formula (1).

The hydrolysis treatment can be carried out in a solvent. The solvent is a solvent such as water, tetrahydrofuran, acetonitrile, chloroform, or dichloromethane, and a mixed solvent thereof. Water or dichloromethane is preferred. The amount of the solvent to be used is usually 0.5 to 50 times, preferably 0.8 to 40 times, more preferably 1 to 30 times in the weight ratio to the compound represented by the formula (8). When the amount of the solvent used is less than the lower limit, the viscosity of the reaction solution becomes high, the stirring efficiency may decrease, and the reaction may not be completed. On the other hand, when the amount exceeds the upper limit, the progress of the reaction tends to be slowed down.

An acid catalyst is used in the hydrolysis. The acid catalyst is not particularly limited as long as the reaction proceeds, and specifically, is hydrochloric acid, phosphoric acid, trifluoroacetic acid, or the like. Hydrochloric acid is preferable from the viewpoint of suppressing a side reaction. The amount of the acid catalyst to be used varies depending on the type of the acid catalyst used, but specifically, when 1M hydrochloric acid is used, it is usually 0.5 to 10 times in the weight ratio to the compound represented by the formula (8).

The reaction temperature for the acid hydrolysis varies depending on the acid catalyst used, but is usually 10 to 100° C. The reaction time for the acid hydrolysis varies depending on conditions such as the reaction temperature, but is usually about 0.5 to 12 hours.

In the step (F), such an acid hydrolysis treatment, a reaction mixture containing the compound represented by the formula (1) and the compound represented by the formula (11) can be obtained. Since this reaction mixture can be purified in the step to be described later, it can be used without purification.

(Step (G))

The step (G) according to the present invention is a step of purifying the reaction mixture containing the compound represented by the formula (1) obtained in the step (F). As long as the compound in which a in the formula (1) is an integer of 6 to 12 is purified in the step (D), this step (G) is not necessarily performed, but may be carried out. However, the step (G) is a purification step necessary for the compound in which a in the formula (1) is an integer of 13 to 40.

In the step (G), it is a step in which the reaction product obtained in the step (F) is dissolved in an aqueous solution and then subjected to liquid-separation washing with an organic solvent at 30° C. or lower. The aqueous solution is a basic aqueous solution having a pH of 8 or higher, and specifically, a sodium hydroxide aqueous solution or a potassium hydroxide aqueous solution adjusted to pH 9 to 11 is preferable. The amount of the basic aqueous solution to be used is usually 2 to 30 times, preferably 3 to 20 times in the weight ratio to the reaction mixture containing the compound represented by the formula (1) and the compound represented by the formula (11). When the amount of the basic aqueous solution used is less than the lower limit, the compound represented by the formula (1) may dissolve in the organic solvent, while when the amount exceeds the upper limit, the liquid-separation washing efficiency may decrease.

The organic solvent to be used for washing is not particularly limited as long as the impurity compound represented by the formula (11) can be dissolved, but specifically include ethyl acetate, toluene, chloroform and dichloromethane, and chloroform and dichloromethane are preferable from the viewpoint of solubility of the impurity. The amount of the organic solvent to be used is usually 2 to 30 times, preferably 3 to 20 times in the weight ratio to the reaction mixture containing the compound represented by the formula (8) and the compound represented by the formula (11). When the amount of the organic solvent used is less than the lower limit, the removal efficiency of the compound represented by the formula (11) decreases, while when the amount exceeds the upper limit, the compound represented by the formula (1) may dissolve in the organic layer, and the yield of the target compound decreases.

In the step (G), the ratio of the organic solvent to the basic aqueous solution is usually such that the value of organic solvent/basic aqueous solution is 0.2 to 3.0, preferably 0.5 to 2.0 in the weight ratio. The number of times of the liquid-separation washing is not particularly limited, and it is preferable to perform the liquid-separation washing a plurality of times while confirming the compound represented by the formula (11) contained in the aqueous solution by TLC, MS measurement, or the like.

According to the present invention, a highly pure hetero-type monodisperse polyethylene glycol can be produced by simple liquid-separation extraction without using a purification method such as column chromatography during the process. Further, in order to purify a both-terminal protected impurity having a specific molecular weight and different in chain length, which is formed as a by-product in the conventional chain length extension step, the impurity can be removed without a step of once converting a hydroxyl group into a tosyl group. In this way, since the number of steps is smaller than in the past, it is possible to suppress the presence of residual unreacted raw materials and the formation of reaction by-products, which cause a decrease in yield. Therefore, the method can be provided as an industrial method for producing a highly pure hetero-type monodisperse polyethylene glycol having an amino group and a carboxyl group at respective both terminals in good yields.

EXAMPLES

Hereinafter, the present invention will be described in more detail with reference to Examples, but the present invention is not limited to the following Examples.

For the measurement of the monodisperse polyethylene glycol obtained in the present invention, JNM-ECP400 or JNM-ECP600 manufactured by JEOL Datum Co., Ltd. was used in $^1$H-NMR analysis. A 5 mmφ tube was used for the measurement, $CDCl_3$ or $CDOD_3$ was used as deuterated solvents, and tetramethylsilane (TMS) was used as an internal standard substance.

The monodisperse polyethylene glycol having one-terminal trityl group which is obtained by the production method of the step (A) and is a compound represented by the above formula (4) ($R^1$ is a trityl group), in which a is 8 or 12, contains a monodisperse polyethylene glycol impurities having both-terminal trityl group which is a compound represented by the formula (9). Although it is difficult to accurately quantify the content, the hydroxyl group of the monodisperse polyethylene glycol having one-terminal trityl group is reacted with methanesulfonyl chloride, and from $^1$H-NMR measurement results of the resulting compound, the content of the monodisperse polyethylene glycol impurities having both-terminal trityl group contained in each step was estimated.

In the reaction in each Example, since the exact number of moles of the monodisperse polyethylene glycol having one-terminal trityl group is unclear, a reagent equivalent was calculated on the assumption that all the amount was derived from the monodisperse polyethylene glycol having one-terminal trityl group.

Example 1

Synthesis of compound 10 in which a in formula (1) is 8

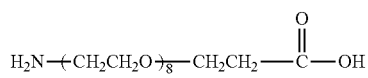

(10)

Example 1-1

Synthesis of compound 4 in which a is 4, $R^1$ is trityl group, and L is mesyl group in formula (3)

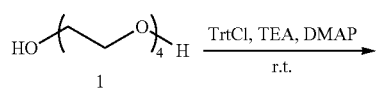

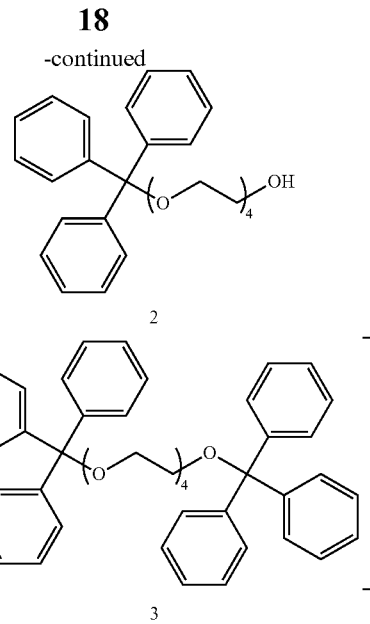

Tetraethylene glycol 1 (3416 g, 17.6 mol) and toluene (3.7 L) were added to a reactor fitted with a thermometer, a nitrogen inlet tube and a stirrer and the whole was dissolved under a nitrogen atmosphere, followed by azeotropic dehydration at 110 to 120° C. After the azeotropic dehydration, the mixture was cooled, triethylamine (736 ml, 5.3 mol), DMAP (54 g, 0.44 mol) and trityl chloride (TrtCl, 1226 g, 4.4 mol) were added, and the mixture was stirred at room temperature for 3 hours. After 3 hours, the disappearance of TrtCl was confirmed using thin layer chromatography (TLC), a 5% aqueous sodium dihydrogen phosphate solution (6.1 L) was added, and liquid separation was performed. The organic layer was washed once with a 5% aqueous sodium dihydrogen phosphate solution (6.1 L), once with a saturated aqueous sodium hydrogen carbonate solution (6.1 L), and once with a saturated aqueous sodium chloride solution (6.1 L). Sodium sulfate was added to the organic layer for dehydration, followed by filtration. The filtrate was concentrated under reduced pressure to obtain a reaction product containing the compound 2 as a pale yellow transparent liquid. Moreover, it was confirmed from TLC analysis and $^1$H-NMR measurement results that the obtained reaction product contained the above compound 3.

Compound 2

$^1$H-NMR ($CDCl_3$, internal standard TMS); δ (ppm):

2.4 (1H, t, —C—($OCH_2CH_2$)$_4$—OH), 3.23 (2H, t, ($C_6H_5$)$_3$C—$OCH_2CH_2$—, including one derived from compound 3)

3.45-3.85 (14H, m, —$OCH_2CH_2$—($OCH_2CH_2$)$_3$—OH, including one derived from compound 3), 7.21-7.47 (15H, m, ($C_6H_5$)$_3$C—$OCH_2CH_2$—, including one derived from compound 3)

Yield: 1687 g

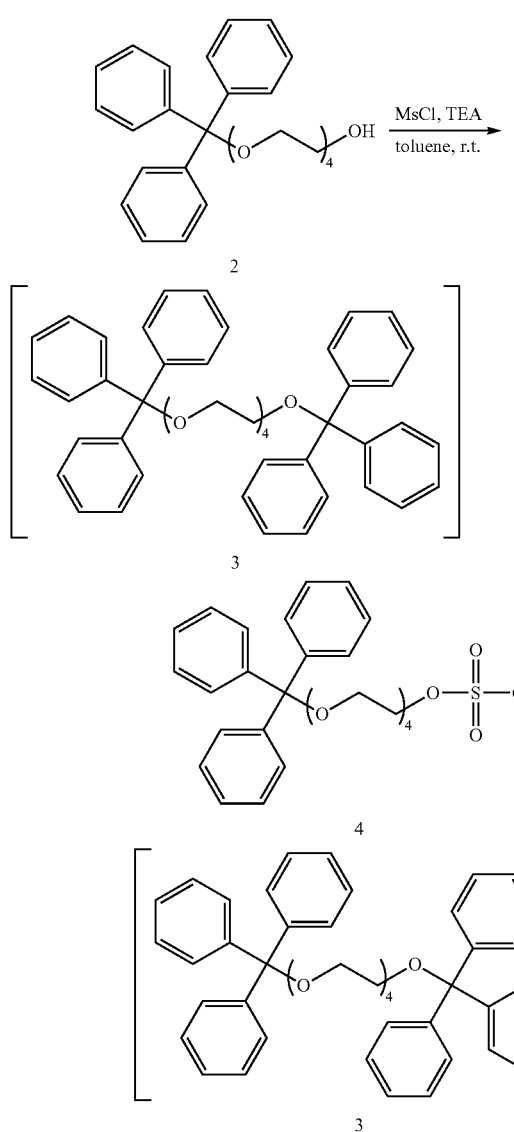

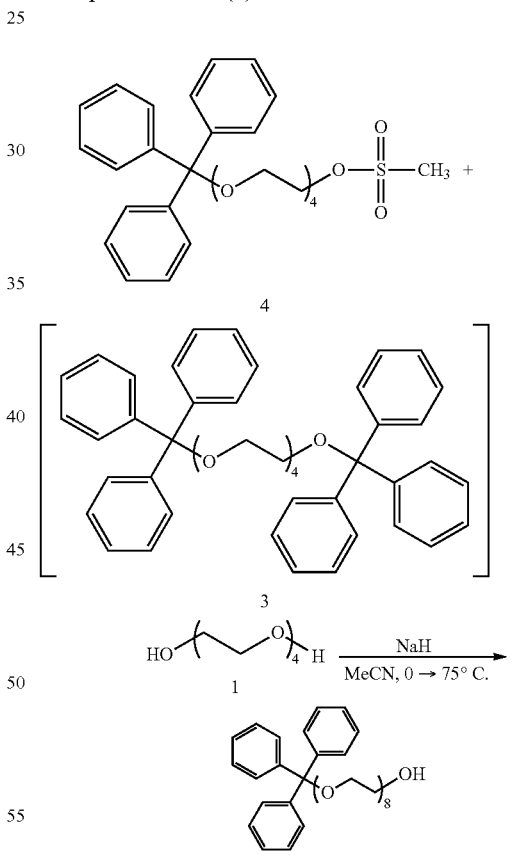

The reaction product containing the compound 2 (compound 2: 1672 g, less than 3.83 mol) and toluene (8.4 L) were added to a reaction vessel fitted with a thermometer, a nitrogen inlet tube and a stirrer and the product was dissolved under a nitrogen atmosphere, followed by addition of triethylamine (643 ml, 4.62 mol). Methanesulfonyl chloride (326 mL, 4.22 mol) was added dropwise at 10° C., and the mixture was stirred at room temperature for 2 hours. After 2 hours, the disappearance of the compound 2 was confirmed by TLC analysis, a 5% aqueous sodium dihydrogen phosphate solution (8.4 L) was added, and liquid separation was performed. The organic layer was washed once with a 5% aqueous sodium dihydrogen phosphate solution (8.4 L), once with a saturated aqueous sodium hydrogen carbonate solution (8.4 L), and once with a saturated aqueous sodium chloride solution (8.4 L). Sodium sulfate was added to the organic layer for dehydration, followed by filtration. The filtrate was concentrated under reduced pressure to obtain a reaction product containing the compound 4 as a pale yellow transparent liquid. Moreover, it was confirmed from TLC analysis and $^1$H-NMR measurement results that the obtained reaction product contained the above compound 3.

Compound 4
$^1$H-NMR (CDCl$_3$, internal standard TMS); δ (ppm):
2.98 (3H, s, —OCH$_2$CH$_2$—O—SO$_2$CH$_3$),
3.23 (2H, t, (C$_6$H$_5$)$_3$C—OCH$_2$CH$_2$—, including one derived from compound 3)
3.45-3.85 (12H, m, —OCH$_2$CH$_2$—(OCH$_2$CH$_2$)$_2$—OCH$_2$CH$_2$—, including one derived from compound 3),
4.33 (2H, t, —OCH$_2$CH$_2$—O—SO$_2$CH$_3$),
7.21-7.47 (15H, m, (C$_6$H$_5$)$_3$C—OCH$_2$CH$_2$—, including one derived from compound 3)
Yield: 1942 g From the $^1$H-NMR measurement results of the compound 4 of Example 1-1, it was confirmed that the compound 3 was contained in an amount of about 6.2 mol %.

A calculation expression of the compound 3 content on the basis of a δ 3.23 peak is expressed by the following expression.

(((2−[δ 4.32])/4H)/([δ 4.32]/2H))×100 (mol %)

Further, the reaction product 2 obtained in Example 1-1 contains the compound 3 in an amount of about 8.8 wt %.

(Example 1-2, Step (A))

Synthesis of Compound 5 in which a is 8 and R$^1$ is Trityl Group in Formula (4)

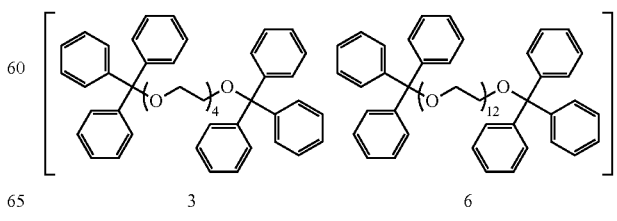

Sodium hydride (215 g) was placed in a reactor fitted with a thermometer, a nitrogen inlet tube and a stirrer, and after nitrogen substitution, MeCN (3.9 L) was added and the mixture was cooled to 0° C. MeCN (2.1 L) was mixed with tetraethylene glycol 1 (3660 g, 18.8 mol) azeotropically dehydrated with toluene (1.8 L), and this mixed solution was added dropwise over 2 hours. After completion of the dropwise addition, MeCN (2.1 L) was mixed with the reaction product containing the compound 4 (compound 4: 1942 g, less than 3.77 mol), and the mixed solution was added dropwise over 20 minutes. After completion of the dropwise addition, the reaction mixture was heated to 75° C. and stirred for 3 hours. After 3 hours, it was confirmed using TLC that the compound 4 had disappeared, and the mixture was allowed to cool until the temperature became 40° C. or lower. A saturated aqueous ammonium chloride solution (3.9 L) and hexane (3 L) were added to the reaction mixture solution and liquid separation was performed. The lower layer from which the hexane layer (upper layer) had been removed was concentrated under reduced pressure, and toluene (9.7 L) was added to the residue. This toluene solution was washed once with a saturated aqueous ammonium chloride solution (5.8 L) and three times with a saturated aqueous sodium chloride solution (9.7 L). Sodium sulfate was added to the organic layer for dehydration, followed by filtration. The filtrate was concentrated under reduced pressure to obtain a reaction product containing the compound 5 as a pale yellow transparent liquid. Moreover, it was confirmed from TLC analysis and $^1$H-NMR measurement results that the obtained reaction products contained the above compounds 3 and 6.

Compound 4

$^1$H-NMR (CDCl$_3$, internal standard TMS); δ (ppm):

2.52 (1H, t, —C—(OCH$_2$CH$_2$)$_8$—OH), 3.23 (2H, t, (C$_6$H$_5$)$_3$C—OCH$_2$CH$_2$—, including those derived from compounds 3 and 6)

3.45-3.85 (30H, m, —OCH$_2$CH$_2$—(OCH$_2$CH$_2$)$_7$—OH, including those derived from compounds 3 and 6), 7.21-7.47 (15H, m, (C$_6$H$_5$)$_3$C—OCH$_2$CH$_2$—, including those derived from compounds 3 and 6)

Yield: 2195 g (Example 1-3, Step (B))

Synthesis of Compound 7 in which a is 8, R$^1$ is Trityl Group, and R$^2$ is Tert-Butyl Group in Formula (6)

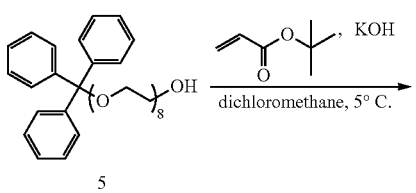

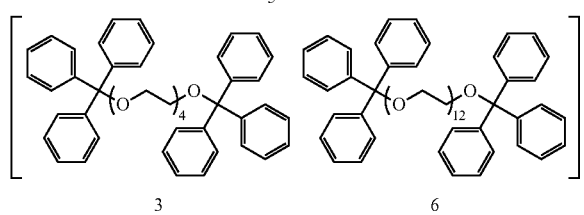

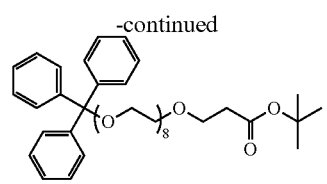

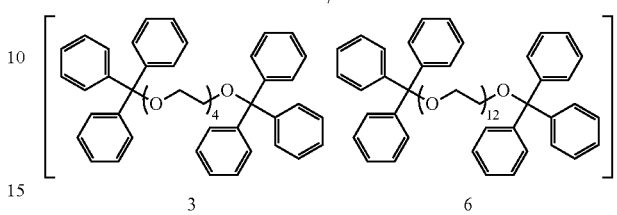

The reaction product containing the compound 5 (compound 5: 2190 g, less than 3.58 mol) and dichloromethane (11 L) were added to a reaction vessel fitted with a thermometer, a nitrogen inlet tube and a stirrer, and the whole was dissolved under a nitrogen atmosphere, followed by addition of powdery potassium hydroxide (21 g, 0.37 mol). After cooling to 5° C., tert-butyl acrylate (a compound in which R$^2$ in the formula (5) is a tert-butyl group, 780 mL, 5.38 mol) was added dropwise, and the mixture was reacted at 5° C. for 1 hour. After the reaction, a saturated aqueous ammonium chloride solution (4.0 L) was added and liquid separation was performed. The organic layer was washed once with a saturated aqueous sodium chloride solution (5.5 L). The organic layer was concentrated under reduced pressure to obtain a reaction product containing the compound 4 as a pale yellow transparent liquid. Moreover, it was confirmed from TLC analysis and $^1$H-NMR measurement results that the obtained reaction products contained the above compounds 3 and 6.

Compound 7

$^1$H-NMR (CDCl$_3$, internal standard TMS); δ (ppm):

1.44 (9H, s, —CH$_2$CH$_2$—COO—C(CH$_3$)$_3$), 2.49 (2H, t, —CH$_2$CH$_2$—COO—C(CH$_3$)$_3$), 3.23 (2H, t, (C$_6$H$_5$)$_3$C—OCH$_2$CH$_2$—, including those derived from compounds 3 and 6), 3.45-3.85 (32H, m, —OCH$_2$CH$_2$—(OCH$_2$CH$_2$)$_7$—OCH$_2$CH$_2$—, including those derived from compounds 3 and 6), 7.21-7.47 (15H, m, (C$_6$H$_5$)$_3$C—OCH$_2$CH$_2$—, including those derived from compounds 3 and 6)

Yield: 2588 g (Yield: 98%)

(Example 1-4, Steps (C), (D))

Synthesis of Compound 8 in which a is 8 and $R^2$ is a Tert-Butyl Group in Formula (7)

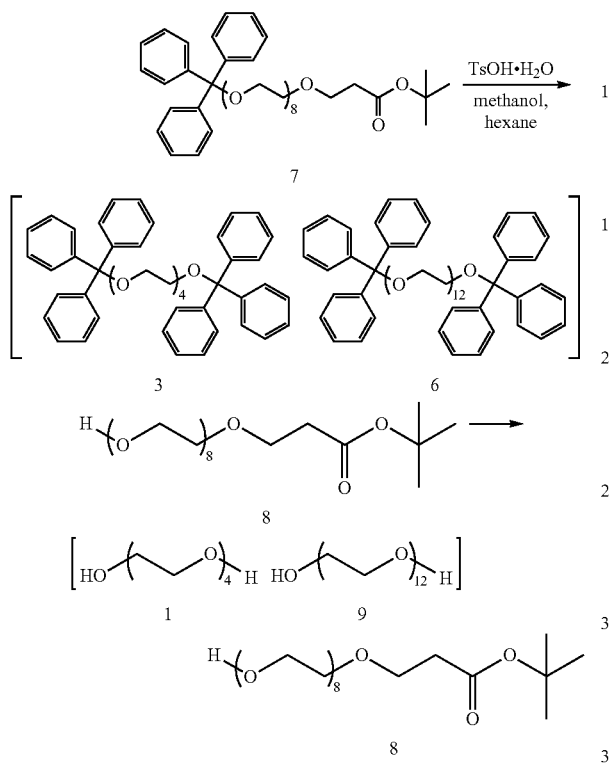

A reaction product containing the compound 7 (compound 7: 2588 g, less than 3.49 mol) and methanol (12.9 L) were added to a reaction vessel fitted with a thermometer, a nitrogen inlet tube and a stirrer, and the whole was dissolved under a nitrogen atmosphere. Thereafter, p-toluenesulfonic acid monohydrate (338 g, 1.78 mol) and hexane (10 L) were added. After stirring at room temperature for 30 minutes, the hexane layer was removed, hexane (6.5 L) was added again, and the mixture was stirred for 30 minutes. After performing the same operation 5 times, the disappearance of the compounds 7, 3 and 6 was confirmed as a result of $^1$H-NMR measurement, and a saturated aqueous sodium hydrogen carbonate solution (5.2 L) was added. The mixed solution was washed once with hexane (6.5 L) to remove trityl methyl ether. The methanol solution was concentrated under reduced pressure to obtain a crude product containing the compound 8. It was confirmed from TLC analysis and $^1$H-NMR measurement results that the obtained crude product contained the above compounds 1 and 9.

Next, dichloromethane (12.9 L) was added to the crude product, and the mixture was washed three times with ion-exchanged water (12.9 L) and once with a saturated aqueous sodium chloride solution (12.9 L) under the condition of 10° C. From TLC analysis, the disappearance of the compounds 1 and 9 was confirmed. Magnesium sulfate was added to the organic layer for dehydration, followed by filtration. The filtrate was concentrated under reduced pressure to obtain a purified product containing the compound 8 as a pale yellow transparent liquid.

Compound 8
$^1$H-NMR (CDCl$_3$, internal standard TMS); δ (ppm):
1.44 (9H, s, —CH$_2$CH$_2$—COO—C(CH$_3$)$_3$),
2.50 (2H, t, —CH$_2$CH$_2$—COO—C(CH$_3$)$_3$),
2.6 (1H, t, H—(OCH$_2$CH$_2$)$_8$—OCH$_2$CH$_2$—),
3.45-3.85 (34H, m, H—(OCH$_2$CH$_2$)$_8$—OCH$_2$CH$_2$—)
Yield: 1229 g (yield: 71%)

(Example 1-5, Step (E))

Synthesis of Compound 9 in which a is 8 and $R^2$ is Tert-Butyl Group in Formula (8)

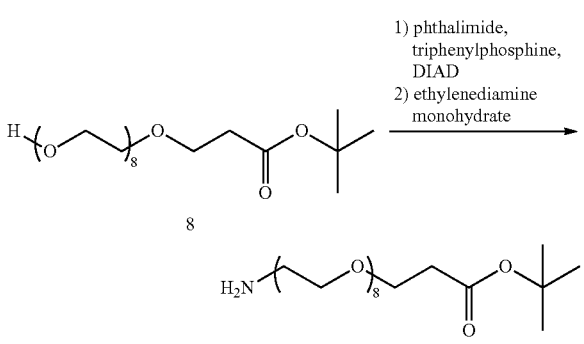

The compound 8 (1229 g, 2.46 mol) and dichloromethane (4.9 L) were added to a reaction vessel fitted with a thermometer, a nitrogen inlet tube and a stirrer and the whole was dissolved under a nitrogen atmosphere. Then, phthalimide (508 g, 3.45 mol), triphenylphosphine (906 g, 3.45 mol) were added. After stirring at room temperature for 30 minutes, diisopropyl azodicarboxylate (599 g, 2.96 mol) diluted with dichloromethane (1.2 L) was added dropwise, and the mixture was stirred for 1 hour. After 1 hour, the disappearance of the compound 8 was confirmed by TLC, the solvent was distilled off under reduced pressure, methanol (5.4 L) and ethylenediamine monohydrate (2 L, 24.7 mol) were added, and a reaction was carried out at 40° C. for 2 hours. A 6N aqueous hydrochloric acid solution was added thereto for neutralization, the solvent was distilled off under reduced pressure, sodium chloride and chloroform (6.1 L) were added for extraction, and a saturated aqueous sodium chloride solution (6.2 L) was added to this extract solution, followed by washing twice. A 1% aqueous sodium dihydrogen phosphate solution (6.2 L) was added to the organic layer, and the mixture was extracted three times. A mixed solvent of chloroform (2.2 L) and toluene (4 L) was added to the extracted aqueous solution, and the mixture was washed 7 times. After a 5N aqueous sodium hydroxide solution was added thereto for neutralization, sodium chloride was added, and extraction was performed four times with dichloromethane (6.2 L). Sodium sulfate was added to the organic layer for dehydration, followed by filtration. The filtrate was concentrated under reduced pressure to obtain the compound 9 as a pale yellow transparent liquid.

Compound 9
$^1$H-NMR (CDCl$_3$, internal standard TMS); δ (ppm):
1.44 (9H, s, —CH$_2$CH$_2$—COO—C(CH$_3$)$_3$),
2.50 (2H, t, —CH$_2$CH$_2$—COO—C(CH$_3$)$_3$),
3.1 (2H, t, H$_2$N—CH$_2$CH$_2$O—(CH$_2$CH$_2$O)$_7$—),
3.45-3.85 (32H, m, H$_2$N—CH$_2$CH$_2$O—(CH$_2$CH$_2$O)$_7$—CH$_2$CH$_2$—)
Yield: 1149 g (yield: 94%)

(Example 1-6, Step (F))

Synthesis of Compound 10 in which a in Formula (1) is 8

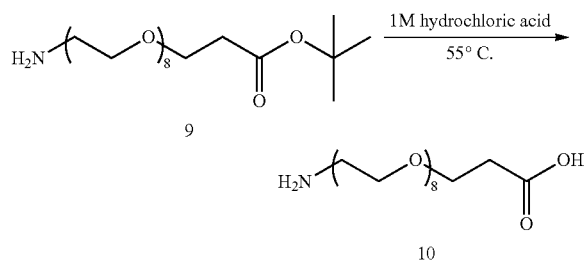

The compound 9 (850 g, 1.71 mol) and 1 M hydrochloric acid (4.2 L) were added to a reaction vessel fitted with a thermometer, a nitrogen inlet tube and a stirrer and the compound was dissolved, followed by stirring at 50 to 55° C. for 1 hour. After cooling to 15° C., the mixture was neutralized with a 10 M aqueous sodium hydroxide solution, and sodium chloride and dichloromethane (4.3 L) were added, followed by washing. Further, this aqueous layer was washed twice with dichloromethane (4.3 L), adjusted to pH 2 with 6M hydrochloric acid, and concentrated under reduced pressure. Dichloromethane (2.6 L) and ethanol (2.2 L) were added, and the mixture was stirred and filtered, followed by concentration under reduced pressure. Then, after the operation of adding dichloromethane (2.6 L) and concentrating under reduced pressure was repeated three times, dichloromethane (2.6 L) was added to dissolve the resultant, and the solution was filtered. The filtrate was concentrated under reduced pressure to obtain the compound 10 as a pale yellow transparent liquid.

Compound 10
$^1$H-NMR (CD$_3$OD internal standard TMS); δ (ppm):
2.56 (2H, t, —CH$_2$CH$_2$—COOH),
3.17 (2H, t, H$_2$N—CH$_2$CH$_2$O—),
3.6-3.9 (32H, m, —CH$_2$CH$_2$O—(CH$_2$CH$_2$O)$_7$—CH$_2$CH$_2$—)

Yield: 710 g (Yield: 87%)
Purity: 99.8% (HPLC-RI)
The HPLC measurement conditions used for the purity measurement are shown below.
Apparatus: alliance manufactured by Waters Corporation.
Column: Inertsil ODS-3 (column size: 4.6 mm×25 cm, particle size 5 μm) manufactured by GL Science Inc.
Detector: RI
Developing solvent: a solution of methanol/5 mM ammonium acetate solution=15/85
Flow rate: 1.0 mL/min
Column temperature: 40° C.
Sample concentration: 1 mg/mL
Injection volume: 50 μL Example 2

Synthesis of Compound 18 in which a in Formula (1) is 12

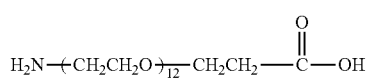

(18)

Example 2-1

Synthesis of Compound 11 in which a is 8, R$^1$ is Trityl Group, and L is Mesyl Group in Formula (3)

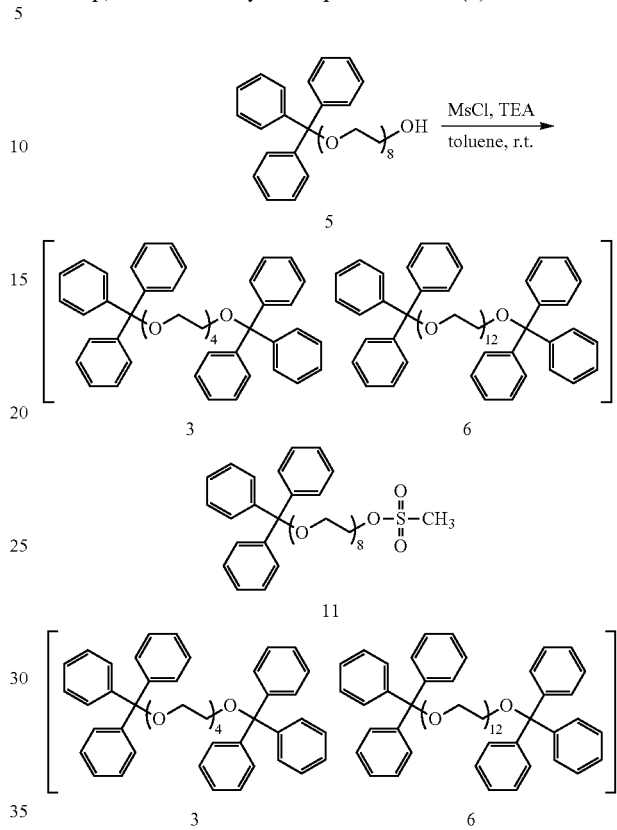

The reaction product containing the compound 5 (compound 5: 841 g, less than 1.37 mol) and toluene (4.2 L) were added to a reaction vessel fitted with a thermometer, a nitrogen inlet tube and a stirrer and the product was dissolved under a nitrogen atmosphere, followed by addition of triethylamine (267 ml, 1.92 mol). Methanesulfonyl chloride (128 mL, 1.65 mol) was added dropwise at 10° C., and the mixture was stirred at room temperature for 2 hours. After 2 hours, the disappearance of the compound 5 was confirmed by TLC analysis, a 5% aqueous sodium dihydrogen phosphate solution (4.2 L) was added, and liquid separation was performed. The organic layer was washed once with a 5% aqueous sodium dihydrogen phosphate solution (4.2 L), once with a saturated aqueous sodium hydrogen carbonate solution (4.2 L), and once with a saturated aqueous sodium chloride solution (4.2 L). Sodium sulfate was added to the organic layer for dehydration, followed by filtration. The filtrate was concentrated under reduced pressure to obtain a reaction product containing the compound 11 as a pale yellow transparent liquid. Moreover, it was confirmed from TLC analysis and $^1$H-NMR measurement results that the obtained reaction product contained the above compounds 3 and 6.

Compound 11
$^1$H-NMR (CDCl$_3$, internal standard TMS); δ (ppm):
3.07 (3H, s, —OCH$_2$CH$_2$—O—SO$_2$CH$_3$),
3.23 (2H, t, (C$_6$H$_5$)$_3$C—OCH$_2$CH$_2$—, including those derived from compounds 3 and 6) 3.45-3.85 (28H, m, —OCH$_2$CH$_2$—(OCH$_2$CH$_2$)$_6$—OCH$_2$CH$_2$—, including those derived from compounds 3 and 6), 4.37 (2H, t, —OCH$_2$CH$_2$—O—SO$_2$CH$_3$),
7.21-7.47 (15H, m, (C$_6$H$_5$)$_3$C—OCH$_2$CH$_2$—, including those derived from compounds 3 and 6)

Yield: 945 g

From the $^1$H-NMR measurement results of the compound 11 of Example 2-1, it was confirmed that the compounds 3 and 6 were contained in an amount of about 11 mol % (compound 3: 6 mol %, compound 6: 5 mol %, rough estimation).

A calculation expression of the contents of the compounds 3 and 6 on the basis of a δ 3.23 peak is expressed by the following expression.

(((2−[δ 4.32])/4H)/([δ 4.32]/2H))×100 (mol %)

With regard to the content of the compound 3, a value calculated in Example 1-1 is applied.

Further, the reaction product 5 used in Example 2-1 contains the compounds 3 and 6 in an amount of about 12.6 wt %.

(Example 2-2, Step (A)) Synthesis of Compound 12 in which a is 12 and R$^1$ is Trityl Group in Formula (4)

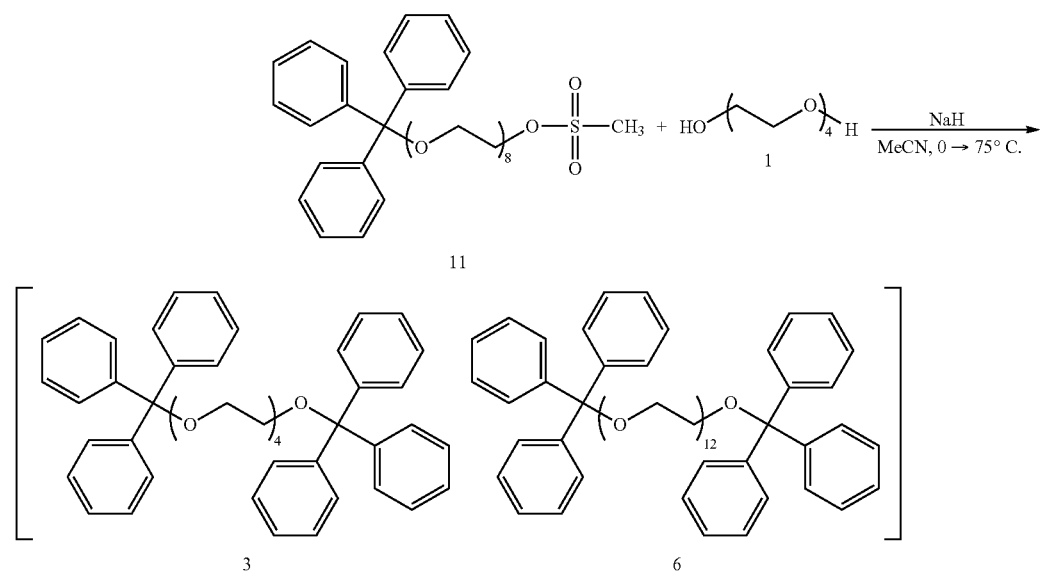

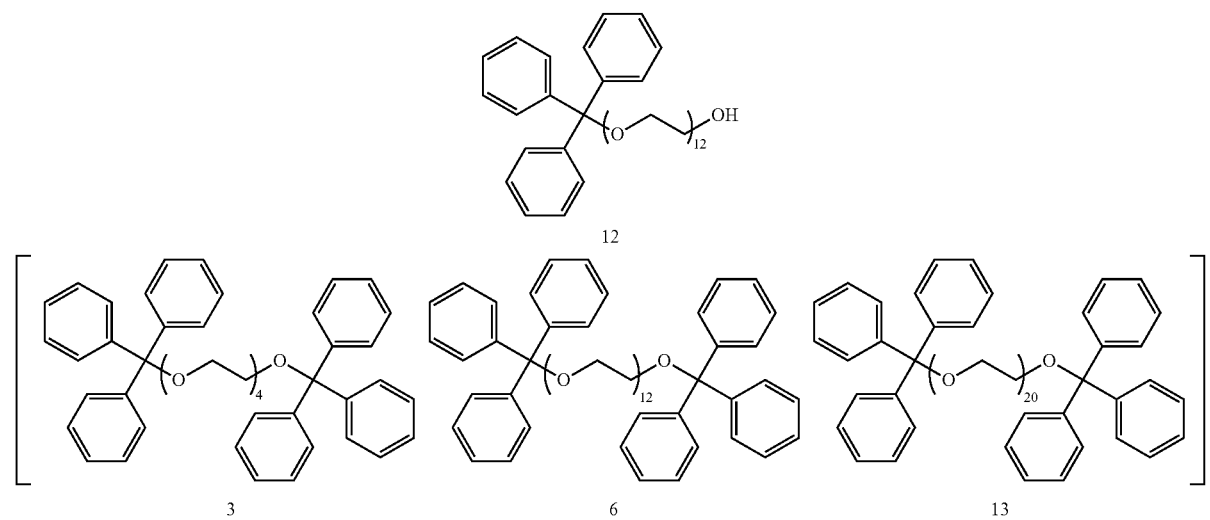

Sodium hydride (78 g) was placed in a reactor fitted with a thermometer, a nitrogen inlet tube and a stirrer, and after nitrogen substitution, MeCN (1.9 L) was added and the mixture was cooled to 0° C. MeCN (940 mL) was mixed with tetraethylene glycol 1 (1327 g, 6.83 mol) azeotropically dehydrated with toluene (660 mL), and this mixed solution was added dropwise over 2 hours. After completion of the dropwise addition, MeCN (940 mL) was mixed with the reaction product containing the compound 11 (compound 11: 944 g, less than 1.37 mol), and the mixed solution was added dropwise over 20 minutes. After completion of the dropwise addition, the reaction mixture was heated to 75° C. and stirred for 3 hours. After 3 hours, it was confirmed using $^1$H-NMR that the compound 11 had disappeared, and the mixture was allowed to cool until the temperature became 40° C. or lower. A saturated aqueous ammonium chloride solution (1.9 L) and hexane (1.4 L) were added to the reaction mixture solution and liquid separation was performed. The lower layer from which the hexane layer (upper layer) had been removed was concentrated under reduced pressure, and toluene (4.7 L) was added to the residue. This toluene solution was washed once with a saturated aqueous ammonium chloride solution (2.8 L) and three times with a saturated aqueous sodium chloride solution (4.7 L). Sodium sulfate was added to the organic layer for dehydration, followed by filtration. The filtrate was concentrated under reduced pressure to obtain a reaction product containing the compound 12 as a pale yellow transparent liquid. Moreover, it was confirmed from TLC analysis and $^1$H-NMR measurement results that the obtained reaction product contained the above compounds 3, 6 and 13.

Compound 12

$^1$H-NMR (CDCl$_3$, internal standard TMS); δ (ppm):
2.56 (1H, t, —C—(OCH$_2$CH$_2$)$_{12}$—OH),
3.23 (2H, t, (C$_6$H$_5$)$_3$C—OCH$_2$CH$_2$—, including those derived from compounds 3, 6 and 13)
3.45-3.85 (46H, m, —OCH$_2$CH$_2$—(OCH$_2$CH$_2$)$_{11}$—OH, including those derived from compounds 3, 6 and 13),
7.21-7.47 (15H, m, (C$_6$H$_5$)$_3$C—OCH$_2$CH$_2$—, including those derived from compounds 3, 6 and 13)

Yield: 1027 g (Example 2-3, Step (B))

Synthesis of Compound 14 in which a is 12, R$^1$ is Trityl Group, and R$^2$ is Tert-Butyl Group in Formula (6)

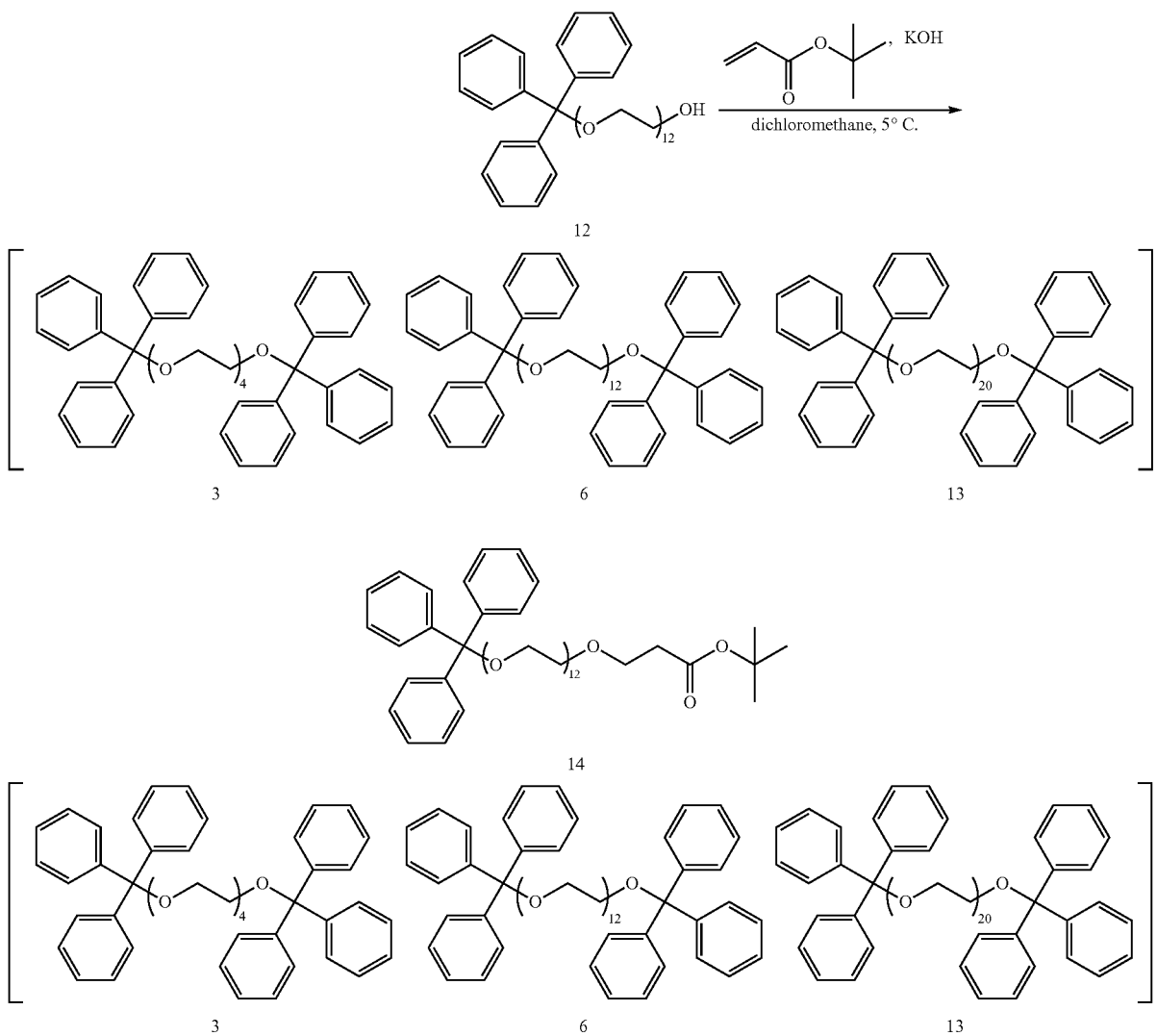

The reaction product containing the compound 12 (compound 12: 200 g, less than 253 mmol) and dichloromethane (1000 mL) were added to a reaction vessel fitted with a thermometer, a nitrogen inlet tube and a stirrer, and the product was dissolved under a nitrogen atmosphere, followed by addition of powdery potassium hydroxide (1.4 g, 25 mmol). After cooling to 5° C., tert-butyl acrylate (a compound in which $R^2$ in the formula (5) is a tert-butyl group, 55 mL, 380 mmol) was added dropwise, and the mixture was reacted at 5° C. for 2 hours. After the reaction, a saturated aqueous ammonium chloride solution (400 mL) was added and liquid separation was performed. The organic layer was washed once with a saturated aqueous sodium chloride solution (600 mL). The organic layer was concentrated under reduced pressure to obtain a reaction product containing the compound 14 as a pale yellow transparent liquid. Moreover, it was confirmed from TLC analysis and $^1$H-NMR measurement results that the obtained reaction product contained the above compounds 3, 6 and 13.

Compound 14
$^1$H-NMR (CDCl$_3$, internal standard TMS); δ (ppm):
1.44 (9H, s, —CH$_2$CH$_2$—COO—C(CH$_3$)$_3$),
2.49 (2H, t, —CH$_2$CH$_2$—COO—C(CH$_3$)$_3$),
3.23 (2H, t, (C$_6$H$_5$)$_3$C—OCH$_2$CH$_2$—, including those derived from compounds 3, 6 and 13),
3.45-3.85 (48H, m, —OCH$_2$CH$_2$—(OCH$_2$CH$_2$)$_{11}$—OCH$_2$CH$_2$—, including those derived from compounds 3, 6 and 13),
7.21-7.47 (15H, m, (C$_6$H$_5$)$_3$C—OCH$_2$CH$_2$—, including those derived from compounds 3, 6 and 13)
Yield: 226 g (Yield: 97%)

(Example 2-4, Steps (C), (D))

Synthesis of Compound 15 in which a is 12 and $R^2$ is Tert-Butyl Group in Formula (7)

A reaction product containing the compound 14 (compound 14: 226 g, less than 246 mmol) and methanol (1.1 L) were added to a reaction vessel fitted with a thermometer, a nitrogen inlet tube, and a stirrer, and the product was dissolved under a nitrogen atmosphere. Thereafter, p-toluenesulfonic acid monohydrate (23 g, 123 mmol) and hexane (900 mL) were added. After stirring at room temperature for 30 minutes, the hexane layer was removed, hexane (565 mL) was added again, and the mixture was stirred for 30 minutes. After performing the same operation four times, the disappearance of the compounds 14, 3, 6 and 13 was confirmed as a result of $^1$H-NMR measurement, and a saturated aqueous sodium hydrogen carbonate solution (452 mL) was added. The mixed solution was washed once with hexane (565 mL) to remove trityl methyl ether. The methanol solution was concentrated under reduced pressure to obtain a crude product containing the compound 15. It was confirmed from TLC analysis and $^1$H-NMR measurement results that the obtained crude product contained the above compounds 1, 9 and 16.

Next, dichloromethane (1.1 L) was added to the crude product, and the mixture was washed three times with ion-exchanged water (1.1 L) and once with a saturated aqueous sodium chloride solution (1.1 L) under the condition of 10° C. From TLC analysis, the disappearance of the compounds 1, 9 and 13 was confirmed. Magnesium sulfate was added to the organic layer for dehydration, followed by filtration. The filtrate was concentrated under reduced pressure to obtain a purified product containing the compound 15 as a pale yellow transparent liquid.

Compound 15
$^1$H-NMR (CDCl$_3$, internal standard TMS); δ (ppm):
1.44 (9H, s, —CH$_2$CH$_2$—COO—C(CH$_3$)$_3$),
2.50 (2H, t, —CH$_2$CH$_2$—COO—C(CH$_3$)$_3$),

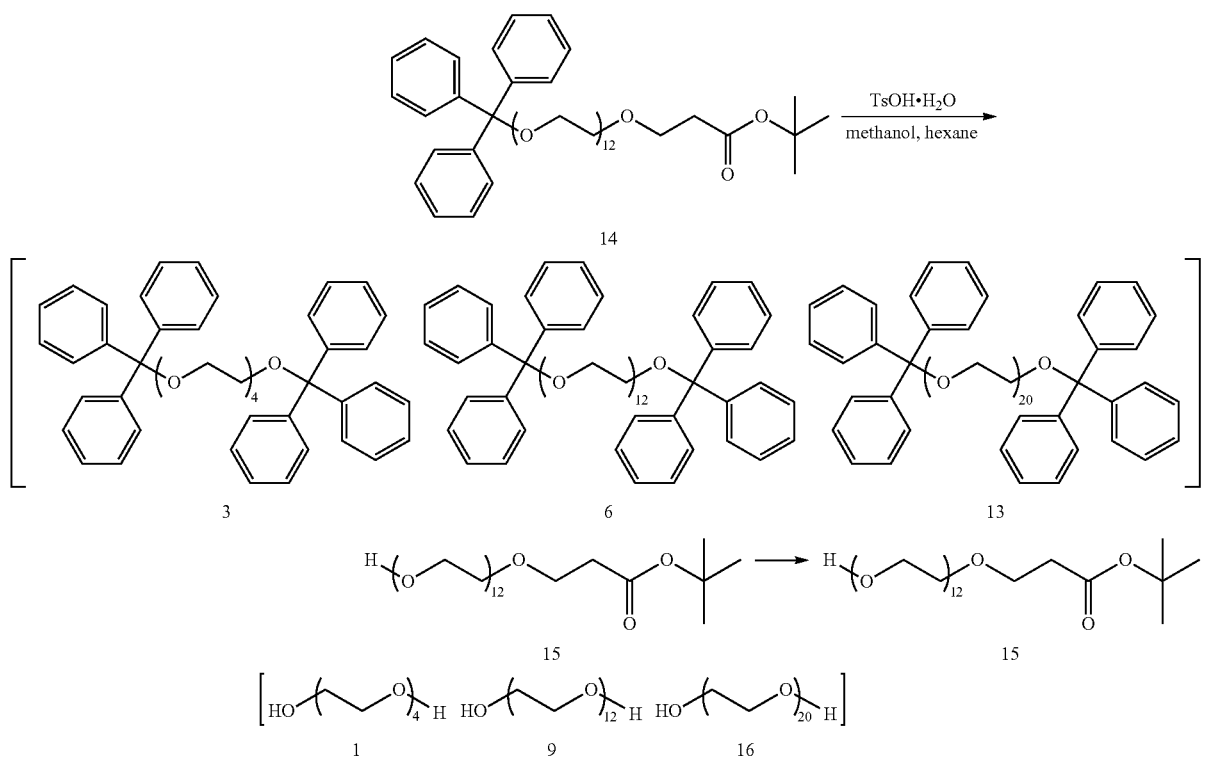

2.6 (1H, t, H—(OCH$_2$CH$_2$)$_{12}$—OCH$_2$CH$_2$—), 3.45-3.85 (50H, m, H—(OCH$_2$CH$_2$)$_{12}$—OCH$_2$CH$_2$—)

Yield: 118 g (yield: 71%)

(Example 2-5, Step (E))

Synthesis of Compound 17 in which a is 12 and R$^2$ is Tert-Butyl Group in Formula (8)

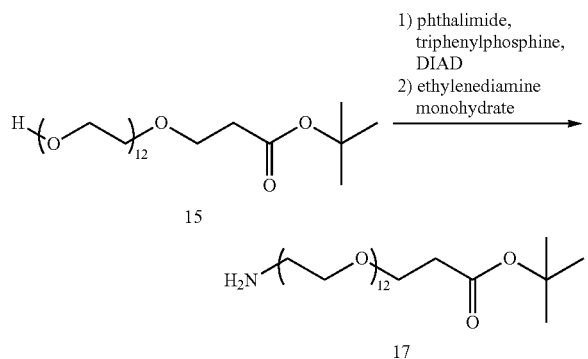

The compound 15 (117 g, 173 mmol) and dichloromethane (469 mL) were added to a reaction vessel fitted with a thermometer, a nitrogen inlet tube and a stirrer and the compound was dissolved under a nitrogen atmosphere. Then, phthalimide (36 g, 245 mmol) and triphenylphosphine (64 g, 244 mmol) were added. After stirring at room temperature for 30 minutes, diisopropyl azodicarboxylate (42 g, 208 mmol) diluted with dichloromethane (118 mL) was added dropwise, and the mixture was stirred for 1 hour. After 1 hour, the disappearance of the compound 15 was confirmed by TLC, the solvent was distilled off under reduced pressure, methanol (518 mL) and ethylenediamine monohydrate (141 mL, 1.73 mol) were added, and a reaction was carried out at 40° C. for 3 hours. A 6N aqueous hydrochloric acid solution was added thereto for neutralization, the solvent was distilled off under reduced pressure, sodium chloride and chloroform (585 mL) were added for extraction. A saturated aqueous sodium chloride solution (585 mL) was added to the resultant extract solution, and washing was performed twice. A 1% aqueous sodium dihydrogen phosphate solution (585 mL) was added to the organic layer, and the mixture was extracted four times. While a mixed solvent of chloroform (293 mL) and toluene (293 mL) was added to the extracted aqueous solution, washing was performed seven times. After a 5N aqueous sodium hydroxide solution was added thereto for neutralization, sodium chloride was added, and extraction was performed with dichloromethane (590 mL) four times. Sodium sulfate was added to the organic layer for dehydration, followed by filtration. The filtrate was concentrated under reduced pressure to obtain the compound 17 as a pale yellow transparent liquid.

Compound 17

$^1$H-NMR (CDCl$_3$, internal standard TMS); δ (ppm):

1.44 (9H, s, —CH$_2$CH$_2$—COO—C(CH$_3$)$_3$),
2.50 (2H, t, —CH$_2$CH$_2$—COO—C(CH$_3$)$_3$),
3.1 (2H, t, H$_2$N—CH$_2$CH$_2$O—(CH$_2$CH$_2$O)$_{11}$—),
3.45-3.85 (48H, m, H$_2$N—CH$_2$CH$_2$O—(CH$_2$CH$_2$O)$_{11}$—CH$_2$CH$_2$—)

Yield: 113 g (yield: 97%)

(Example 2-6, Step (F))

Synthesis of Compound 18 in which a in Formula (1) is 12

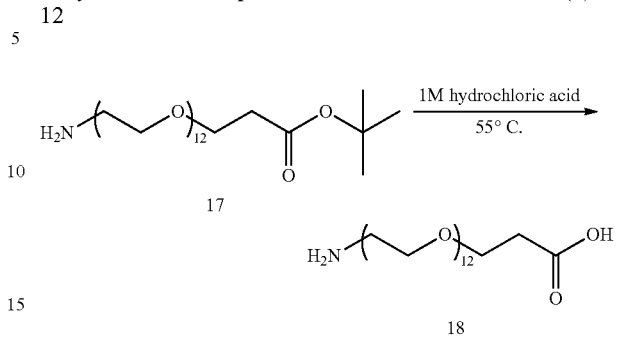

The compound 17 (50 g, 74 mmol) and 1 M hydrochloric acid (250 mL) were added to a reaction vessel fitted with a thermometer, a nitrogen inlet tube and a stirrer and the compound was dissolved, followed by stirring at 50 to 55° C. for 1 hour. After cooling to 15° C., the mixture was neutralized with a 10M aqueous sodium hydroxide solution, and sodium chloride and dichloromethane (250 mL) were added for washing. The aqueous layer was again washed once with dichloromethane (250 mL), adjusted to pH 2 with 6M hydrochloric acid, and extracted with dichloromethane (250 mL) four times. The recovered organic layers were mixed and dehydrated over sodium sulfate, followed by filtration. The filtrate was concentrated under reduced pressure to obtain the compound 18 as a pale yellow solid.

Compound 18

$^1$H-NMR (CD$_3$OD internal standard TMS); δ (ppm):

2.56 (2H, t, —CH$_2$CH$_2$—COOH),
3.17 (2H, t, H$_2$N—CH$_2$CH$_2$O—),
3.6-3.9 (48H, m, —CH$_2$CH$_2$O—(CH$_2$CH$_2$O)$_{11}$—CH$_2$CH$_2$—)

Yield: 44 g (Yield: 91%)

Purity: 99.8% (HPLC-RI)

The HPLC measurement conditions used for the purity measurement are shown below.

Apparatus: alliance manufactured by Waters Corporation.

Column: Inertsil ODS-3 (column size: 4.6 mm×25 cm, particle size 5 μm) manufactured by GL Science Inc.

Detector: RI

Developing solvent: a solution of methanol/5 mM ammonium acetate solution=27.5/72.5

Flow rate: 1.0 mL/min

Column temperature: 40° C.

Sample concentration: 2 mg/mL

Injection volume: 50 μL

Example 3

Synthesis of Compound 40 in which a is 24 in Formula (1)

(40)

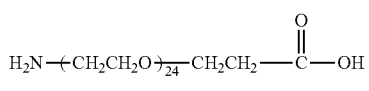

Example 3-1

Synthesis of Compound 19 in which a is 12, $R^1$ is Trityl Group, and L is Mesyl Group in Formula (3)

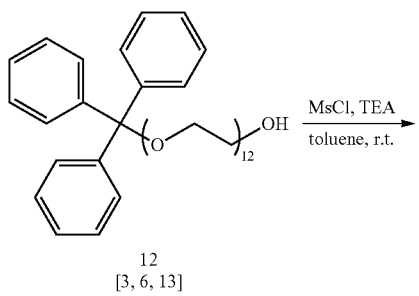

12
[3, 6, 13]

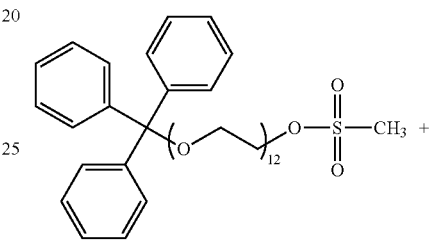

19
[3, 6, 13]

The reaction product containing the compound 12 (compound 12: 90 g, less than 0.11 mol) and toluene (451 mL) were added to a reaction vessel fitted with a thermometer, a nitrogen inlet tube and a stirrer and the product was dissolved under a nitrogen atmosphere, followed by addition of triethylamine (29 ml, 0.21 mol). Methanesulfonyl chloride (14 mL, 0.18 mol) was added dropwise at 10° C., and the mixture was stirred at room temperature for 2 hours. After 2 hours, the disappearance of the compound 12 was confirmed by TLC analysis, a 5% aqueous sodium dihydrogen phosphate solution (450 mL) was added, and liquid separation was performed. The organic layer was washed once with a 5% aqueous sodium dihydrogen phosphate solution (450 mL), twice with a saturated aqueous sodium hydrogen carbonate solution (450 mL), and once with a saturated aqueous sodium chloride solution (450 mL). Sodium sulfate was added to the organic layer for dehydration, followed by filtration. The filtrate was concentrated under reduced pressure to obtain a reaction product containing the compound 19 as a pale yellow transparent liquid. Moreover, it was confirmed from TLC analysis and $^1$H-NMR measurement results that the obtained reaction product contained the above compounds 3, 6 and 13.

Compound 19

$^1$H-NMR (CDCl$_3$, internal standard TMS); δ (ppm):
  3.07 (3H, s, —OCH$_2$CH$_2$—O—SO$_2$CH$_3$),
  3.23 (2H, t, (C$_6$H$_5$)$_3$C—OCH$_2$CH$_2$—, including those derived from compounds 3, 6 and 13)
  3.45-3.85 (44H, m, —OCH$_2$CH$_2$—(OCH$_2$CH$_2$)$_{10}$—OCH$_2$CH$_2$—, including those derived from compounds 3, 6 and 13),
  4.37 (2H, t, —OCH$_2$CH$_2$—O—SO$_2$CH$_3$),
  7.21-7.47 (15H, m, (C$_6$H$_5$)$_3$C—OCH$_2$CH$_2$—, including those derived from compounds 3, 6 and 13)

Yield: 96 g

From the $^1$H-NMR measurement results of the compound 19 of Example 3-1, it was confirmed that the compounds 3, 6 and 13 were contained in an amount of about 15 mol % (compound 3: 6 mol %, compound 6: 5 mol %, compound 13: 4 mol %, rough estimation).

A calculation expression of the content of the compounds 3, 6 and 13 on the basis of a δ 3.23 peak is expressed by the following expression.

(((2−[δ 4.32])/4H)/([δ 4.32]/2H))×100 (mol %)

With regard to the content of the compounds 3 and 6, values calculated in Example 1-1 and 2-1 are applied.

Further, the reaction product 12 used in Example 3-1 contains the compounds 3, 6 and 13 in an amount of about 15.9 wt %.

(Example 3-2, Step (A))

Synthesis of Compound 20 in which a is 16 and $R^1$ is Trityl Group in Formula (4)

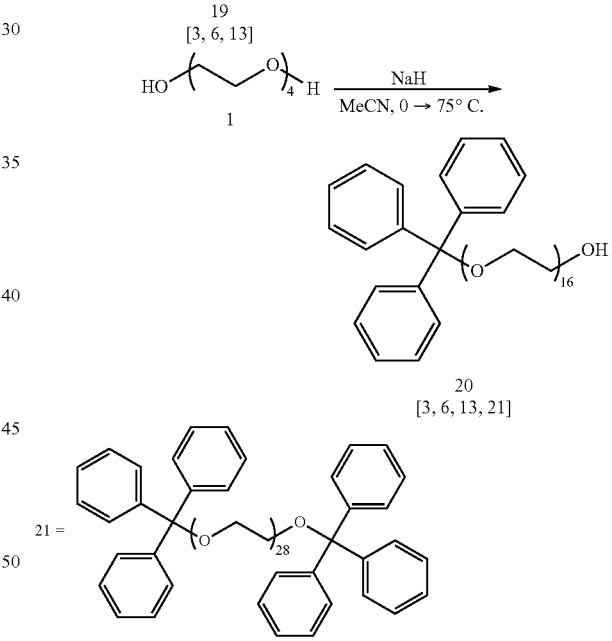

Sodium hydride (6.3 g) was placed in a reactor fitted with a thermometer, a nitrogen inlet tube and a stirrer. After nitrogen substitution, MeCN (192 mL) was added and the mixture was cooled to 0° C. MeCN (96 mL) was mixed with tetraethylene glycol 1 (108 g, 0.56 mol) azeotropically dehydrated with toluene (53 mL), and this mixed solution was added dropwise over 30 minutes. After completion of the dropwise addition, MeCN (96 mL) was mixed with the reaction product containing the compound 19 (compound 19: 96 g, less than 0.11 mol), and the mixed solution was added dropwise over 15 minutes. After completion of the dropwise addition, the reaction mixture was heated to 75° C. and stirred for 3 hours. After 3 hours, it was confirmed using ¹H-NMR that the compound 19 had disappeared, and the mixture was allowed to cool until the temperature became 40° C. or lower. A saturated aqueous ammonium chloride solution (170 mL) and hexane (146 mL) were added to the reaction mixture solution and liquid separation was performed. The lower layer from which the hexane layer (upper layer) had been removed was concentrated under reduced pressure, and toluene (481 mL) was added to the residue. The toluene solution was washed once with a saturated aqueous ammonium chloride solution (260 mL) and three times with a saturated aqueous sodium chloride solution (480 mL). Sodium sulfate was added to the organic layer for dehydration, followed by filtration. The filtrate was concentrated under reduced pressure to obtain a reaction product containing the compound 20 as a pale yellow transparent liquid. Moreover, it was confirmed from TLC analysis and ¹H-NMR measurement results that the obtained reaction product contained the above compounds 3, 6, 13 and 21.

Compound 20
¹H-NMR (CDCl₃, internal standard TMS); δ (ppm):
2.78 (1H, b, —C—(OCH₂CH₂)₁₆—OH),
3.23 (2H, t, (C₆H₅)₃C—OCH₂CH₂—, including those derived from compounds 3, 6, 13 and 21)
3.45-3.85 (62H, m, —OCH₂CH₂—(OCH₂CH₂)₁₅—OH, including those derived from compounds 3, 6, 13 and 21),
7.21-7.47 (15H, m, (C₆H₅)₃C—OCH₂CH₂—, including those derived from compounds 3, 6, 13 and 21)
Yield: 103 g Example 3-3

Synthesis of Compound 22 in which a is 16, R¹ is Trityl Group, and L is Mesyl Group in Formula (3)

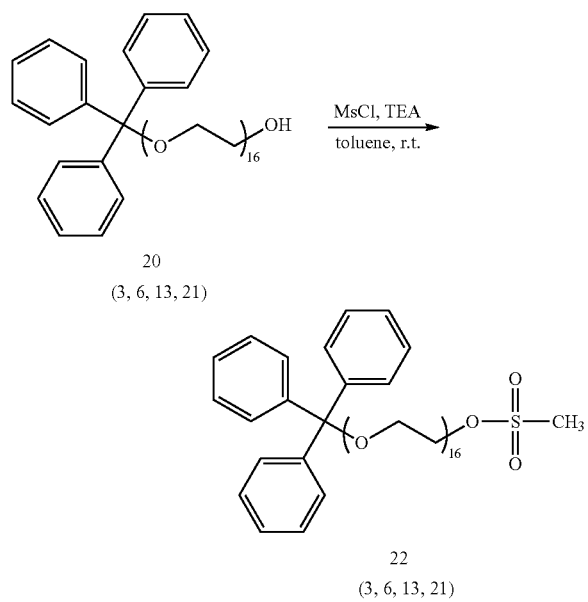

20
(3, 6, 13, 21)

22
(3, 6, 13, 21)

The reaction product containing the compound 20 (compound 20: 100 g, less than 0.10 mol) and toluene (500 mL) were added to a reaction vessel fitted with a thermometer, a nitrogen inlet tube and a stirrer and the product was dissolved under a nitrogen atmosphere, followed by addition of triethylamine (20 ml, 0.14 mol). Methanesulfonyl chloride (9.6 mL, 0.12 mol) was added dropwise at 10° C., and the mixture was stirred at room temperature for 2 hours. After 2 hours, the disappearance of the compound 14 was confirmed by TLC analysis, a 5% aqueous sodium dihydrogen phosphate solution (500 mL) was added, and liquid separation was performed. The organic layer was washed once with a 5% aqueous sodium dihydrogen phosphate solution (500 mL), twice with a saturated aqueous sodium hydrogen carbonate solution (500 mL), and once with a saturated aqueous sodium chloride solution (500 mL). Sodium sulfate was added to the organic layer for dehydration, followed by filtration. The filtrate was concentrated under reduced pressure to obtain a reaction product containing the compound 22 as a pale yellow transparent liquid. Moreover, it was confirmed from TLC analysis and ¹H-NMR measurement results that the obtained reaction product contained the above compounds 3, 6, 13 and 21.

Compound 22
¹H-NMR (CDCl₃, internal standard TMS); δ (ppm):
3.07 (3H, s, —OCH₂CH₂—O—SO₂CH₃),
3.23 (2H, t, (C₆H₅)₃C—OCH₂CH₂—, including those derived from compounds 3, 6, 13 and 21) 3.45-3.85 (60H, m, —OCH₂CH₂—(OCH₂CH₂)₁₄—OCH₂CH₂—, including those derived from compounds 3, 6, 13 and 21),
4.37 (2H, t, —OCH₂CH₂—O—SO₂CH₃),
7.21-7.47 (15H, m, (C₆H₅)₃C—OCH₂CH₂—, including those derived from compounds 3, 6, 13 and 21)
Yield: 106 g (Example 3-4, Step (A))

Synthesis of Compound 23 in which a is 20 and R¹ is Trityl Group in Formula (4)

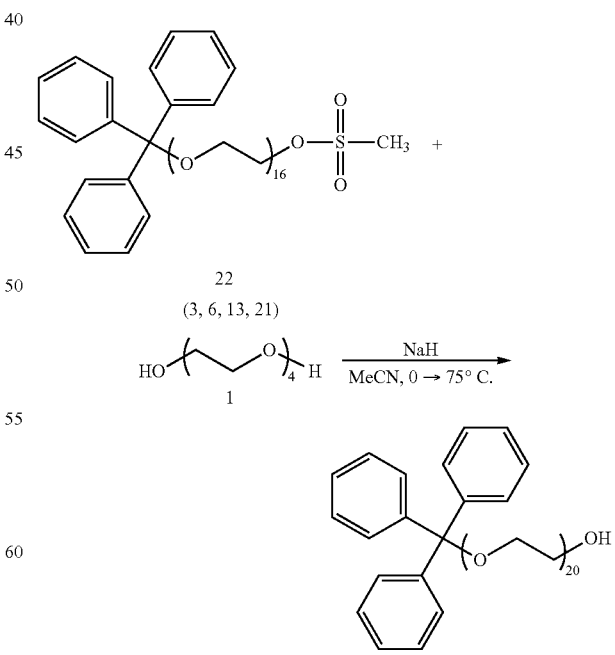

22
(3, 6, 13, 21)

23
(3, 6, 13, 21, 24)

24 =

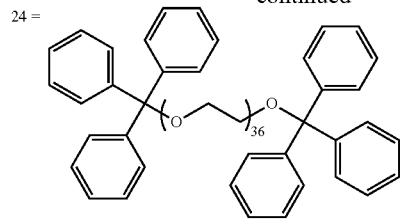

Sodium hydride (5.7 g) was placed in a reactor fitted with a thermometer, a nitrogen inlet tube and a stirrer, and after nitrogen substitution, MeCN (208 mL) was added and the mixture was cooled to 0° C. MeCN (105 mL) was mixed with tetraethylene glycol 1 (97 g, 0.50 mol) azeotropically dehydrated with toluene (48 mL), and this mixed solution was added dropwise over 30 minutes. After completion of the dropwise addition, MeCN (105 mL) was mixed with the reaction product containing the compound 22 (compound 22: 109 g, less than 0.10 mol), and the mixed solution was added dropwise over 15 minutes. After completion of the dropwise addition, the reaction mixture was heated to 75° C. and stirred for 3 hours. After 3 hours, it was confirmed using $^1$H-NMR that the compound 22 had disappeared, and the mixture was allowed to cool until the temperature became 40° C. or lower. A saturated aqueous ammonium chloride solution (190 mL) and hexane (159 mL) were added to the reaction mixture solution and liquid separation was performed. The lower layer from which the hexane layer (upper layer) had been removed was concentrated under reduced pressure, and toluene (524 mL) was added to the residue. This toluene solution was washed once with a saturated aqueous ammonium chloride solution (285 mL) and three times with a saturated aqueous sodium chloride solution (520 mL). Sodium sulfate was added to the organic layer for dehydration, followed by filtration. The filtrate was concentrated under reduced pressure to obtain a reaction product containing the compound 23 as a pale yellow transparent liquid. Moreover, it was confirmed from TLC analysis and $^1$H-NMR measurement results that the obtained reaction product contained the above compounds 3, 6, 13, 21 and 24.

Compound 22

$^1$H-NMR (CDCl$_3$, internal standard TMS); δ (ppm):
2.64 (1H, b, —C—(OCH$_2$CH$_2$)$_{20}$—OH),
3.23 (2H, t, (C-$_6$H$_5$)$_3$C—OCH$_2$CH$_2$—, including those derived from compounds 3, 6, 13, 21 and 24)
3.45-3.85 (78H, m, —OCH$_2$CH$_2$—(OCH$_2$CH$_2$)$_{19}$—OH, including those derived from compounds 3, 6, 13, 21 and 24),
7.21-7.47 (15H, m, (C$_6$H$_5$)$_3$C—OCH$_2$CH$_2$—, including those derived from compounds 3, 6, 13, 21 and 24)
Yield: 109 g

Example 3-5

Synthesis of Compound 25 in which a is 20, R$^1$ is Trityl Group, and L is Mesyl Group in Formula (3)

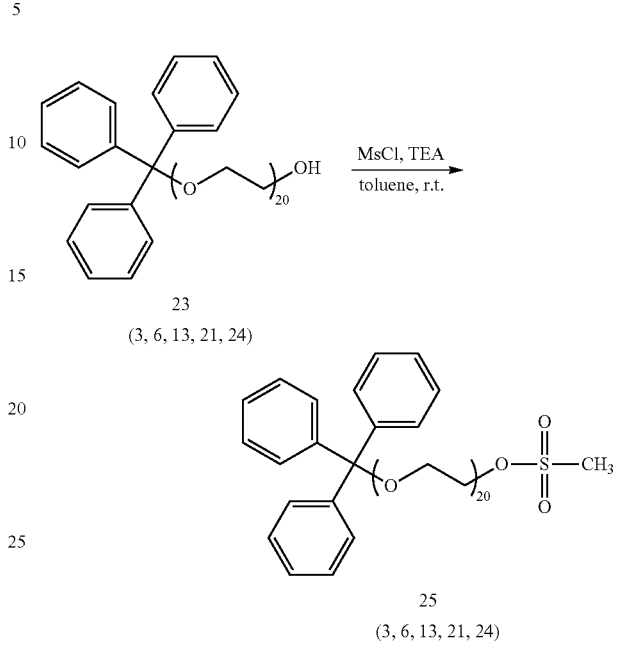

The reaction product containing the compound 23 (compound 23: 107 g, less than 0.094 mol) and toluene (585 mL) were added to a reaction vessel fitted with a thermometer, a nitrogen inlet tube and a stirrer and the product was dissolved under a nitrogen atmosphere, followed by addition of triethylamine (18 ml, 0.13 mol). Methanesulfonyl chloride (8.7 mL, 0.11 mol) was added dropwise at 10° C., and the mixture was stirred at room temperature for 2 hours. After 2 hours, the disappearance of the compound 14 was confirmed by TLC analysis, a 5% aqueous sodium dihydrogen phosphate solution (535 mL) was added, and liquid separation was performed. The organic layer was washed once with a 5% aqueous sodium dihydrogen phosphate solution (535 mL), twice with a saturated aqueous sodium hydrogen carbonate solution (535 mL), and once with a saturated aqueous sodium chloride solution (535 mL). Sodium sulfate was added to the organic layer for dehydration, followed by filtration. The filtrate was concentrated under reduced pressure to obtain a reaction product containing the compound 25 as a pale yellow transparent liquid. Moreover, it was confirmed from TLC analysis and $^1$H-NMR measurement results that the obtained reaction product contained the above compounds 3, 6, 13, 21 and 24.

Compound 25

$^1$H-NMR (CDCl$_3$, internal standard TMS); δ (ppm):
3.07 (3H, s, —OCH$_2$CH$_2$—O—SO$_2$CH$_3$),
3.23 (2H, t, (C$_6$H$_5$)$_3$C—OCH$_2$CH$_2$—, including those derived from compounds 3, 6, 13, 21 and 24)
3.45-3.85 (76H, m, —OCH$_2$CH$_2$—(OCH$_2$CH$_2$)$_{18}$—OCH$_2$CH$_2$—, including those derived from compounds 3, 6, 13, 21 and 24),
4.37 (2H, t, —OCH$_2$CH$_2$—O—SO$_2$CH$_3$),
7.21-7.47 (15H, m, (C$_6$H$_5$)$_3$C—OCH$_2$CH$_2$—, including those derived from compounds 3, 6, 13, 21 and 24)
Yield: 113 g (Example 3-6, Step (A))

Synthesis of Compound 26 in which a is 24 and $R^1$ is Trityl Group in Formula (4)

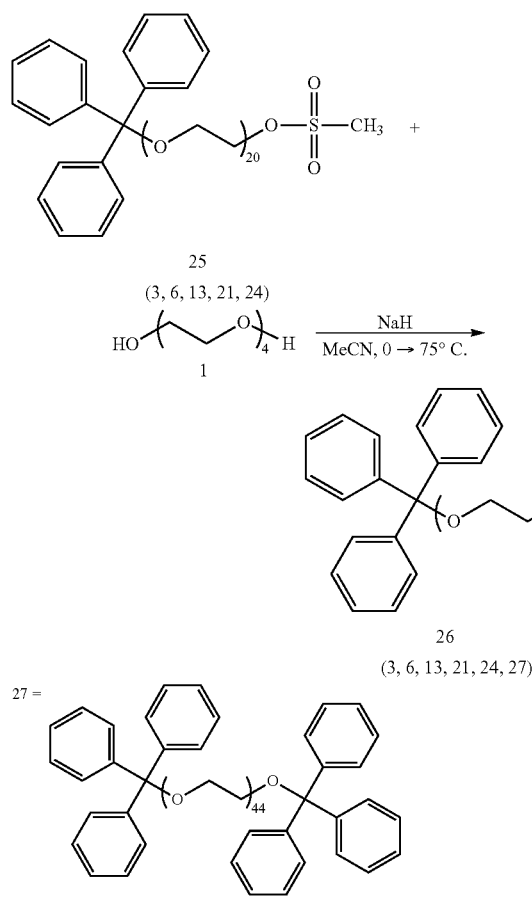

Sodium hydride (5.2 g) was placed in a reactor fitted with a thermometer, a nitrogen inlet tube and a stirrer, and after nitrogen substitution, MeCN (221 mL) was added and the mixture was cooled to 0° C. MeCN (111 mL) was mixed with tetraethylene glycol 1 (88 g, 0.46 mol) azeotropically dehydrated with toluene (44 mL), and this mixed solution was added dropwise over 30 minutes. After completion of the dropwise addition, MeCN (111 mL) was mixed with the reaction product containing the compound 25 (compound 25: 113 g, less than 0.092 mol), and the mixed solution was added dropwise over 15 minutes. After completion of the dropwise addition, the reaction mixture was heated to 75° C. and stirred for 3 hours. After 3 hours, it was confirmed using $^1$H-NMR that the compound 25 had disappeared, and the mixture was allowed to cool until the temperature became 40° C. or lower. A saturated aqueous ammonium chloride solution (200 mL) and hexane (168 mL) were added to the reaction mixture solution and liquid separation was performed. The lower layer from which the hexane layer (upper layer) had been removed was concentrated under reduced pressure, and toluene (556 mL) was added to the residue. The toluene solution was washed once with a saturated aqueous ammonium chloride solution (300 mL) and three times with a saturated aqueous sodium chloride solution (555 mL). Sodium sulfate was added to the organic layer for dehydration, followed by filtration. The filtrate was concentrated under reduced pressure to obtain a reaction product containing the compound 26 as a pale yellow transparent liquid. Moreover, it was confirmed from TLC analysis and $^1$H-NMR measurement results that the obtained reaction product contained the above compounds 3, 6, 13, 21, 24 and 27.

Compound 26
$^1$H-NMR (CDCl$_3$, internal standard TMS); δ (ppm):
2.66 (1H, b, —C—(OCH$_2$CH$_2$)$_{24}$—OH),
3.23 (2H, t, (C$_6$H$_5$)$_3$C—OCH$_2$CH$_2$—, including those derived from compounds 3, 6, 13, 21, 24 and 27)
3.45-3.85 (94H, m, —OCH$_2$CH$_2$—(OCH$_2$CH$_2$)$_{23}$—OH, including those derived from compounds 3, 6, 13, 21, 24 and 27),
7.21-7.47 (15H, m, (C$_6$H$_5$)$_3$C—OCH$_2$CH$_2$—, including those derived from compounds 3, 6, 13, 21, 24 and 27)
Yield: 115 g (Example 3-7, Step (B))

Synthesis of Compound 28 in which a is 24, $R^1$ is Trityl Group, and $R^2$ is Tert-Butyl Group in Formula (6)

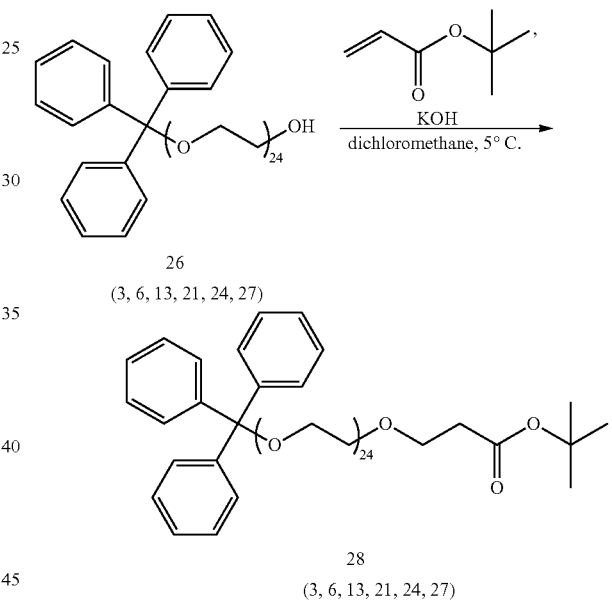

The reaction product containing the compound 28 (compound 28: 5.02 g, less than 3.79 mmol) and dichloromethane (25 mL) were added to a reaction vessel fitted with a thermometer, a nitrogen inlet tube and a stirrer, and the product was dissolved under a nitrogen atmosphere, followed by addition of powdery potassium hydroxide (128 mg, 2.28 mmol). After cooling to 5° C., tert-butyl acrylate (a compound in which $R^2$ in the formula (5) is a tert-butyl group, 1.1 mL, 7.58 mmol) was added dropwise, and the mixture was reacted at 5° C. for 4 hours. After the reaction, a saturated aqueous ammonium chloride solution (10 mL) was added and liquid separation was performed. The organic layer was washed once with a saturated aqueous sodium chloride solution (15 mL). The organic layer was concentrated under reduced pressure to obtain a reaction product containing the compound 28 as a pale yellow transparent liquid. Moreover, it was confirmed from TLC analysis and $^1$H-NMR measurement results that the obtained reaction product contained the above compounds 3, 6, 13, 21, 24 and 27.

Compound 28

$^1$H-NMR (CDCl$_3$, internal standard TMS); δ (ppm):
1.44 (9H, s, —CH$_2$CH$_2$—COO—C(CH$_3$)$_3$),
2.49 (2H, t, —CH$_2$CH$_2$—COO—C(CH$_3$)$_3$),
3.23 (2H, t, (C$_6$H$_5$)$_3$C—OCH$_2$CH$_2$—, including those derived from compounds 3, 6, 13, 21, 24 and 27),
3.45-3.85 (96H, m, —OCH$_2$CH$_2$—(OCH$_2$CH$_2$)$_{23}$—OCH$_2$CH$_2$—, including those derived from compounds 3, 6, 13, 21, 24 and 27),
7.21-7.47 (15H, m, (C$_6$H$_5$)$_3$C—OCH$_2$CH$_2$—, including those derived from compounds 3, 6, 13, 21, 24 and 27)
Yield: 5.31 g (Example 3-8, Step (C))

Synthesis of Compound 29 in which a is 24 and R$^2$ is Tert-Butyl Group in Formula (7)

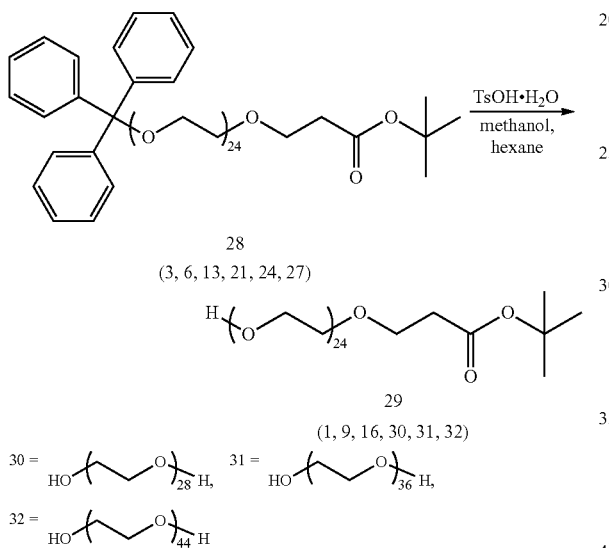

A reaction product containing the compound 28 (compound 28: 5.01 g, less than 3.46 mmol) and methanol (25 mL) were added to a reaction vessel fitted with a thermometer, a nitrogen inlet tube, and a stirrer, and the product was dissolved under a nitrogen atmosphere. Thereafter, p-toluenesulfonic acid monohydrate (329 mg, 1.72 mmol) and hexane (20 mL) were added. After stirring at room temperature for 30 minutes, the hexane layer was removed, hexane (13 mL) was added again, and the mixture was stirred for 30 minutes. After performing the same operation four times, the disappearance of the compounds 28, 3, 6, 13, 21, 24 and 27 was confirmed as a result of $^1$H-NMR measurement, and a saturated aqueous sodium hydrogen carbonate solution (11 mL) was added. The mixed solution was washed once with hexane (13 mL) to remove trityl methyl ether. The methanol solution was concentrated under reduced pressure and a 20% aqueous sodium chloride solution (10 mL) and dichloromethane (10 mL) were added, followed by liquid separation. Magnesium sulfate was added to the organic layer for dehydration, followed by filtration. The filtrate was concentrated under reduced pressure to obtain a reaction product containing the compound 29 as a pale yellow transparent liquid. Moreover, it was confirmed from TLC analysis and $^1$H-NMR measurement results that the obtained reaction product contained the above compounds 1, 9, 16 30, 31 and 32.

Compound 29

$^1$H-NMR (CDCl$_3$, internal standard TMS); δ (ppm):
1.44 (9H, s, —CH$_2$CH$_2$—COO—C(CH$_3$)$_3$),
2.50 (2H, t, —CH$_2$CH$_2$—COO—C(CH$_3$)$_3$),
2.7 (1H, b, H—(OCH$_2$CH$_2$)$_{24}$—OCH$_2$CH$_2$—),
3.45-3.85 (98H, m, H—(OCH$_2$CH$_2$)$_{24}$—OCH$_2$CH$_2$—, including those derived from compounds 1, 9, 16 30, 31 and 32)
Yield: 3.13 g (Example 3-9, Step (E))

Synthesis of Compound 33 in which a is 24 and R$^2$ is Tert-Butyl Group in Formula (8)

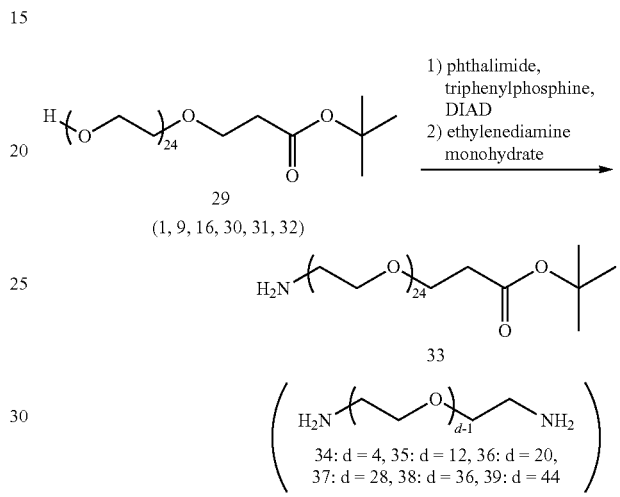

The reaction product containing the compound 29 (compound 29: 3.00 g, less than 2.49 mmol) and dichloromethane (12 mL) were added to a reaction vessel fitted with a thermometer, a nitrogen inlet tube and a stirrer and the product was dissolved under a nitrogen atmosphere. Then, phthalimide (641 mg, 4.36 mmol) and triphenylphosphine (1.14 g, 4.35 mmol) were added. After stirring at room temperature for 30 minutes, diisopropyl azodicarboxylate (756 mg, 3.74 mmol) diluted with dichloromethane (3 mL) was added dropwise, and the mixture was stirred for 3 hours. After 3 hours, the disappearance of the compound 29 was confirmed by TLC analysis, the solvent was distilled off under reduced pressure, methanol (13 mL) and ethylenediamine monohydrate (2 mL, 24.8 mol) were added, and a reaction was carried out at 40° C. for 4 hours. A 6N aqueous hydrochloric acid solution was added thereto for neutralization, the solvent was distilled off under reduced pressure, sodium chloride and chloroform (15 mL) were added for extraction, and while a saturated aqueous sodium chloride solution (15 mL) was added to the extract solution, washing was performed twice. A 1% aqueous sodium dihydrogen phosphate solution (15 mL) was added to this organic layer, and the mixture was extracted four times. While a mixed solvent of chloroform (8 mL) and toluene (8 mL) was added to the extracted aqueous solution, washing was performed seven times. After a 5N aqueous sodium hydroxide solution was added thereto for neutralization, sodium chloride was added, and extraction was performed four times with dichloromethane (15 mL). Sodium sulfate was added to the organic layer for dehydration, followed by filtration. The filtrate was concentrated under reduced pressure to obtain a reaction product containing the compound 33 as a pale yellow transparent liquid. Moreover, it was confirmed from TLC analysis and $^1$H-NMR measurement results that the obtained a reaction product contained the above compounds 34, 35, 36, 37, 38 and 39.

Compound 33
$^1$H-NMR (CDCl$_3$, internal standard TMS); δ (ppm):
1.44 (9H, s, —CH$_2$CH$_2$—COO—C(CH$_3$)$_3$),
2.50 (2H, t, —CH$_2$CH$_2$—COO—C(CH$_3$)$_3$),
3.1 (2H, t, H$_2$N—CH$_2$CH$_2$O—(CH$_2$CH$_2$O)$_{23}$—),
3.45-3.85 (96H, m, H$_2$N—CH$_2$CH$_2$O—(CH$_2$CH$_2$O)$_{23}$—CH$_2$CH$_2$—, including those derived from compounds 34, 35, 36, 37, 38 and 39)
Yield: 2.45 g (Example 3-10, Steps (F), (G))

Synthesis of Compound 40 in which a in Formula (1) is 24

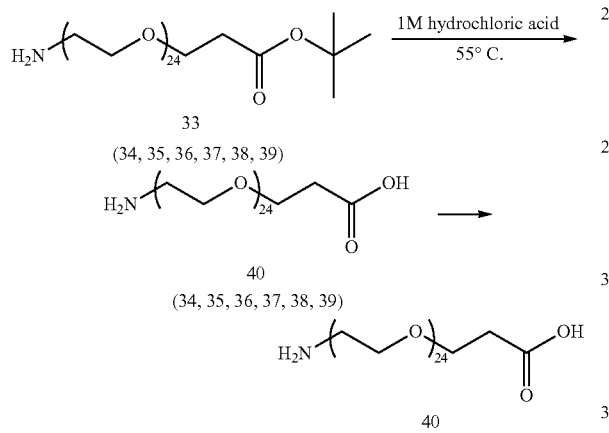

The reaction product containing the compound 33 (compound 33: 1.22 g, less than 1.00 mmol) and 1 M hydrochloric acid (6 mL) were added to a reaction vessel fitted with a thermometer, a nitrogen inlet tube and a stirrer and the product was dissolved, followed by stirring at 50 to 55° C. for 2 hours. After 2 hours, the disappearance of the compound 33 was confirmed by TLC. The mixture was cooled to room temperature.

Then, a 10M aqueous sodium hydroxide solution was added to the reaction solution to adjust the pH to 10, and while dichloromethane (6 mL) were added, washing was performed twice. The solution was adjusted to pH 2 with 6M hydrochloric acid, and after addition of sodium chloride, extraction was performed with dichloromethane (6 mL) three times. The recovered organic layers were mixed and dehydrated over sodium sulfate, followed by filtration. The filtrate was concentrated under reduced pressure to obtain the compound 40 (1.16 g) as a pale yellow oily solid. After tetrahydrofuran (5 mL) was added to the obtained compound 40 for dissolution, the solution was cooled to 10° C. and hexane (24 mL) cooled to 10° C. was added to effect crystallization. The crystals were collected by filtration and washed the crystals with hexane (10 mL) cooled to 10° C. The crystals were collected by filtration and dried under vacuum to obtain the compound 40 as white powdery crystals.

Compound 40
$^1$H-NMR (CD$_3$OD internal standard TMS); δ (ppm):
2.56 (2H, t, —CH$_2$CH$_2$—COOH),
3.17 (2H, t, H$_2$N—CH$_2$CH$_2$O—),
3.6-3.9 (96H, m, —CH$_2$CH$_2$O—(CH$_2$CH$_2$O)$_{23}$—CH$_2$CH$_2$—)
Yield: 893 mg Example 4

In order to calculate the content of the compound 5 in which a is 8 in the compound where R$^1$ in the formula (4) is a trityl group when the content of the compound having trityl groups at both terminals is removed from the reaction product containing the compound 5 obtained in Example 1-2, derivatization of the compound 42 was performed.

Synthesis of Compound 41 in which a is 8, R$^1$ is Trityl Group, and L is Tosyl Group in Formula (3)

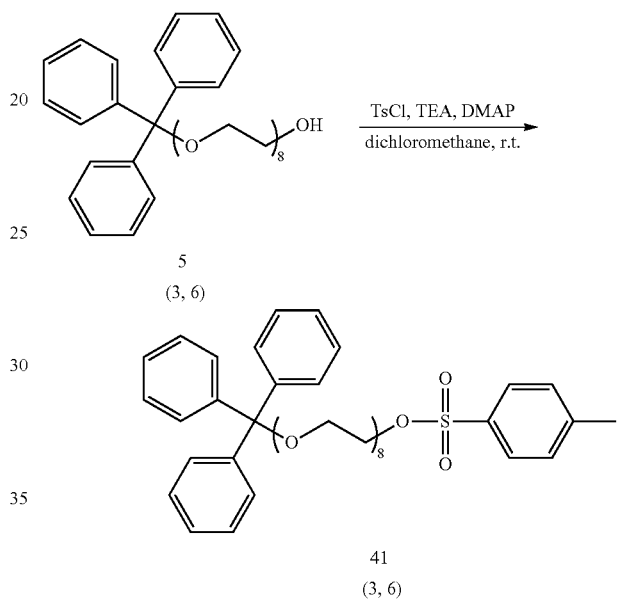

After the reaction product containing the compound 5 (compound 5: 5 g, less than 8.2 mmol) and dichloromethane (25 mL) was added to a reaction vessel fitted with a thermometer, a nitrogen inlet tube and a stirrer, and the product was dissolved under a nitrogen atmosphere, triethylamine (1.2 mL, 8.6 mmol), 4-dimethylaminopyridine (100 mg, 0.82 mmol) and TsCl (1.4 g, 7.3 mmol) were added, and the mixture was stirred at room temperature for 4 hours. After 4 hours, the disappearance of TsCl was confirmed by $^1$H-NMR analysis, a 1M aqueous hydrochloric acid solution (25 mL) was added, and liquid separation was performed. The organic layer was washed once with a 1M aqueous hydrochloric acid solution (25 mL), twice with a saturated aqueous sodium hydrogen carbonate solution (25 mL), and once with a saturated aqueous sodium chloride solution (25 mL). Sodium sulfate was added to the organic layer for dehydration, followed by filtration. The filtrate was concentrated under reduced pressure to obtain a reaction product containing compound 41 as a pale yellow transparent liquid. Moreover, it was confirmed from TLC analysis and the $^1$H-NMR measurement results that the obtained reaction products contained the above compounds 3 and 6.

Compound 41
$^1$H-NMR (CDCl$_3$, internal standard TMS); δ (ppm):
2.45 (3H, s, —OSO$_2$-Ph-CH$_3$),
3.23 (2H, t, (C$_6$H$_5$)$_3$C—OCH$_2$CH$_2$—, including those derived from compounds 3 and 6), 3.45-3.85 (28H, m, —OCH$_2$CH$_2$—(OCH$_2$CH$_2$)$_6$—OCH$_2$CH$_2$—, including those derived from compounds 3 and 6),
4.16 (2H, t, —OCH$_2$CH$_2$—OSO$_2$-Ph-CH$_3$),
7.21-7.47 (15H, m, (C$_6$H$_5$)$_3$C—OCH$_2$CH$_2$—, including those derived from compounds 3 and 6),
7.35 (2H, d, —OSO$_2$-Ph-CH$_3$),
7.80 (2H, d, —OSO$_2$-Ph-CH$_3$)
Yield: 6.1 g Synthesis of Compound 42 Having Ethylene Glycol Chain Length of 8 Units Having Hydroxyl Group at One Terminal and Tosyl Group at One Terminal

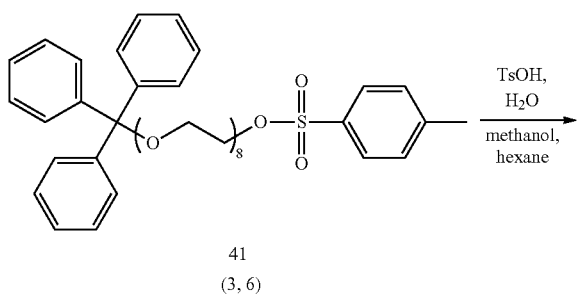

Next, the reaction product containing compound 42 (compound 42: 6.1 g, less than 8.0 mmol) and methanol (25 mL) were added to a reaction vessel fitted with a thermometer, a nitrogen inlet tube and a stirrer. After the compound was dissolved under a nitrogen atmosphere, p-toluenesulfonic acid monohydrate (0.78 g, 4.1 mmol) and hexane (20 mL) were added. After stirring at room temperature for 30 minutes, the hexane layer was removed, hexane (13 mL) was added again, and the mixture was stirred for 30 minutes. After performing the same operation six times, the disappearance of the compounds 42, 3 and 6 was confirmed as a result of $^1$H-NMR measurement, and a saturated aqueous sodium hydrogen carbonate solution (10 mL) was added. The mixed solution was washed twice with hexane (13 mL) to remove trityl methyl ether. The methanol solution was concentrated under reduced pressure, and dichloromethane (25 mL) was added for extraction. Magnesium sulfate was added to the organic layer for dehydration, followed by filtration. The filtrate was concentrated under reduced pressure to obtain the compound 42 as a pale yellow transparent liquid.

Compound 42
$^1$H-NMR (CDCl$_3$, internal standard TMS); δ (ppm):
2.45 (3H, s, —OSO$_2$-Ph-CH$_3$),
2.73 (1H, t, H—(OCH$_2$CH$_2$)$_8$—),
3.45-3.85 (30H, m, —(OCH$_2$CH$_2$)$_7$—OCH$_2$CH$_2$—),
4.16 (2H, t, —(OCH$_2$CH$_2$)$_7$—OCH$_2$CH$_2$—OSO$_2$-Ph-CH$_3$),
7.35 (2H, d, —OSO$_2$-Ph-CH$_3$),
7.80 (2H, d, —OSO$_2$-Ph-CH$_3$)
Yield: 3.0 g
Purity: 99.7% (HPLC-RI)

The HPLC measurement conditions used for the purity measurement are shown below.
Apparatus: alliance manufactured by Waters Corporation.
Column: Inertsil ODS-3 (column size: 4.6 mm×25 cm, particle size 5 μm) manufactured by GL Science Inc.
Detector: RI
Developing solvent: a solution of methanol/5 mM ammonium acetate=50/50
Flow rate: 0.6 mL/min
Column temperature: 40° C.
Sample concentration: 0.2 mg/mL
Injection volume: 40 μL
The purity value is the ratio of the peak area of the compound 43 to the total peak area detected over a retention time of 10 to 40 min.

Example 5

In order to calculate the content of compound 12 in which a is 12 in the compound where R$^1$ in the formula (4) is a trityl group when the content of the compound having trityl groups at both terminals is removed from the reaction product containing the compound 12 obtained in Example 2-2, derivatization of the compound 44 was performed.

Synthesis of Compound 43 in which a is 12, R$^1$ is Trityl Group, and L is Tosyl Group in Formula (3)

After the reaction product containing compound 12 (compound 12: 5 g, less than 6.3 mmol) and dichloromethane (25 mL) was added to a reaction vessel fitted with a thermometer, a nitrogen inlet tube and a stirrer, and the product was dissolved under a nitrogen atmosphere, triethylamine (0.93 mL, 6.6 mmol), 4-dimethylaminopyridine (77 mg, 0.63 mmol) and TsCl (0.97 g, 5.4 mmol) were added, and the mixture was stirred at room temperature for 4 hours. After 4 hours, the disappearance of TsCl was confirmed by $^1$H-NMR analysis, a 1M aqueous hydrochloric acid solution (25 mL) was added, and liquid separation was performed. The organic layer was washed once with a 1M aqueous hydrochloric acid solution (25 mL), twice with a saturated aqueous sodium hydrogen carbonate solution (25 mL), and once with a saturated aqueous sodium chloride solution (25 mL). Sodium sulfate was added to the organic layer for dehydration, followed by filtration. The filtrate was concentrated under reduced pressure to obtain a reaction product containing compound 43 as a pale yellow transparent liquid. Moreover, it was confirmed from TLC analysis and the $^1$H-NMR measurement results that the obtained reaction product contained the above compounds 3, 6 and 13.

Compound 43

$^1$H-NMR (CDCl$_3$, internal standard TMS); δ (ppm):
2.45 (3H, s, —OSO$_2$-Ph-CH$_3$),
3.23 (2H, t, (C$_6$H$_5$)$_3$C—OCH$_2$CH$_2$—, including those derived from compounds 3, 6 and 13),
3.45-3.85 (44H, m, —OCH$_2$CH$_2$—(OCH$_2$CH$_2$)$_{10}$—OCH$_2$CH$_2$—, including those derived from compounds 3, 6 and 13),
4.16 (2H, t, —OCH$_2$CH$_2$—OSO$_2$-Ph-CH$_3$),
7.21-7.47 (15H, m, (C$_6$H$_5$)$_3$C—OCH$_2$CH$_2$—, including those derived from compounds 3, 6 and 13),
7.35 (2H, d, —OSO$_2$-Ph-CH$_3$),
7.80 (2H, d, —OSO$_2$-Ph-CH$_3$)
Yield: 6.1 g

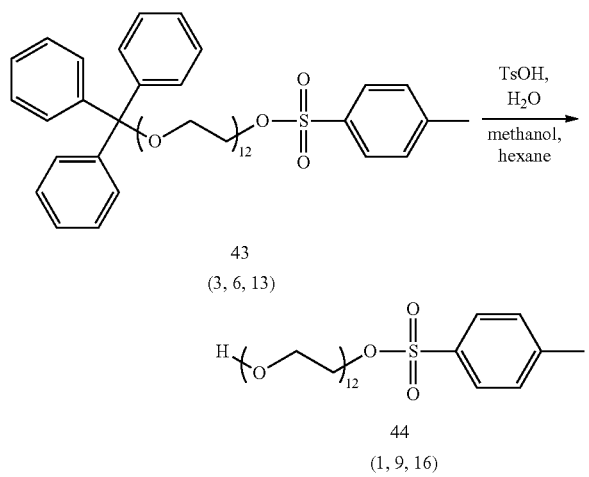

Next, the reaction product containing the compound 43 (compound 43: 6.1 g, less than 6.5 mmol) and methanol (25 mL) were added to a reaction vessel fitted with a thermometer, a nitrogen inlet tube and a stirrer. After the compound was dissolved under a nitrogen atmosphere, p-toluenesulfonic acid monohydrate (0.60 g, 3.2 mmol) and hexane (20 mL) were added. After stirring at room temperature for 30 minutes, the hexane layer was removed, hexane (13 mL) was added again, and the mixture was stirred for 30 minutes. After performing the same operation six times, the disappearance of the compounds 43, 3, 6 and 13 was confirmed as a result of $^1$H-NMR measurement, and a saturated aqueous sodium hydrogen carbonate solution (10 mL) was added. The mixed solution was washed twice with hexane (13 mL) to remove trityl methyl ether. The methanol solution was concentrated under reduced pressure and dichloromethane (25 mL) was added, followed by extraction. Magnesium sulfate was added to the organic layer for dehydration, followed by filtration. The filtrate was concentrated under reduced pressure to obtain the compound 44 as a pale yellow transparent liquid.

Compound 44

$^1$H-NMR (CDCl$_3$, internal standard TMS); δ (ppm):
2.45 (3H, s, —OSO$_2$-Ph-CH$_3$),
2.73 (1H, t, H—(OCH$_2$CH$_2$)$_8$—),
3.45-3.85 (46H, m, —(OCH$_2$CH$_2$)$_{11}$—OCH$_2$CH$_2$—),
4.16 (2H, t, —(OCH$_2$CH$_2$)$_7$—OCH$_2$CH$_2$—OSO$_2$-Ph-CH$_3$),
7.35 (2H, d, —OSO$_2$-Ph-CH$_3$),
7.80 (2H, d, —OSO$_2$-Ph-CH$_3$)
Yield: 3.3 g
Purity: 99.7% (HPLC-RI)

The HPLC measurement conditions used for the purity measurement are shown below.

Apparatus: alliance manufactured by Waters Corporation.
Column: Inertsil ODS-3 (column size: 4.6 mm×25 cm, particle size 5 μm) manufactured by GL Science Inc.
Detector: RI
Developing solvent: a solution of methanol/5 mM ammonium acetate=55/45
Flow rate: 0.6 mL/min
Column temperature: 40° C.
Sample concentration: 0.2 mg/mL
Injection volume: 40 μL The purity value is the ratio of the peak area of the compound 44 to the total peak area detected over a retention time of 11 to 40 min.

Comparative Example 1, Production Method for Obtaining Compound 10 Via Tosylation Step A compound 10 in which a is 8 in the formula (1) was synthesized by the production method described in Patent Literature 4.

Comparative Example 1-1

Synthesis of Compound 41 in which a is 4, R$^1$ is Trityl Group, and L is Tosyl Group in Formula (3)

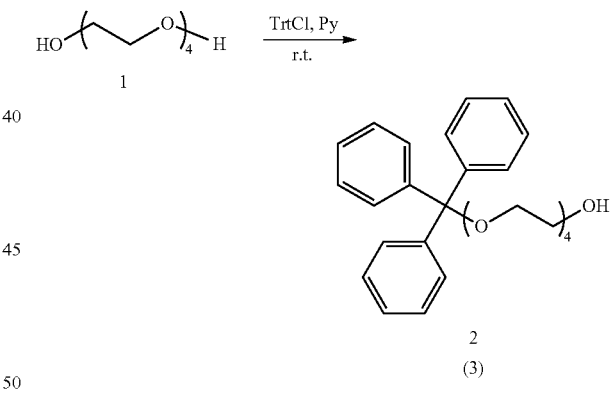

Tetraethylene glycol 1 (200 mL, 1.15 mol) and toluene (50 mL) were added to a reactor fitted with a thermometer, a nitrogen inlet tube and a stirrer, and the compound was dissolved under a nitrogen atmosphere and then azeotropically dehydrated at 110 to 120° C. After the azeotropic dehydration, the mixture was cooled, pyridine (18 ml, 0.22 mol) and trityl chloride (TrtCl, 40 g, 0.14 mol) were added, and the mixture was stirred at room temperature for 3 hours. After 3 hours, the disappearance of TrtCl was confirmed using TLC, and ion-exchanged water (200 mL) was added. Toluene (100 mL) was added to the obtained mixed solution, liquid separation was performed, and the organic layer was washed once with a mixed solution of ion-exchanged water (80 mL) and a saturated aqueous sodium chloride solution (20 mL), once with a 1M aqueous hydrochloric acid solution (50 mL), and four times with a saturated aqueous sodium chloride solution (50 mL). Sodium sulfate was added to the obtained organic layer, which was dried and filtered. Toluene (50 mL) was added to the filtrate, and azeotropic dehydration was performed three times to obtain a reaction product containing the compound 2 as a pale yellow transparent liquid. Moreover, it was confirmed by ESI-MS measurement that the obtained reaction product contained the above compound 3.

Compound 2
$^1$H-NMR (CDCl$_3$, internal standard TMS); δ (ppm):
2.4 (1H, t, —C—(OCH$_2$CH$_2$)$_4$—OH),
3.23 (2H, t, (C$_6$H$_5$)$_3$C—OCH$_2$CH$_2$—, including one derived from compound 3),
3.45-3.85 (14H, m, —OCH$_2$CH$_2$—(OCH$_2$CH$_2$)$_3$—OH, including one derived from compound 3),
7.21-7.47 (15H, m, (C$_6$H$_5$)$_3$C—OCH$_2$CH$_2$—, including one derived from compound 3)
MS (ESI$^+$): Compound 2 454.5 [M+NH$_4$]$^+$, Compound 3 696.9 [M+NH$_4$]$^+$
Yield: 63.8 g

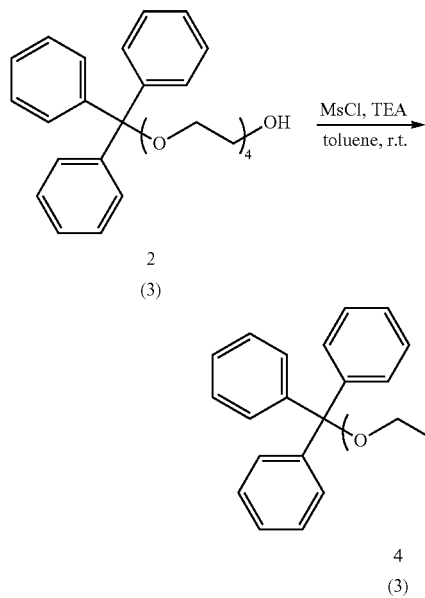

Next, the reaction product containing compound 2 (compound 2: 62.8 g, less than 0.14 mol) and toluene (314 mL) were added to a reaction vessel fitted with a thermometer, a nitrogen inlet tube and a stirrer. After dissolution under a nitrogen atmosphere, triethylamine (24 mL, 0.17 mol) was added. Methanesulfonyl chloride (12.2 mL, 0.16 mol) was added dropwise at 10° C., and the mixture was stirred at room temperature for 2 hours. After 2 hours, the disappearance of the compound 2 was confirmed by TLC analysis, and a 1M aqueous hydrochloric acid solution (314 mL) was added, followed by liquid separation. The organic layer was washed once with a 1M aqueous hydrochloric acid solution (314 mL), twice with a saturated aqueous sodium hydrogen carbonate solution (314 mL), and once with a saturated aqueous sodium chloride solution (314 mL). Sodium sulfate was added to the organic layer for dehydration, followed by filtration. The filtrate was concentrated under reduced pressure to obtain a reaction product containing the compound 4 as a pale yellow transparent liquid. Moreover, it was confirmed by ESI-MS measurement that the obtained reaction product contained the above compound 3.

Compound 4
$^1$H-NMR (CDCl$_3$, internal standard TMS); δ (ppm):
2.98 (3H, s, —OCH$_2$CH$_2$—O—SO$_2$CH$_3$),
3.23 (2H, t, (C$_6$H$_5$)$_3$C—OCH$_2$CH$_2$—, including one derived from compound 3),
3.45-3.85 (12H, m, —OCH$_2$CH$_2$—(OCH$_2$CH$_2$)$_2$—OCH$_2$CH$_2$—, including one derived from compound 3)
4.33 (2H, t, —OCH$_2$CH$_2$—O—SO$_2$CH$_3$),
7.21-7.47 (15H, m, (C$_6$H$_5$)$_3$C—OCH$_2$CH$_2$—, including one derived from compound 3)
MS (ESI$^+$): Compound 4 532.4 [M+NH$_4$]$^+$, Compound 3 696.8 [M+NH$_4$]$^+$
Yield: 70.4 g From $^1$H-NMR measurement results of the compound 4 of Comparative Example 1-1, it was confirmed that the compound 3 was contained in an amount of about 4.8 mol %.

A calculation expression of the compound 3 content on the basis of a δ 3.23 peak is expressed by the following expression.

$$(((2-[δ 4.32])/4H)/([δ 4.32]/2H))\times100 \text{ (mol \%)}$$

Further, the reaction product 2 obtained in Comparative Example 1-1 contains the compound 3 in an amount of about 6.9 wt %.

Comparative Example 1-2

Synthesis of compound 5 in which a is 8 and R$^1$ is trityl group in formula (4)

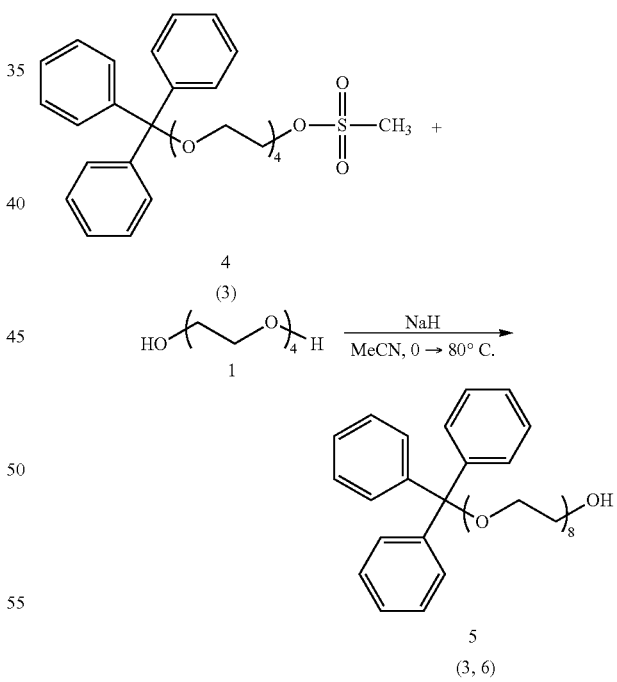

Sodium hydride (7.8 g) was placed in a reactor fitted with a thermometer, a nitrogen inlet tube and a stirrer, and after nitrogen substitution, MeCN (141 mL) was added and the mixture was cooled to 0° C. MeCN (70 mL) was mixed with tetraethylene glycol 1 (213 g, 1.10 mol) azeotropically dehydrated with toluene (107 mL), and this mixed solution was added dropwise over 30 minutes. After completion of the dropwise addition, MeCN (70 mL) was mixed with the reaction product containing the compound 4 (compound 4: 70.4 g, less than 0.14 mol), and the mixed solution was added dropwise over 15 minutes. After completion of the dropwise addition, the reaction mixture was heated to 80° C. and stirred for 3 hours. After 3 hours, it was confirmed using $^1$H-NMR that the compound 4 had disappeared, and the mixture was allowed to cool until the temperature became 40° C. or lower. The reaction mixture solution was concentrated under reduced pressure, and toluene (352 mL) was added to the residue. The toluene solution was washed twice with a saturated aqueous ammonium chloride solution (352 mL) and three times with a saturated aqueous sodium chloride solution (352 mL). Sodium sulfate was added to the organic layer for dehydration, followed by filtration. The filtrate was concentrated under reduced pressure to obtain a reaction product containing the compound 5 as a pale yellow transparent liquid. Moreover, it was confirmed from ESI-MS measurement that the obtained reaction products also contained the above compounds 3 and 6.

Compound 5

$^1$H-NMR (CDCl$_3$, internal standard TMS); δ (ppm):
2.52 (1H, t, —C—(OCH$_2$CH$_2$)$_8$—OH),
3.23 (2H, t, (C$_6$H$_5$)$_3$C—OCH$_2$CH$_2$—, including those derived from compounds 3 and 6)
3.45-3.85 (30H, m, —OCH$_2$CH$_2$—(OCH$_2$CH$_2$)$_7$—OH, including those derived from compounds 3 and 6),
7.21-7.47 (15H, m, (C$_6$H$_5$)$_3$C—OCH$_2$CH$_2$—, including those derived from compounds 3 and 6)
MS (ESI$^+$): Compound 5 630.8 [M+NH$_4$]$^+$, Compound 3 696.8 [M+NH$_4$]$^+$, Compound 6 1048.4 [M+NH$_4$]$^+$
Yield: 82.4 g Comparative Example 1-3

Synthesis of Compound 41 in which a is 8, R$^1$ is Trityl Group, and L is Tosyl Group in Formula (3)

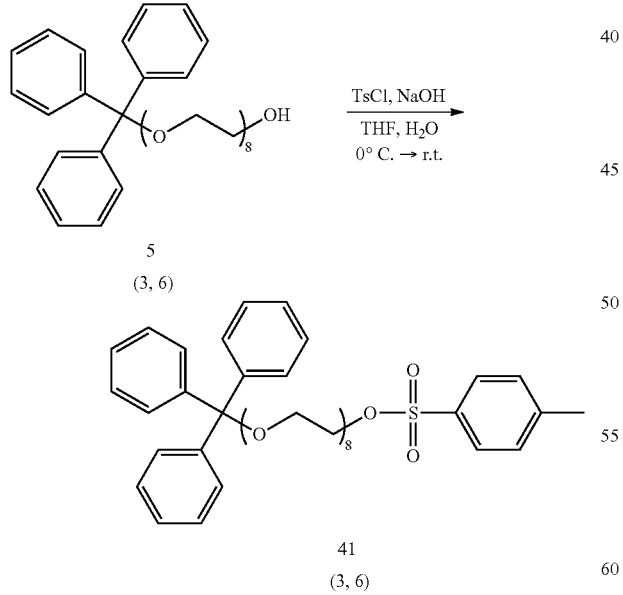

Tetrahydrofuran (200 mL) was added to the reaction product containing the compound 5 (Compound 5: 77.8 g, less than 0.14 mol) in a reactor fitted with a thermometer, a nitrogen inlet tube and a stirrer, and the product was dissolved under a nitrogen atmosphere. Then, the solution was cooled to 0° C. An aqueous sodium hydroxide solution (20 g, 0.5 mol/60 mL) was added, and the mixture was stirred at 0° C. for 20 minutes. A tosyl chloride/tetrahydrofuran solution (30 g, 0.16 mnol/60 mL) was added dropwise to the reaction mixture over 30 minutes, and the mixture was stirred at 0° C. for 1.5 hours. After 1.5 hours, after confirming the disappearance of the compound 5 by TLC, the mixture was stirred at room temperature for 12.5 hours in order to make excess tosyl chloride disappear. After 12.5 hours, the disappearance of tosyl chloride was confirmed by TLC and ion-exchanged water (30 mL) and diethyl ether (50 mL) were added. The mixture was washed once with a saturated aqueous sodium hydrogen carbonate solution (50 mL) and three times with a saturated aqueous sodium chloride solution (50 mL). Sodium sulfate was added to the organic layer for dehydration, followed by dehydration. The filtrate was concentrated under reduced pressure to obtain a reaction product containing compound 41 as a pale yellow transparent liquid. Moreover, it was confirmed by ESI-MS measurement that the obtained reaction product contained the above compounds 3 and 6.

Compound 41

MS (ESI$^+$): Compound 41 785.2 [M+NH$_4$]$^+$, Compound 3 697.0 [M+NH$_4$]$^+$, Compound 6 1048.7 [M+NH$_4$]$^+$
Yield: 86.1 g (Yield: 88%)

Comparative Example 1-4

Synthesis of Compound 42 Having an Ethylene Glycol Chain Length of 8 Units and Having a Hydroxyl Group at One Terminal and a Tosyl Group at One Terminal

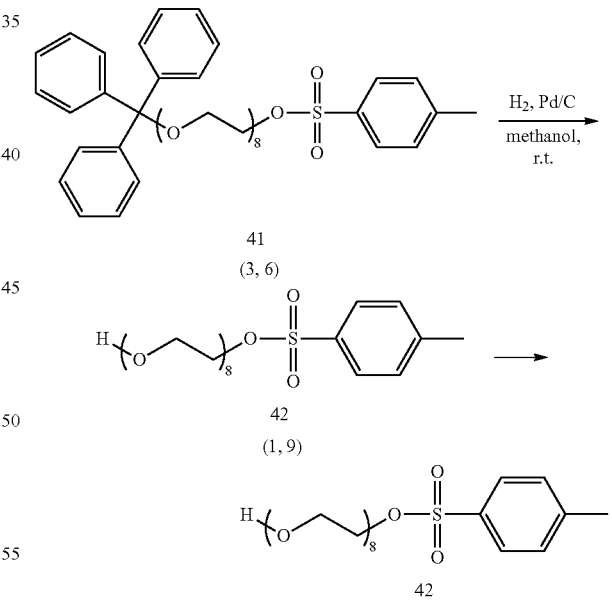

The reaction product containing the compound 41 (compound 41: 85.6 g, less than 0.144 mol), methanol (20 mL), palladium carbon (Pd/C, 2 g) were added to a reaction vessel fitted with a thermometer, a nitrogen inlet tube and a stirrer, hydrogen substitution was performed, and the mixture was stirred at room temperature for 18 hours. After 18 hours, the disappearance of the compound 42 was confirmed by TLC, and Pd/C was removed by celite filtration. Ion-exchanged water (130 mL) was added to the filtrate, and formed triphenylmethane was filtered. Since triphenylmethane remained in the filtrate, it was washed with hexane (100 mL) five times to remove triphenylmethane. The methanol/ion-exchanged water layer was concentrated under reduced pressure to obtain a crude product containing the compound 41. Then, dichloromethane (120 mL) was added to the crude product and the mixture was washed three times with ion-exchanged water (100 mL) and twice with a saturated aqueous sodium chloride solution (100 mL) under the condition of 20° C. Sodium sulfate was added to the organic layer, which was dried and filtered. The filtrate was concentrated under reduced pressure to obtain a purified product of the compound 42 as a pale yellow transparent liquid.

Compound 42

Purified Product $^1$H-NMR (CDCl$_3$, internal standard TMS); δ (ppm):
2.45 (3H, s, —OSO$_2$-Ph-CH$_3$),
2.73 (1H, t, H—(OCH$_2$CH$_2$)$_8$—),
3.45-3.85 (30H, m, —(OCH$_2$CH$_2$)$_7$—OCH$_2$CH$_2$—),
4.16 (2H, t, —(OCH$_2$CH$_2$)$_7$—OCH$_2$CH$_2$—OSO$_2$-Ph-CH$_3$),
7.35 (2H, d, —OSO$_2$-Ph-CH$_3$),
7.80 (2H, d, —OSO$_2$-Ph-CH$_3$)
MS (ESI$^+$): Compound 42 542.4 [M+NH$_4$]$^+$ Crude product MS (ESI$^+$): Compound 42 542.4 [M+NH$_4$]$^+$, Compound 1 212.7 [M+NH$_4$]$^+$, Compound 9 564.5 [M+NH$_4$]$^+$
Yield: 52.0 g (yield: 89%)
Purity: 96.7% (HPLC-RI)

The HPLC measurement conditions used for the purity measurement are shown below.

Apparatus: alliance manufactured by Waters Corporation.
Column: Inertsil ODS-3 (column size: 4.6 mm×25 cm, particle size 5 μm) manufactured by GL Science Inc.
Detector: RI
Developing solvent: a solution of methanol/5 mM ammonium acetate=50/50, Flow rate: 0.6 mL/min
Column temperature: 40° C.
Sample concentration: 0.2 mg/mL
Injection volume: 40 μL The purity value is the ratio of the peak area of the compound 42 to the total peak area detected over the retention time of 10 to 40 min.

Comparative Example 1-5

Synthesis of Compound 45 Having an Ethylene Glycol Chain Length of 8 Units and Having a Tosyl Group at One Terminal and a Tert-Butyl Ester Group at One Terminal The compound 45 (1.0 g, 1.91 mmol), tert-butyl acrylate (1.8 mL, 19 mmol), and toluene (25 mL) were added to a reaction vessel fitted with a thermometer, a nitrogen inlet tube and a stirrer, and they were dissolved under a nitrogen atmosphere. Thereafter, the mixture was cooled to 0° C., powdery potassium hydroxide (53 mg, 0.9 mmol) was added, and the mixture was reacted at 0° C. for 1 hour. After the reaction, ion-exchanged water (20 mL) was added and liquid separation was performed. The organic layer was washed once with a saturated aqueous sodium chloride solution (20 mL). The organic layer was concentrated under reduced pressure to obtain the compound 45 as a pale yellow transparent liquid.

Compound 45

$^1$H-NMR (CDCl$_3$, internal standard TMS); δ (ppm):
1.45 (9H, s, (CH$_3$)$_3$C—O—CO—CH$_2$CH$_2$—),
2.45 (3H, s, —OSO$_2$-Ph-CH$_3$),
2.50 (2H, t, (CH$_3$)$_3$C—O—CO—CH$_2$CH$_2$—),
3.45-3.85 (32H, m, —CH$_2$CH$_2$—(OCH$_2$CH$_2$)$_7$—OCH$_2$CH$_2$—),
4.16 (2H, t, —OCH$_2$CH$_2$—OSO$_2$-Ph-CH$_3$),
7.34 (2H, d, —OSO$_2$-Ph-CH$_3$),
7.80 (2H, d, —OSO$_2$-Ph-CH$_3$)
MS (ESI$^+$): Compound 45 670.6 [M+NH$_4$]$^+$
Yield: 1.06 g (yield: 85%)

Comparative Example 1-6

Synthesis of Compound 46 Having an Ethylene Glycol Chain Length of 8 Units and Having a Phthalimide Group at One Terminal and a Tert-Butyl Ester Group at One Terminal After the compound 45 (1.06 g, 1.60 mmol) and acetonitrile (25 mL) were added to a reaction vessel fitted with a thermometer, a nitrogen inlet tube and a stirrer and the compound was dissolved under a nitrogen atmosphere, phthalimide potassium salt (520 mg, 2.80 mmol) was added, and the mixture was stirred at 80° C. for 8 hours. The disappearance of the compound 45 was confirmed by NMR, and the reaction solution was concentrated. After adding dichloromethane (7 mL) and filtrating the solid content, the filtrate was washed once with a 0.1M aqueous sodium hydroxide solution (7 mL) and once with a saturated aqueous sodium chloride solution (10 mL). Sodium sulfate was added to the organic layer for dehydration, followed by filtration. The filtrate was concentrated under reduced pressure to obtain the compound 46 as a pale yellow transparent liquid.

Compound 46
$^1$H-NMR (CDCl$_3$, internal standard TMS); δ (ppm):
1.45 (9H, s, (CH$_3$)$_3$C—O—CO—CH$_2$CH$_2$—),
2.50 (2H, t, (CH$_3$)$_3$C—O—CO—CH$_2$CH$_2$—),
3.45-3.85 (32H, m, —CH$_2$CH$_2$—(OCH$_2$CH$_2$)$_7$—OCH$_2$CH$_2$—),
3.90 (2H, t, —OCH$_2$CH$_2$-phthalimide),
7.71 (2H, dd, -phthalimide),
7.80 (2H, dd, -phthalimide)
MS (ESI$^+$): Compound 46 945.7 [M+NH$_4$]$^+$
Yield: 965 mg (yield: 95%)

Comparative Example 1-7

Synthesis of compound 9 in which a is 8 and R$^2$ is tert-butyl group in formula (8)

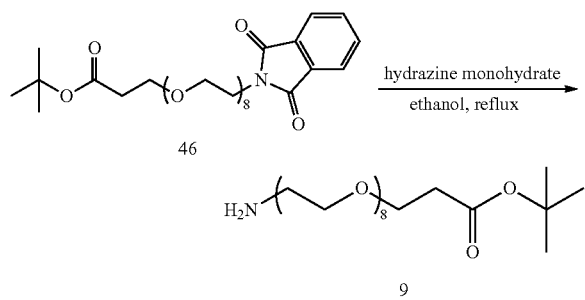

The compound 46 (510 mg, 0.80 mmol), ethanol (10 mL) and hydrazine monohydrate (334 mg, 6.70 mmol) were added to a reaction vessel fitted with a thermometer, a nitrogen inlet tube and a stirrer, and a reaction was performed at 85° C. for 45 minutes. After cooling to room temperature, in order to dissolve precipitated white solid, a 12% aqueous potassium carbonate solution (5 mL) was added and then the mixed solution was concentrated under reduced pressure. Next, ion-exchanged water (3 mL) was added, concentrated hydrochloric acid (0.6 mL) was added to adjust the pH to 3, and the solid mass was filtered. The filtrate was washed three times with dichloromethane and the aqueous layer was saturated by adding sodium chloride. This aqueous solution was extracted 5 times with dichloromethane, and the organic layer was dehydrated over sodium sulfate and filtered. The filtrate was concentrated under reduced pressure to obtain the compound 9 as a pale yellow transparent liquid.

Compound 9
$^1$H-NMR (CDCl$_3$, internal standard TMS); δ (ppm):
1.44 (9H, s, —CH$_2$CH$_2$—COO—C(CH$_3$)$_3$),
2.50 (2H, t, —CH$_2$CH$_2$—COO—C(CH$_3$)$_3$),
3.1 (2H, t, H$_2$N—CH$_2$CH$_2$O—(CH$_2$CH$_2$O)$_7$—),
3.45-3.85 (32H, m, H$_2$N—CH$_2$CH$_2$O—(CH$_2$CH$_2$O)$_7$—CH$_2$CH$_2$—)
Yield: 400 mg (yield: 99%)

Comparative Example 1-8

Synthesis of Compound 10 in which a in Formula (1) is 8

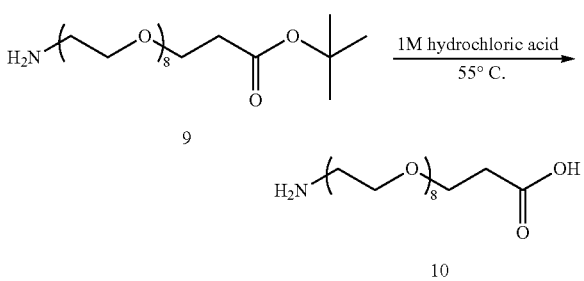

After the compound 9 (400 mg, 0.80 mmol) and 1M hydrochloric acid (0.5 mL) were added to a reaction vessel fitted with a thermometer, a nitrogen inlet tube and a stirrer, the compound was dissolved and then the mixture was stirred at 55° C. for 5 hours. After cooling to 15° C., a 10M aqueous sodium hydroxide solution was added to adjust the pH to 5. Dichloromethane (10 mL) was added to the solid mass obtained by performing azeotropic dehydration of water with toluene (5 mL) twice, and the mixture was filtered. The filtrate was concentrated under reduced pressure to obtain the compound 10 as a pale yellow transparent liquid.

Compound 10
$^1$H-NMR (CD$_3$OD, internal standard TMS); δ (ppm):
2.56 (2H, t, —CH$_2$CH$_2$—COOH),
3.17 (2H, t, H$_2$N—CH$_2$CH$_2$O—),
3.6-3.9 (32H, m, —CH$_2$CH$_2$O—(CH$_2$CH$_2$O)$_7$—CH$_2$CH$_2$—)
Yield: 320 mg (yield: 83%)
Purity: 95.6% (HPLC-RI)
The HPLC measurement conditions used for the purity measurement are shown below.
Apparatus: alliance manufactured by Waters Corporation.
Column: Inertsil ODS-3 (column size: 4.6 mm×25 cm, particle size 5 μm) manufactured by GL Science Inc.
Detector: RI
Developing solvent: a solution of methanol/5 mM ammonium acetate=15/85,
Flow rate: 1.0 mL/min
Column temperature: 40° C.
Sample concentration: 1 mg/mL
Injection volume: 50 μL Comparative Example 2, Production Method for Obtaining Compound 18 Via Tosylation Step Compound 18 in which a in formula (1) is 12 was synthesized by the production method described in Patent Literature 4.

Comparative Example 2-1

Synthesis of Compound 11 in which a is 8, $R^1$ is Trityl Group, and L is Mesyl Group in Formula (3)

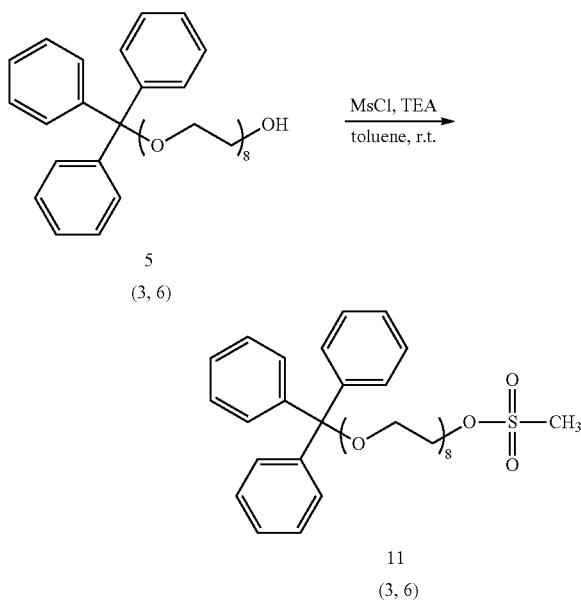

The reaction product containing the compound 5 (compound 5: 72.7 g, less than 0.12 mol) and toluene (350 mL) were added to a reaction vessel fitted with a thermometer, a nitrogen inlet tube and a stirrer and the product was dissolved under a nitrogen atmosphere, followed by addition of triethylamine (20 ml, 0.14 mol). Methanesulfonyl chloride (10 mL, 0.13 mol) was added dropwise at 10° C., and the mixture was stirred at room temperature for 2 hours. After 2 hours, the disappearance of the compound 5 was confirmed by TLC analysis, a 1M aqueous hydrochloric acid solution (100 mL) was added, and liquid separation was performed. The organic layer was washed once with a 1M aqueous hydrochloric acid solution (100 mL), twice with a saturated aqueous sodium hydrogen carbonate solution (100 mL), and once with a saturated aqueous sodium chloride solution (100 mL). Sodium sulfate was added to the organic layer for dehydration, followed by filtration. The filtrate was concentrated under reduced pressure to obtain a reaction product containing the compound 11 as a pale yellow transparent liquid. Moreover, it was confirmed from ESI-MS measurement that the obtained reaction product contained the above compounds 3 and 6.

Compound 11
$^1$H-NMR (CDCl$_3$, internal standard TMS); δ (ppm):
3.07 (3H, s, —OCH$_2$CH$_2$—O—SO$_2$CH$_3$),
3.23 (2H, t, (C$_6$H$_5$)$_3$C—OCH$_2$CH$_2$—, including those derived from compounds 3 and 6)
3.45-3.85 (28H, m, —OCH$_2$CH$_2$—(OCH$_2$CH$_2$)$_6$—OCH$_2$CH$_2$—, including those derived from compounds 3 and 6),
4.37 (2H, t, —OCH$_2$CH$_2$—O—SO$_2$CH$_3$),
7.21-7.47 (15H, m, (C$_6$H$_5$)$_3$C—OCH$_2$CH$_2$—, including those derived from compounds 3 and 6)
MS (ESI$^+$): Compound 11 708.3 [M+NH$_4$]$^+$, Compound 3 696.4 [M+NH$_4$]$^+$, Compound 6 1048.5 [M+NH$_4$]$^+$
Yield: 80.1 g From the $^1$H-NMR measurement results of the compound 11 of Comparative Example 2-1, it was confirmed that the compounds 3 and 6 were contained in an amount of about 9.5 mol % (compound 3: 4.8 mol %, compound 6: 4.7 mol %, rough estimation).

A calculation expression of the contents of the compounds 3 and 6 on the basis of a δ 3.23 peak is expressed by the following expression.

(((2−[δ 4.32])/4H)/([δ 4.32]/2H))×100 (mol %)

As the content of the compound 3, the value calculated in Comparative Example 1-1 is applied.

Further, the reaction product 5 used in Comparative Example 2-1 contains the compounds 3 and 6 in an amount of about 11.7 wt %.

Comparative Example 2-2

Synthesis of Compound 12 in which a is 12 and $R^1$ is Trityl Group in Formula (4)

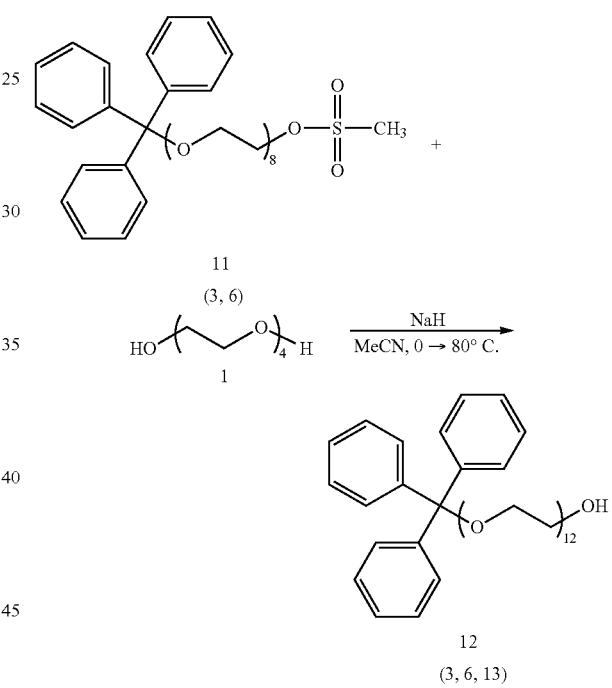

Sodium hydride (6.6 g) was placed in a reactor fitted with a thermometer, a nitrogen inlet tube and a stirrer, and after nitrogen substitution, MeCN (200 mL) was added and the mixture was cooled to 0° C. MeCN (50 mL) was mixed with tetraethylene glycol 1 (180 g, 0.93 mol) azeotropically dehydrated with toluene (50 mL), and this mixed solution was added dropwise over 30 minutes. After completion of the dropwise addition, MeCN (50 mL) was mixed with the reaction product containing the compound 11 (compound 11: 80.1 g, less than 0.12 mol), and the mixed solution was added dropwise over 15 minutes. After completion of the dropwise addition, the reaction mixture was heated to 80° C. and stirred for 3 hours. After 3 hours, it was confirmed using $^1$H-NMR that the compound 11 had disappeared, and the mixture was allowed to cool until the temperature became 40° C. or lower. The reaction mixture solution was concentrated under reduced pressure, and toluene (200 mL) was added to the residue. This toluene solution was washed twice with a saturated aqueous ammonium chloride solution (100 mL) and three times with a saturated aqueous sodium chloride solution (100 mL). Sodium sulfate was added to the organic layer for dehydration, followed by filtration. The filtrate was concentrated under reduced pressure to obtain a reaction product containing the compound 12 as a pale yellow transparent liquid. Moreover, it was confirmed from ESI-MS and $^1$H-NMR measurement that the obtained reaction product contained the above compounds 3, 6 and 13.

Compound 12

$^1$H-NMR (CDCl$_3$, internal standard TMS); δ (ppm):
2.56 (1H, t, —C—(OCH$_2$CH$_2$)$_{12}$—OH),
3.23 (2H, t, (C$_6$H$_5$)$_3$C—OCH$_2$CH$_2$—, including those derived from compounds 3, 6 and 13)
3.45-3.85 (46H, m, —OCH$_2$CH$_2$—(OCH$_2$CH$_2$)$_{11}$—OH, including those derived from compounds 3, 6 and 13),
7.21-7.47 (15H, m, (C$_6$H$_5$)$_3$C—OCH$_2$CH$_2$—, including those derived from compounds 3, 6 and 13)
MS (ESI$^+$): Compound 12 806.4 [M+NH$_4$]$^+$, Compound 3 696.8 [M+NH$_4$]$^+$, Compound 6 1048.1 [M+NH$_4$]$^+$, Compound 13 1400.9 [M+NH$_4$]$^+$
Yield: 85.4 g Comparative Example 2-3

Synthesis of Compound 43 in which a is 12, R$^1$ is Trityl Group, and L is Tosyl Group in Formula (3)

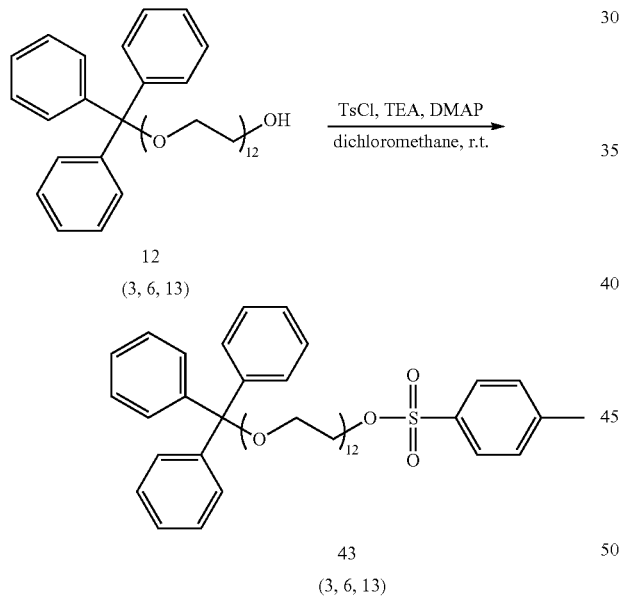

After the reaction product containing the compound 12 (compound 12: 57.3 g, less than 72.7 mmol) and dichloromethane (280 mL) were added to a reaction vessel fitted with a thermometer, a nitrogen inlet tube and a stirrer, the product was dissolved under a nitrogen atmosphere, triethylamine (10 mL, 73 mol), 4-dimethylaminopyridine (888 mg, 7.27 mmol) and TsCl (12.5 g, 65.5 mmol) were added, and the mixture was stirred at room temperature for 4.5 hours. After 4.5 hours, the disappearance of TsCl was confirmed by $^1$H-NMR analysis, a 1M aqueous hydrochloric acid solution (150 mL) was added, and liquid separation was performed. The organic layer was washed once with a 1M aqueous hydrochloric acid solution (150 mL), twice with a saturated aqueous sodium hydrogen carbonate solution (150 mL), and once with a saturated aqueous sodium chloride solution (150 mL). Sodium sulfate was added to the organic layer for dehydration, followed by filtration. The filtrate was concentrated under reduced pressure to obtain a reaction product containing the compound 43 as a pale yellow transparent liquid. Moreover, it was confirmed from ESI-MS measurement that the obtained reaction product contained the above compounds 3, 6 and 13.

Compound 43

MS (ESI$^+$): Compound 43 960.3 [M+NH$_4$]$^+$, Compound 3 696.3 [M+NH$_4$]$^+$, Compound 6 1048.2 [M+NH$_4$]$^+$, Compound 13 1400.8 [M+NH$_4$]$^+$
Yield: 69.1 g (yield: 101%)

Comparative Example 2-4

Synthesis of Compound 44 Having Ethylene Glycol Chain Length of 12 Units and Having Hydroxyl Group at One Terminal and Tosyl Group at One Terminal

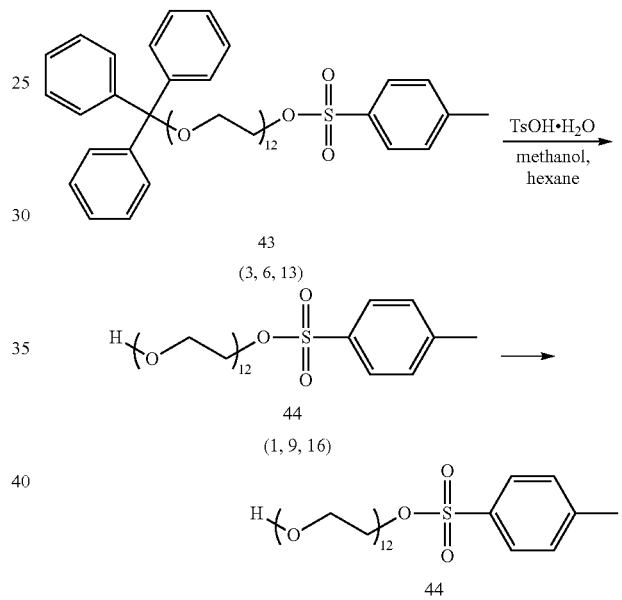

The reaction product containing compound 43 (compound 43: 69.1 g, less than 73.3 mmol) and methanol (550 L) were added to a reaction vessel fitted with a thermometer, a nitrogen inlet tube and a stirrer. After the compound was dissolved under a nitrogen atmosphere, p-toluenesulfonic acid monohydrate (6.97 g, 36.7 mmol) and hexane (200 mL) were added. After stirring at room temperature for 30 minutes, the hexane layer was removed, hexane (200 mL) was added again, and the mixture was stirred for 30 minutes. After performing the same operation six times, the disappearance of the compounds 43, 3, 6 and 13 was confirmed as a result of $^1$H-NMR measurement, and a saturated aqueous sodium hydrogen carbonate solution (200 mL) was added. The mixed solution was washed twice with hexane (200 mL) to remove trityl methyl ether. The methanol solution was concentrated under reduced pressure, and dichloromethane (200 mL) was added and the mixture was washed three times with ion-exchanged water (200 mL) and once with a saturated aqueous sodium chloride solution (200 mL) under the condition of 20° C. or lower. Magnesium sulfate was added to the organic layer for dehydration, followed by filtration. The filtrate was concentrated under reduced pressure to obtain the compound 44 as a pale yellow transparent liquid.

Compound 44

Purified Product $^1$H-NMR (CDCl$_3$, internal standard TMS); δ (ppm):

2.45 (3H, s, —OSO$_2$-Ph-CH$_3$), 2.73 (1H, t, H—(OCH$_2$CH$_2$)$_8$—), 3.45-3.85 (46H, m, —(OCH$_2$CH$_2$)$_{11}$—OCH$_2$CH$_2$—), 4.16 (2H, t, —(OCH$_2$CH$_2$)$_7$—OCH$_2$CH$_2$—OSO$_2$-Ph-CH$_3$), 7.35 (2H, d, —OSO$_2$-Ph-CH$_3$), 7.80 (2H, d, —OSO$_2$-Ph-CH$_3$)

MS (ESI$^+$): Compound 44 718.3 [M+NH$_4$]$^+$

Crude product

MS(ESI$^+$): Compound 44 718.3 [M+NH$_4$]$^+$, Compound 1 212.3 [M+NH$_4$]$^+$, Compound 9 564.5 [M+NH$_4$]$^+$, Compound 16 916.4 [M+NH$_4$]$^+$ Yield: 30.3 g (yield: 59%)

Purity: 94.9% (HPLC-RI)

The HPLC measurement conditions used for the purity measurement are shown below.

Apparatus: alliance manufactured by Waters Corporation.

Column: Inertsil ODS-3 (column size: 4.6 mm×25 cm, particle size 5 μm) manufactured by GL Science Inc.

Detector: RI

Developing solvent: a solution of methanol/5 mM ammonium acetate=55/45

Flow rate: 0.6 mL/min

Column temperature: 40° C.

Sample concentration: 0.2 mg/mL

Injection volume: 40 μL

The purity value is the ratio of the peak area of the compound 44 to the total peak area detected over the retention time of 11 to 40 min.

Comparative Example 2-5

Synthesis of Compound 47 Having Ethylene Glycol Chain Length of 12 Units and Having Tosyl Group at One Terminal and Tert-Butyl Ester Group at One Terminal

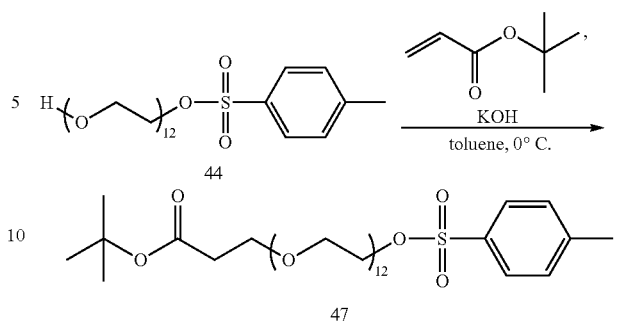

The compound 44 (4.96 g, 7.08 mmol), tert-butyl acrylate (3.09 mL, 21.2 mmol), and toluene (100 mL) were added to a reaction vessel fitted with a thermometer, a nitrogen inlet tube and a stirrer, and they were dissolved under a nitrogen atmosphere. Thereafter, the mixture was cooled to 0° C., powdery potassium hydroxide (199 mg, 3.54 mmol) was then added, and the mixture was reacted at 0° C. for 1 hour. After the reaction, a saturated aqueous ammonium chloride solution (50 mL) was added and liquid separation was performed. The organic layer was washed once with a saturated aqueous sodium chloride solution (50 mL). Sodium sulfate was added to the organic layer for dehydration, followed by filtration. The filtrate was concentrated under reduced pressure to obtain the compound 47 as a pale yellow transparent liquid.

Compound 47

$^1$H-NMR (CDCl$_3$, internal standard TMS); δ (ppm):

1.45 (9H, s, (CH$_3$)$_3$C—O—CO—CH$_2$CH$_2$—), 2.45 (3H, s, —OSO$_2$-Ph-CH$_3$), 2.50 (2H, t, (CH$_3$)$_3$C—O—CO—CH$_2$CH$_2$—), 3.45-3.85 (48H, m, —CH$_2$CH$_2$—(OCH$_2$CH$_2$)$_{11}$—OCH$_2$CH$_2$—), 4.16 (2H, t, —OCH$_2$CH$_2$—OSO$_2$-Ph-CH$_3$), 7.34 (2H, d, —OSO$_2$-Ph-CH$_3$), 7.80 (2H, d, —OSO$_2$-Ph-CH$_3$)

MS (ESI$^+$): Compound 47 847.0 [M+NH$_4$]$^+$

Yield: 5.43 g (Yield: 93%)

Comparative Example 2-6

Synthesis of Compound 48 Having Ethylene Glycol Chain Length of 12 Units and Having Phthalimide Group at One Terminal and Tert-Butyl Ester Group at One Terminal

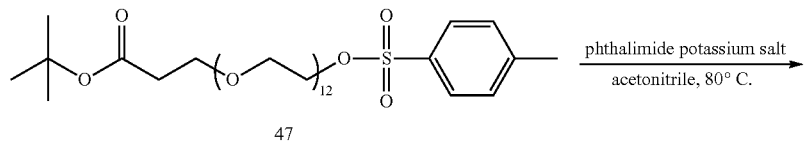

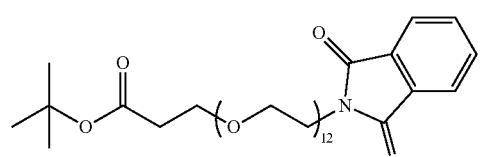

After the compound 47 (5.43 g, 6.55 mmol) and acetonitrile (45 mL) were added to a reaction vessel fitted with a thermometer, a nitrogen inlet tube and a stirrer and the compound was dissolved under a nitrogen atmosphere, phthalimide potassium salt (1.58 g, 8.52 mmol) was added, and the mixture was stirred at 80° C. for 18 hours. The disappearance of the compound 48 was confirmed by NMR, and the reaction solution was concentrated. After adding dichloromethane (50 mL) to the residue and filtering the solid mass, the filtrate was washed once with a 0.1M aqueous sodium hydroxide solution (50 mL) and once with a saturated aqueous sodium chloride solution (50 mL). Sodium sulfate was added to the organic layer for dehydration, followed by filtration. The filtrate was concentrated under reduced pressure to obtain the compound 48 as a pale yellow transparent liquid.

Compound 48
$^1$H-NMR (CDCl$_3$, internal standard TMS); δ (ppm):
1.45 (9H, s, (CH$_3$)$_3$C—O—CO—CH$_2$CH$_2$—),
2.50 (2H, t, (CH$_3$)$_3$C—O—CO—CH$_2$CH$_2$—),
3.45-3.85 (48H, m, —CH$_2$CH$_2$—(OCH$_2$CH$_2$)$_{11}$—OCH$_2$CH$_2$—),
3.90 (2H, t, —OCH$_2$CH$_2$-phthalimide),
7.71 (2H, dd, -phthalimide),
7.80 (2H, dd, -phthalimide)
MS (ESI$^+$): Compound 48 828.1 [M+NH$_4$]$^+$
Yield: 4.26 g (yield: 81%)

Comparative Example 2-7

Synthesis of Compound 17 in which a is 12 and R$^2$ is Tert-Butyl Group in Formula (8)

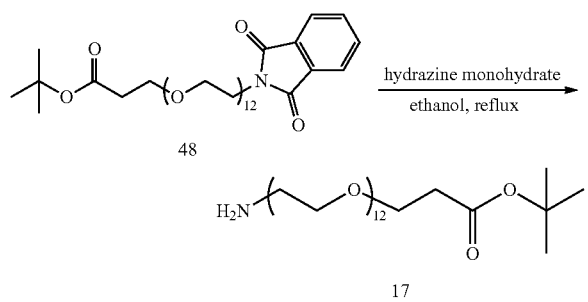

The compound 48 (4.26 g, 5.30 mmol), ethanol (60 mL) and hydrazine monohydrate (3.86 mL, 79.5 mmol) were added to a reaction vessel fitted with a thermometer, a nitrogen inlet tube and a stirrer, and a reaction was performed at 85° C. for 1 hour. After cooling to room temperature, in order to dissolve precipitated white solid, a 12% aqueous potassium carbonate solution (5 mL) was added and then the mixed solution was concentrated under reduced pressure. Ion-exchanged water (20 mL) was added to the residue, concentrated hydrochloric acid was added to adjust the pH to 3, and the solid mass was filtered. Sodium chloride was added to the filtrate, which was extracted twice with dichloromethane (20 mL). The organic layer was dehydrated over sodium sulfate and filtered. The filtrate was concentrated under reduced pressure to obtain the compound 17 as a pale yellow transparent liquid.

Compound 17
$^1$H-NMR (CDCl$_3$, internal standard TMS); δ (ppm):
1.44 (9H, s, —CH$_2$CH$_2$—COO—C(CH$_3$)$_3$),
2.50 (2H, t, —CH$_2$CH$_2$—COO—C(CH$_3$)$_3$),
3.1 (2H, t, H$_2$N—CH$_2$CH$_2$O—(CH$_2$CH$_2$O)$_{11}$—),
3.45-3.85 (48H, m, H$_2$N—CH$_2$CH$_2$O—(CH$_2$CH$_2$O)$_{11}$—CH$_2$CH$_2$—)
Yield: 3.13 g (yield: 88%)

Comparative Example 2-8

Synthesis of Compound 18 in which a in Formula (1) is 12

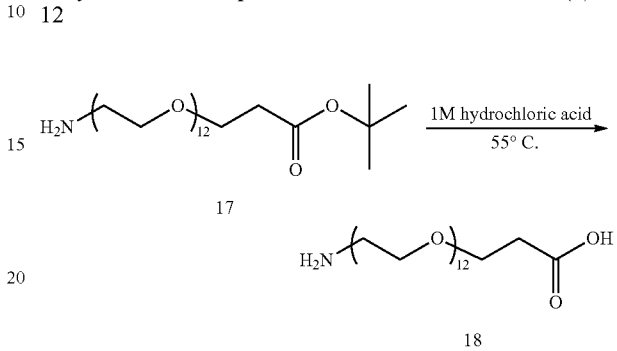

After the compound 17 (3.13 g, 4.65 mmol) and 1M hydrochloric acid (3 mL) were added to a reaction vessel fitted with a thermometer, a nitrogen inlet tube and a stirrer, the compound was dissolved and then the mixture was stirred at 55° C. for 2 hours. After cooling to 15° C., the mixture was diluted with ion-exchanged water (5 mL) and was washed with dichloromethane (10 mL) three times. A 2M aqueous sodium hydroxide solution was added to the aqueous layer to adjust the pH to 9. The aqueous solution was washed three times with dichloromethane (10 mL) and the aqueous layer was saturated by adding sodium chloride. This aqueous solution was extracted three times with chloroform (10 mL), and the organic layer was dehydrated over sodium sulfate and filtered. The filtrate was concentrated under reduced pressure to obtain the compound 18 as a pale yellow transparent liquid.

Compound 18
$^1$H-NMR (CD$_3$OD, internal standard TMS); δ (ppm):
2.56 (2H, t, —CH$_2$CH$_2$—COOH),
3.17 (2H, t, H$_2$N—CH$_2$CH$_2$O—),
3.6-3.9 (48H, m, —CH$_2$CH$_2$O—(CH$_2$CH$_2$O)$_{11}$—CH$_2$CH$_2$—)
Yield: 2.32 g (yield: 76%)
Purity: 98.0% (HPLC-RI)

The HPLC measurement conditions used for the purity measurement are shown below.
Apparatus: alliance manufactured by Waters Corporation,
Column: Inertsil ODS-3 (column size: 4.6 mm×25 cm, particle size 5 μm) manufactured by GL Science Inc,
Detector: RI,
Developing solvent: a solution of methanol/5 mM ammonium acetate=27.5/72.5,
Flow rate: 1.0 mL/min,
Column temperature: 40° C.,
Sample concentration: 2 mg/mL, Injection volume: 50 μL

Comparative Example 3

Calculation Expression of Contents of Compounds 3, 6 and 13 Having Trityl Groups at Both Terminals in Reaction Product Containing Compound 12 Obtained in Comparative Example 2-2

Synthesis of Compound 19 in which a is 12, $R^1$ is Trityl Group, and L is Mesyl Group in Formula (3)

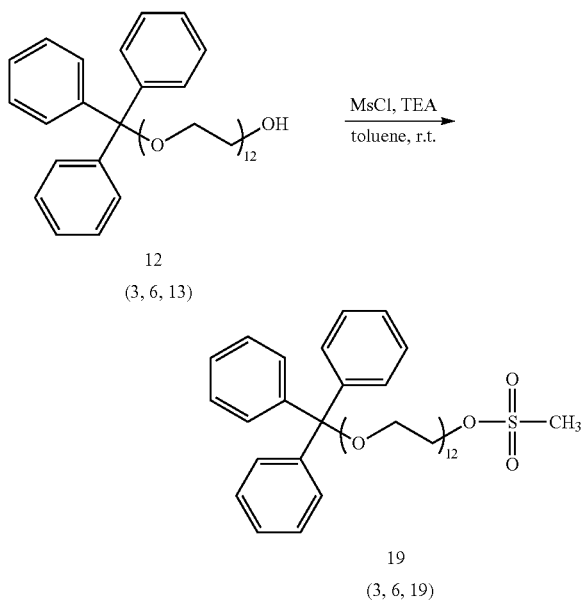

The reaction product containing the compound 12 (compound 12: 25 g, less than 317 mmol) and toluene (125 mL) were added to a reaction vessel fitted with a thermometer, a nitrogen inlet tube and a stirrer and the product was dissolved under a nitrogen atmosphere, followed by addition of triethylamine (5.3 ml, 38 mmol). Methanesulfonyl chloride (2.7 mL, 35 mmol) was added dropwise at 10° C., and the mixture was stirred at room temperature for 2 hours. After 2 hours, the disappearance of the compound 12 was confirmed by TLC analysis, a 1M aqueous hydrochloric acid solution (50 mL) was added, and liquid separation was performed. The organic layer was washed once with a 1M aqueous hydrochloric acid solution (50 mL), twice with a saturated aqueous sodium hydrogen carbonate solution (50 mL), and once with a saturated aqueous sodium chloride solution (50 mL). Sodium sulfate was added to the organic layer for dehydration, followed by filtration. The filtrate was concentrated under reduced pressure to obtain a reaction product containing the compound 19 as a pale yellow transparent liquid. Moreover, it was confirmed from ESI-MS measurement that the obtained reaction product contained the above compounds 3, 6 and 13.

Compound 19

$^1$H-NMR (CDCl$_3$, internal standard TMS); δ (ppm):
3.07 (3H, s, —OCH$_2$CH$_2$—O—SO$_2$CH$_3$),
3.23 (2H, t, (C$_6$H$_5$)$_3$C—OCH$_2$CH$_2$—, including those derived from compounds 3, 6 and 13)
3.45-3.85 (44H, m, —OCH$_2$CH$_2$—(OCH$_2$CH$_2$)$_{10}$—OCH$_2$CH$_2$—, including those derived from compounds 3, 6 and 13),
4.37 (2H, t, —OCH$_2$CH$_2$—O—SO$_2$CH$_3$),
7.21-7.47 (15H, m, (C$_6$H$_5$)$_3$C—OCH$_2$CH$_2$—, including those derived from compounds 3, 6 and 13)

MS (ESI$^+$): Compound 19 884.9 [M+NH$_4$]$^+$, Compound 3 696.8 [M+NH$_4$]$^+$, Compound 6 1049.4 [M+NH$_4$]$^+$, Compound 13 1401.3 [M+NH$_4$]$^+$
Yield: 26 g From the $^1$H-NMR measurement results of the compound 19 of Comparative Example 3, it was confirmed that the compounds 3, 6 and 13 were contained in an amount of about 9.8 mol % (compound 3: 4.8 mol %, compound 6: 4.7 mol %, compound 13: 0.3 mol %, rough estimation).

A calculation expression of the contents of the compounds 3, 6 and 13 content on the basis of a δ 3.23 peak is expressed by the following expression.

$$(((2-[δ\ 4.32])/4H)/([δ\ 4.32]/2H)) \times 100\ (\text{mol\ \%})$$

As the compounds 3 and 6, the values calculated in Comparative Examples 1-1 and 2-1 are applied.

Further, the reaction product 12 used in Comparative Example 3 contains the compounds 3, 6 and 13 in an amount of about 9.7 wt %.

Comparison of total yields until obtaining compound 10 of hetero monodisperse polyethylene glycol having amino group and carboxyl group at respective both terminals obtained using compound 5 of hetero monodisperse polyethylene glycol having hydroxyl group and trityl group at respective both terminals as raw material Table 1 shows total yields when the formula (1) was produced from the formula (4) in the case where a was 8 or 12.

TABLE 1

| Value of a | Example | Comparative Example |
|---|---|---|
| 8 | 64% | 58% |
| 12 | 72% | 34% |

The total yields were calculated following the following expression.

Case of $a=8$: (Value obtained by multiplying yields in respective steps until obtaining compound 10 from compound 5)×(Pure content of compound 10 in which $a$ is 8)/(Pure content of compound 5 in which $a$ is 8)

Case of $a=12$: (Value obtained by multiplying yields in respective steps until obtaining compound 18 from compound 12)×(Pure content of compound 18 in which $a$ is 12)/(Pure content of compound 12 in which $a$ is 12)

In the expression for determining the total yield, the pure content of the compound 5 in which a is 8 is a value obtained by multiplying a value obtained by subtracting the contents of the compounds 3 and 6 having trityl groups at both terminals from the amount of the reaction product containing the compound 5 obtained in Example 1-2 by the purity of the compound 42 obtained in Example 4. Further, it is a value obtained by multiplying a value obtained by subtracting the contents of the compounds 3 and 6 having trityl groups at both terminals from the amount of the reaction product containing the compound 5 obtained in Comparative Example 1-2 by the purity of the compound 42 obtained in Comparative Example 1-4.

In the expression for determining the total yield, the pure content of the compound 12 in which a is 12 is a value obtained by multiplying a value obtained by subtracting the contents of the compounds 3, 6 and 13 having trityl groups at both terminals from the amount of the reaction product containing the compound 12 obtained in Example 2-2 by the purity of the compound 44 obtained in Example 5. Further, it is a value obtained by multiplying a value obtained by subtracting the contents of the compounds 3, 6 and 13 having trityl groups at both terminals from the amount of the reaction product containing the compound 5 obtained in Comparative Example 2-2 by the purity of the compound 44 obtained in Comparative Example 2-4.

In the expressions for determining the total yields, the pure contents of the compound 10 in which a is 8 and the compound 18 in which a is 12 correspond to the purities determined by HPLC, respectively.

In the conventional production method, the hydroxyl group is once converted into a tosyl group in order to purify impurities containing trityl groups at both terminals, which are different in chain length and have specific molecular weights, formed as by-products in the chain length extension step. On the other hand, by removing the impurities without this step, the number of steps is smaller than before, and the presence of the residual unreacted raw material and the formation of reaction by-products which may cause a yield decrease can be suppressed, so that the yield could be improved.

INDUSTRIAL APPLICABILITY

According to the present invention, it is possible to provide a novel method for producing a highly pure hetero-type monodisperse polyethylene glycol having an amino group and a carboxyl group at respective both terminals.

Although the present invention has been described in detail and with reference to specific embodiments, it will be apparent to those skilled in the art that various changes and modifications can be made without departing from the spirit and scope of the present invention.

This application is based on a Japanese patent application filed on Mar. 29, 2019 (Japanese Patent Application No. 2019-065528), the contents of which are incorporated herein by reference.

The invention claimed is:

1. A method for producing a hetero-type monodisperse polyethylene glycol represented by the formula (1), which comprises the following steps (A), (B), (C), (D), (E) and (F):

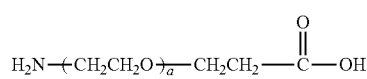
(1)

wherein, in the formula (1), a represents an integer of 6 to 12,

Step (A): a step of carrying out a nucleophilic substitution reaction between a compound of the formula (2) and a compound of the formula (3) so as to satisfy the requirement of the expression (F1) to obtain a compound of the formula (4):

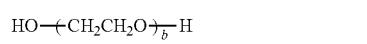
(2)

wherein, in the formula (2), b represents an integer of 3 to 9,

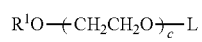
(3)

wherein, in the formula (3), L represents a mesyl group or a tosyl group, $R^1$ represents a trityl group or a benzyl group, and c represents an integer of 3 to 9, $$6 \leq b + c \leq 12 \quad (F1)$$

$$R^1O\text{−}(CH_2CH_2O)_a\text{−}H \quad (4)$$

wherein, in the formula (4), $R^1$ represents a trityl group or a benzyl group and a represents an integer of 6 to 12;

Step (B): a step of carrying out Michael addition reaction of a compound of the formula (5) to the compound of the formula (4) obtained in the step (A) under a temperature condition of 10° C. or lower to obtain a compound of the formula (6),

(5)

wherein, in the formula (5), $R^2$ represents a hydrocarbon group having 1 to 6 carbon atoms,

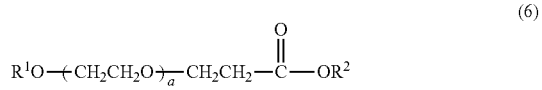
(6)

wherein, in the formula (6), $R^1$ represents a trityl group or a benzyl group, $R^2$ represents a hydrocarbon group having 1 to 6 carbon atoms, and a represents an integer of 6 to 12;

Step (C): a step of detritylating or debenzylating the compound of the formula (6) obtained in the step (B) to obtain a reaction product containing a compound of the formula (7),

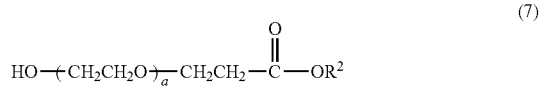
(7)

wherein, in the formula (7), $R^2$ represents a hydrocarbon group having 1 to 6 carbon atoms and a represents an integer of 6 to 12;

Step (D): a step of purifying the compound of the formula (7) from the reaction product obtained in the step (C);

Step (E): a step of reacting the compound of the formula (7) obtained in the step (D) with phthalimide and performing dephthalimidation to obtain a compound of the formula (8),

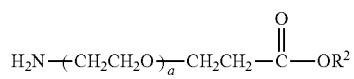
(8)

wherein, in the formula (8), $R^2$ represents a hydrocarbon group having 1 to 6 carbon atoms and a represents an integer of 6 to 12; and Step (F): a step of subjecting the compound of the formula (8) obtained in the step (E) to an acid hydrolysis treatment to obtain the compound represented by the formula (1).

2. The method according to claim 1, wherein the compound of the formula (7) is purified using dichloromethane or chloroform in the step (D).

3. The method according to claim 1, wherein the compound of the formula (7) is purified using water or an aqueous solution having a concentration of an inorganic salt of 10% by weight or less in the step (D).

4. The method according to claim 1, wherein the step (D) comprises a washing step at a temperature of 1 to 25° C.

5. A method for producing a hetero-type monodisperse polyethylene glycol represented by the formula (1), which comprises the following steps (A), (B), (C), (E), (F) and (G):

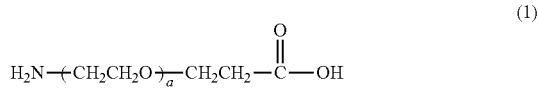
(1)

wherein, in the formula (1), a represents an integer of 13 to 40,

Step (A): a step of carrying out a nucleophilic substitution reaction between a compound of the formula (2) and a compound of the formula (3) so as to satisfy the requirement of the expression (F1) to obtain a compound of the formula (4):

(2)

wherein, in the formula (2), b represents an integer of 3 to 37,

(3)

wherein, in the formula (3), L represents a mesyl group or a tosyl group, $R^1$ represents a trityl group or a benzyl group, and c represents an integer of 3 to 37,

(F1)

(4)

wherein, in the formula (4), $R^1$ represents a trityl group or a benzyl group and a represents an integer of 13 to 40;

Step (B): a step of carrying out Michael addition reaction of a compound of the formula (5) to the compound of the formula (4) obtained in the step (A) under a temperature condition of 10° C. or lower to obtain a compound of the formula (6),

(5)

wherein, in the formula (5), $R^2$ represents a hydrocarbon group having 1 to 6 carbon atoms,

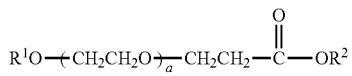
(6)

wherein, in the formula (6), $R^1$ represents a trityl group or a benzyl group, $R^2$ represents a hydrocarbon group having 1 to 6 carbon atoms, and a represents an integer of 13 to 40;

Step (C): a step of detritylating or debenzylating the compound obtained in the step (B) to obtain a compound of the formula (7),

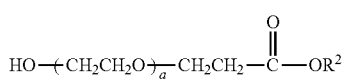
(7)

wherein, in the formula (7), $R^2$ represents a hydrocarbon group having 1 to 6 carbon atoms and a represents an integer of 13 to 40;

Step (E): a step of reacting the compound of the formula (7) obtained in the step (C) with phthalimide and performing dephthalimidation to obtain a compound of the formula (8),

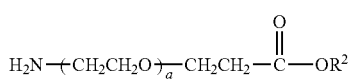
(8)

wherein, in the formula (8), $R^2$ represents a hydrocarbon group having 1 to 6 carbon atoms and a represents an integer of 13 to 40;

Step (F): a step of subjecting the compound of the formula (8) obtained in the step (E) to an acid hydrolysis treatment to obtain a reaction product containing the compound of the formula (1); and Step (G): a step of purifying the compound of the formula (1) from the reaction product obtained in the step (F).

6. The method according to claim 5, wherein an organic solvent to be used for the purifying is dichloromethane or chloroform in the step (G).

7. The method according to claim 5, wherein an aqueous solution to be used for the purifying is a basic aqueous solution of pH 8 or higher in the step (G).

8. The method according to claim 1, wherein $R^2$ of the compound of the formula (5) is an isopropyl group or a tert-butyl group in the step (B).

9. The method according to claim 1, wherein flaky potassium hydroxide or powdery potassium hydroxide is used as a base in the step (B).

10. The method according to claim 2, wherein the compound of the formula (7) is purified using water or an aqueous solution having a concentration of an inorganic salt of 10% by weight or less in the step (D).

11. The method according to claim 2, wherein the step (D) comprises a washing step at a temperature of 1 to 25° C.

12. The method according to claim 3, wherein the step (D) comprises a washing step at a temperature of 1 to 25° C.

13. The method according to claim 6, wherein an aqueous solution to be used for the purifying is a basic aqueous solution of pH 8 or higher in the step (G).

14. The method according to claim 2, wherein $R^2$ of the compound of the formula (5) is an isopropyl group or a tert-butyl group in the step (B).

15. The method according to claim 3, wherein $R^2$ of the compound of the formula (5) is an isopropyl group or a tert-butyl group in the step (B).

16. The method according to claim 4, wherein $R^2$ of the compound of the formula (5) is an isopropyl group or a tert-butyl group in the step (B).

17. The method according to claim 5, wherein $R^2$ of the compound of the formula (5) is an isopropyl group or a tert-butyl group in the step (B).

18. The method according to claim 2, wherein flaky potassium hydroxide or powdery potassium hydroxide is used as a base in the step (B).

19. The method according to claim 3, wherein flaky potassium hydroxide or powdery potassium hydroxide is used as a base in the step (B).

20. The method according to claim 4, wherein flaky potassium hydroxide or powdery potassium hydroxide is used as a base in the step (B).

\* \* \* \* \*